United States Patent
Scherrer et al.

(10) Patent No.: US 9,890,112 B2
(45) Date of Patent: Feb. 13, 2018

(54) COMPOUNDS FOR USE AS THERAPEUTIC AGENTS AFFECTING P53 EXPRESSION AND/OR ACTIVITY

(75) Inventors: Didier Scherrer, Castelnau le Lez (FR); Jamal Tazi, Clapiers (FR); Romain Najman, L'Hay-les-Roses (FR); Florence Mahuteau, Saint Remy les Chevreuses (FR); Pierre Roux, Saint-Gely-du-Fesc (FR)

(73) Assignees: ABIVAX, Paris (FR); CENTRE NATIONAL DE LA RECHERCHE SCIENTIFIQUE, Paris (FR); INSTITUT CURIE, Paris (FR); UNIVERSITE DE MONTPELLIER, Montpellier (FR)

( * ) Notice: Subject to any disclaimer, the term of this patent is extended or adjusted under 35 U.S.C. 154(b) by 332 days.

(21) Appl. No.: 14/009,283

(22) PCT Filed: Apr. 2, 2012

(86) PCT No.: PCT/IB2012/051603
§ 371 (c)(1),
(2), (4) Date: Oct. 1, 2013

(87) PCT Pub. No.: WO2012/131656
PCT Pub. Date: Oct. 4, 2012

(65) Prior Publication Data
US 2014/0206690 A1    Jul. 24, 2014

Related U.S. Application Data

(60) Provisional application No. 61/470,564, filed on Apr. 1, 2011.

(30) Foreign Application Priority Data

Apr. 1, 2011    (EP) .................... 11305385

(51) Int. Cl.
*C07D 401/12*    (2006.01)
*C07C 237/30*    (2006.01)
(Continued)

(52) U.S. Cl.
CPC .......... *C07C 237/30* (2013.01); *A61K 31/166* (2013.01); *A61K 31/167* (2013.01);
(Continued)

(58) Field of Classification Search
CPC .............. A61K 31/4439; A61K 31/496; A61K 31/417; A61K 31/4545; A61K 31/166;
(Continued)

(56) References Cited

U.S. PATENT DOCUMENTS 2,274,620 A    2/1942 Szabo
2,671,805 A    3/1954 Krimmel et al.
(Continued)

FOREIGN PATENT DOCUMENTS

CN    1281694 A    1/2001
CN    1331669 A    1/2002
(Continued)

OTHER PUBLICATIONS

Suzuki; Bioorganic & Medicinal Chemistry, 2009, 17, 5900-5905.*
(Continued)

*Primary Examiner* — Daniel R Carcanague
(74) *Attorney, Agent, or Firm* — Oliff PLC

(57) ABSTRACT

The present invention relates to compound (I)

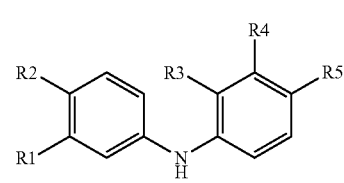

Figure 1:
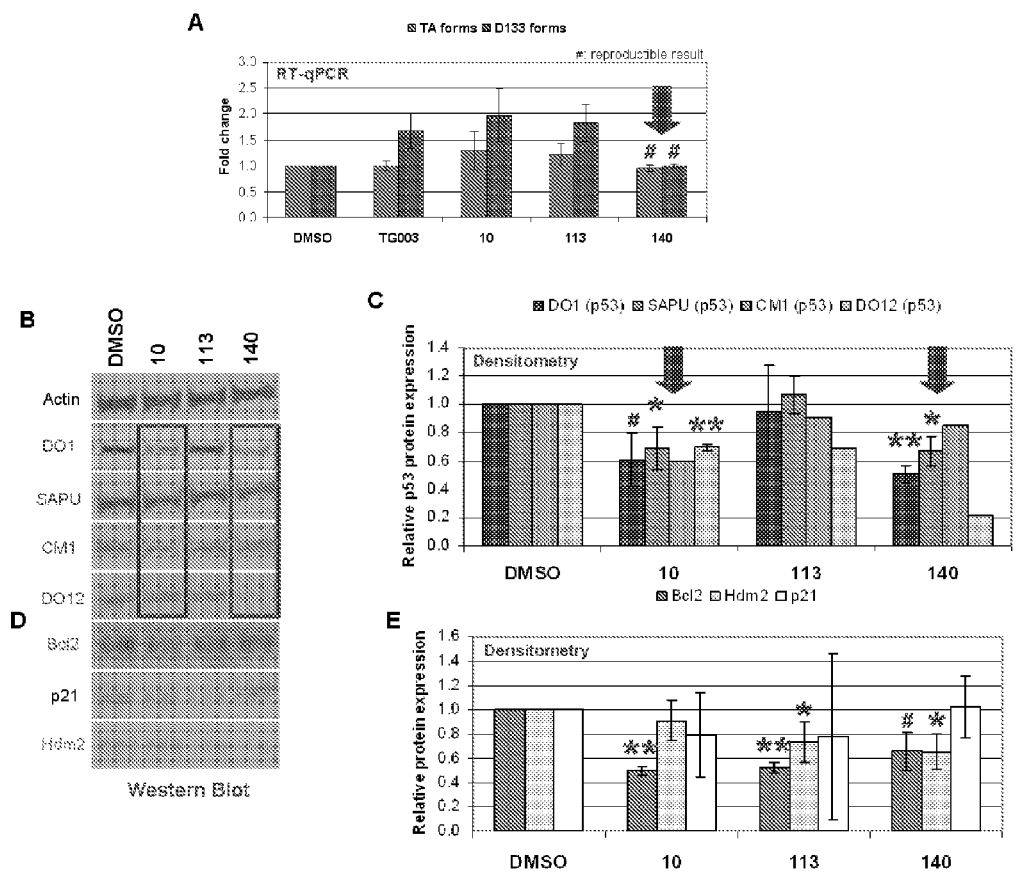

wherein R1 and R2 independently represent a hydrogen atom, a ($C_1$-$C_4$)alkoxy group, a fluoro($C_1$-$C_4$)alkoxy group, a hydroxyl group, a benzyloxy group, a di($C_1$-$C_4$)alkylamino group, a pyridyl-vinyl group, a pyrimidinyl-vinyl group, a styryl group, or a —NHCOphenyl group; R3, R4 and R5 independently represent a hydrogen atom, a ($C_1$-$C_4$) alkyl group, a CONHR6 group, a —CONR7R8 group, a —$SO_2$NHR6 group, or a heteroaryl group optionally substituted by a halogen atom, a —$(CH_2)_n$NR7R8 group or a hydroxy($C_1$-$C_4$)alkyl group; R6 represents a hydrogen atom, a —$(CHR9)_m(CH_2)_n$NR7R8 group or a ($C_1$-$C_6$)alkyl group optionally substituted by a hydroxyl group; or anyone of its pharmaceutically acceptable salt, for use in a method for
(Continued)

preventing, inhibiting or treating a disease in a patient suffering thereof, said disease involving a deregulated p53. Some of said compounds are new and also form part of the invention.

11 Claims, 4 Drawing Sheets

(51) Int. Cl.

| | |
|---|---|
| C07D 213/38 | (2006.01) |
| C07D 233/61 | (2006.01) |
| A61K 31/166 | (2006.01) |
| A61K 31/167 | (2006.01) |
| A61K 31/4164 | (2006.01) |
| A61K 31/417 | (2006.01) |
| A61K 31/4192 | (2006.01) |
| A61K 31/4409 | (2006.01) |
| A61K 31/4439 | (2006.01) |
| A61K 31/4545 | (2006.01) |
| A61K 31/495 | (2006.01) |
| A61K 31/496 | (2006.01) |
| A61K 31/5377 | (2006.01) |
| C07D 213/36 | (2006.01) |
| C07D 233/64 | (2006.01) |
| C07D 249/06 | (2006.01) |

(52) U.S. Cl.
CPC ........ *A61K 31/417* (2013.01); *A61K 31/4164* (2013.01); *A61K 31/4192* (2013.01); *A61K 31/4409* (2013.01); *A61K 31/4439* (2013.01); *A61K 31/4545* (2013.01); *A61K 31/495* (2013.01); *A61K 31/496* (2013.01); *A61K 31/5377* (2013.01); *C07D 213/36* (2013.01); *C07D 213/38* (2013.01); *C07D 233/61* (2013.01); *C07D 233/64* (2013.01); *C07D 249/06* (2013.01); *C07D 401/12* (2013.01)

(58) Field of Classification Search
CPC .............. A61K 31/495; A61K 31/4164; A61K 31/4192; A61K 31/5377; A61K 31/167; A61K 31/4409; C07D 249/06; C07D 213/36; C07D 233/64; C07D 233/61; C07D 213/38; C07D 401/12; C07C 237/30
USPC .......................................................... 546/1
See application file for complete search history.

(56) References Cited

U.S. PATENT DOCUMENTS

| | | | |
|---|---|---|---|
| 3,409,668 A | 11/1968 | Palazzo et al. | |
| 4,001,416 A | 1/1977 | Pommer et al. | |
| 4,434,290 A | 2/1984 | Bisagni et al. | |
| 4,855,308 A | 8/1989 | Kester et al. | |
| 5,079,363 A | 1/1992 | Bouisset et al. | |
| 5,579,033 A | 11/1996 | Rutledge et al. | |
| 6,268,387 B1 | 7/2001 | Connor et al. | |
| 6,419,710 B1 | 7/2002 | Demeulenaere et al. | |
| 8,604,063 B2* | 12/2013 | Tazi ...................... | C07D 213/38 514/345 |
| 2003/0225106 A1 | 12/2003 | Askew et al. | |
| 2004/0054114 A1 | 3/2004 | Mayorga et al. | |
| 2004/0132786 A1* | 7/2004 | Chyba ..................... | C07D 213/75 514/357 |
| 2004/0171833 A1 | 9/2004 | Buchwald et al. | |
| 2005/0154232 A1 | 7/2005 | Lardy et al. | |
| 2007/0054905 A1 | 3/2007 | Tazi et al. | |
| 2007/0072915 A1 | 3/2007 | Lardy et al. | |
| 2007/0129433 A1* | 6/2007 | Lardy ................... | C07C 211/55 514/522 |
| 2009/0118135 A1* | 5/2009 | Reed ..................... | G01N 33/574 506/9 |
| 2011/0053975 A1 | 3/2011 | Tazi et al. | |
| 2015/0315173 A1* | 11/2015 | Roux ................... | C07D 213/75 514/235.8 |

FOREIGN PATENT DOCUMENTS

| | | |
|---|---|---|
| CN | 1590390 A | 3/2005 |
| CN | 1639126 A | 7/2005 |
| CN | 1938261 A | 3/2007 |
| DE | 374 291 C | 4/1923 |
| FR | 2 089 546 A5 | 1/1972 |
| FR | 2 859 474 A1 | 3/2005 |
| FR | 2 859 475 A1 | 3/2005 |
| GB | 995 039 A | 6/1965 |
| GB | 2 327 675 A | 2/1999 |
| JP | A 50-95285 | 7/1975 |
| JP | A 62-158252 | 7/1987 |
| JP | A 11-147874 | 6/1999 |
| NL | 6511104 | 3/1966 |
| WO | WO 00/37412 A1 | 6/2000 |
| WO | WO 03/076406 | 9/2003 |
| WO | WO 2005/023255 A2 | 3/2005 |
| WO | WO 2005/092832 A1 | 10/2005 |
| WO | 2006/084116 A2 | 8/2006 |
| WO | WO 2006/133848 A1 | 12/2006 |
| WO | WO 2007/096647 A2 | 8/2007 |
| WO | WO 2009/087238 A2 | 7/2009 |

OTHER PUBLICATIONS

Hui; Oncogene 2006, 25, 7305-7310.*
Levine; Nature Reviews Cancer 2009 9, 749-758.*
Suzuki; Bioorganic and Medicinal Chemistry 2009, 17, 5900-5905.*
Suzuki; ChemMedChem 2006, 1, 1059-1062.*
Goh; J Pathol 2011, 223, 116-126.*
Vousden; Cell 2009, 137, 413-431.*
Ohizumi; British Journal of Cancer (1995) 72, 1219-1223.*
Hulkower; Pharmaceutics 2011, 3, 107-124.*
Desilet; Curr. Issues Mol. Biol. 2010, 12, 143-146.*
Chaffer; Science 2011, 331, 1559-1564.*
Valastyan; Cell 2011, 147, 275-292.*
V. Peesapati et al., "Convenient Synthesis of Some Styrylpyridinium Dyes Containing Aminobis[benzenamine] Moiety," Indian Journal of Chemistry, vol. 35B, Mar. 1996, pp. 207-212.
Von Adolf Emil Siegrist, "Preparation of Styryl and Stilbenyl Derivatives of 1 H-Benzotriazoles," Helvetica Chimica Acta, vol. 64, 1981, No. 68, pp. 662-680 (with English-language Summary).
Jye-Shane Yang et al., "Origin of the N-methyl and N-phenyl Substituent Effects on the Fluorescence Vibronic Structures of trans-4-aminostilbene and its Derivatives in Hexane," Photochem. Photobiol. Sci., 2003, vol. 2, pp. 1225-1231.
Pakrashi et al; "Studies on 4-Quinazolinones. V. Reductive Ring Cleavage by Metal Hydrides;" J. Org. Chem.; Oct. 1972; vol. 37; No. 20; pp. 3143-3147.
Correa et al; "Novel Alternative for N—N Bond Formation through a PIFA-Mediated Oxidative Cyclization and Its Application to the Synthesis of Indazol-3-ones;" J. Org. Chem.; Jan. 2006; vol. 71; pp. 3501-3505.
Yamada et al; "4-Oxo-1,2,3,4-tetrahydroquinazolines. V. Ring Expansion Reaction of 1-Methyl-3-phenyl-4-oxo-3,4-dihydroquinazolinium Bromide with Diazoalkanes;" Bulletin of the Chemical Society of Japan; Feb. 1974; vol. 47 (2); pp. 339-340.
Katritzky et al; "Carbon Dioxide: A Reagent for the Simultaneous Protection of Nucleophilic Centres and the Activation of Alternative Locations to Electrophilic Attack. Part III. A New Synthetic Method for the ortho-Substitution of N-Monoalkylanilines;" Department of Chemistry, University of Florida; May 1986.
Okumura et al; "4-Oxo-1,2,3,4-tetrahydroquinazolines. II. Synthesis of 1-Alkyl-and 1-[2-(Disubstituted amino)ethyl]-2-methyl-3-

(56) References Cited

OTHER PUBLICATIONS aryl-4-oxo-1,2,3,4-tetrahydroquinazolines;" Chemical Research Laboratory, Tanabe Seiyaku Company, Ltd.; Jul. 1968; vol. 11; pp. 788-792.
Okumura et al; "4-Oxo-1,2,3,4-tetrahydroquinazolines. I. Syntheses and Pharmacological Properties of 2-methyl-3-aryl-4-oxo-1,2,3,4-tetrahydroquinazolines and Their 1-Acyl Derivatives;" Chemical Research Laboratory, Tanabe Seiyaku Company, Ltd.; Mar. 1968; vol. 11; pp. 348-352.
Gatta et al; "Su Alcune Reazioni Con Antranilammidi;" Il Farmaco-Ed. Sc.; 1970; vol. 25; No. 11; pp. 830-841.
Chesnokov, et al., "Synthesis and Biological Activity of Substituted Amides of 2-Aminonicotinic Acid," Perm Pharmaceutical Institute, Translated from Khimiko-Farmatsevticheskii Zhurnal, vol. 7, No. 11, pp. 20-23, Nov. 1973.
Cuffini, et al., "Nine N-aryl-2-choloronicotinamides: supramolecular structures in one, two and three dimensions,"Acta Crystallographica Section B, B62 pp. 651-665, 2006.
Jozwiak, et al., "Behaviour of N-Pyridylbenzamides versus Benzanilides in the ortho-Directed Lithiation of Masked Aromatic Carboxylic Acids," Eur. J. Org. Chem., pp. 3254-3261, 2004.
Kumar, et al., "Exploring hydrogen-bond capable backbone and ligating topologies: Co(II) coordination polymers derived from mixed ligand systems," Journal of Molecular Structure, 796, pp. 139-145, 2006.
Lam, et al., "α-Nitrogen activating effect in the room temperature copper-promoted N-arylation of heteroarylcarboxamides with phenyl siloxane or p-toluylboronic acid," Tetrahedron Letters 42, pp. 2427-2429, 2001.
Singha, et al., "$^1$H and $^{13}$C NMR spectral studies of conformation of some N-(2-pyridinyl)-3-pyridinecarboxamides," Journal of Molecular Structure, 449, pp. 91-98, 1998.
Sigova, et al., "Synthesis and Biological Activity of Arylamides of 2-Methylnicotinic and 2-Phenylindolizine-8-Carboxylic Acids," Perm Pharmaceutical Institute, Translated from Khimiko-Farmatsevticheskii Zhurnal, vol. 19, No. 3, pp. 159-163, Mar. 1985.
Prashad, et al., "A new reaction of N-aryl-2-pyrimidinamines with triphosgene," Tetrahedron Letters, 48, pp. 2087-2089, 2007.
Sep. 10, 2013 Search Report issued in French Patent Application No. FR 1350599 (with English translation).
Sep. 5, 2013 Search Report issued in French Patent Application No. 1350600 (with English Translation).
Nayak et al; "p53-Induced Apoptosis and Inhibitors of p53;" Current Medicinal Chemistry; 2009; vol. 16; pp. 2627-2640.
Hardcastle; "Inhibitors of the MDM2-p53 interaction as anticancer drugs;" Drugs of the Future; 2007; vol. 32; No. 10; pp. 883-896.
Aug. 3, 2011 Search Report issued in European Patent Application No. EP 11 305385.
Sep. 28, 2012 Search Report issued in International Patent Application No. PCT/IB2012/051603.
Sep. 28, 2012 Written Opinion issued in International Patent Application No. PCT/IB2012/051603.
Lourenco et al; "Evaluation of anti-tubercular activity of nicotinic and isoniazid analogues;" Arkivoc; 2007; pp. 181-191.
Park et al; "Photoreaction of 2-Halo-N-pyridinylbenzamide: Intramolecular Cyclization Mechanism of Phenyl Radical Assisted with n-Complexation of Chlorine Radical;" J. Org. Chem. 2001; vol. 66; pp. 2197-2206.
Sep. 5, 2013 Office Action issued in Japanese Patent Application No. 2010-541800 (with translation).
Sorenson; "Selective N-Arylation of Aminobenzanilides under Mild Conditions Using Triarylbismuthanes;" J. Org. Chem.; 2000; vol. 65; pp. 7747-7749.
Coyne et al; "3,4-Dihydro-2(1H)-quinazolinones;" Journal of Medicineal Chemistry; 1968; vol. 11; No. 6; pp. 1208-1218.
Huang et al; "Expanding Pd-Catalyzed C—N Bond-Forming Processes: The First Amidation of Aryl Sulfonates, Aqueous Amination, and Complementarity with Cu-Catalyzed Reactions;" J. Am. Chem. Soc.; 2003; vol. 125; No. 22; pp. 6653-6655.

Shankaran et al; "Silicon in Benzamide Directed Ortho Metalation, Formation and Reactions of Benzamide Benynes;" Tetrahedron Letters; 1984; vol. 25; No. 27; pp. 2827-2830.
Peet et al; "A Novel Oxamide Rearrangement;" J. Heterocyclic Chem.; 1980; vol. 17; pp. 1513-1518.
Ward et al; "Solid Phase Synthesis of Aryl Amines Palladium Catalyzed Amination of Resin-Bound Aromatic Bromides;" Tetrahedron Letters; 1996; vol. 37; No. 39; pp. 6993-6996.
Elter et al; "Über das 9-Methyl-3-carbolin and das 6-Methly-3-carbolin;" Monatshefte Fuer Chemie; 1950; vol. 81; pp. 404-413.
Gennarro; "Pyrido[3,2-b][1,4]benzothiazine (1-Azaphenothiazinc);" J. Og. Chem.; 1959; vol. 24; pp. 1156-1157.
Chemical Abstracts Service; "Aminopyridines;" XP-002499122; 1966.
Tazi et al; "The spliceosome: a novel multi-faceted target for therapy;" Trends in Biochemical Sciences; Aug. 2005; vol. 30; No. 8; pp. 494-478.
Jul. 26, 2010 Written Opinion issued in International Patent Application No. PCT/EP2009/050280.
Jul. 26, 2010 Search Report issued in International Patent Application No. PCT/EP2009/050280.
Ito et al; "A medium-term rat liver bioassay for rapid in vivo detection of carcinogenic potential of chemicals;" Cancer Sci; Jan. 2003; vol. 94; No. 1; pp. 3-8.
Yang et al; "Photoinduced Single- versus Double-Bond Torsion in Donor-Accepted-Substituted trans-Stilbenes;" J. Phys. Chem. A; 2006; vol. 110; pp. 8003-8010.
Aug. 24, 2012 Office Action issued in U.S. Appl. No. 12/811,931.
Jan. 1, 2013 Office Action issued in U.S. Appl. No. 12/811,931.
Aug. 5, 2013 Notice of Allowance issued in U.S. Appl. No. 12/811,931.
Jul. 10, 2013 Office Action issued in Chinese Patent Application No. 20098010636.1 (English-language translation only).
U.S. Appl. No. 12/811,931, filed Aug. 30, 2010.
U.S. Appl. No. 14/070,799, filed Nov. 4, 2013.
Apr. 6, 2015 Office Action issued in U.S. Appl. No. 14/070,799.
Mar. 1, 2017 Office Action issued in U.S Appl. No. 14/958,602.
Lee et al., "Prognostic Significance of the Co-expression of RON and MET Receptors in Node-Negative Breast cancer Patients," Clinical Cancer Research. vol. 11, pp. 2222-2228, Mar. 15, 2005.
Lee, "Synthesis of 1-Methyl-3H-1, 4-benzodiazepine-2,5(1H,4H)-dione and Derivatives," Organic Chemistry Department, Research Division Abott Laboratories, vol. 1, Dec. 1964, pp. 235-238.
Sigova et al., "Synthesis and Biological Activity of Arylamides of 2-Methylnicotinic and 2-Phenylindolizine-8-Carboxylic Acids," pp. 174-177, Plenum Publishing Corporation, 1986.
Ikawa et al., "Pd-Catalyzed Amidations of Aryl Chlorides Using Monodentate Biaryl Phosphine Ligands: A Kinetic, Computational, and Synthetic Investigation," Journal of American Chemical Society, vol. 129, No. 43, 2007, pp. 13001-13007.
Ernst et al., "Design and Application of an [alpha]-Helix-Mimetic Scaffold Based on an Oligoamide-Foldamer Strategy; Antagonism of the Bak BH3/BcI-xL Complex,"Angew. Chem. Int. Ed., vol. 42, No. 5, 2003, pp. 535-539.
Cativiela et al., "A Convenient Synthesis of N-Aryl-1,2-dihydro-2-oxo-3-pyridinecarbox-amides, N-Aryl-N-methyl-1,2-dihydro-2-oxo-3-pyridinecarboxamides and Their 1-Methyl (O-Methyl)-Derivatives," J. Heterrocylic Chem., vol. 19, pp. 1093-1097, 1982.
Chesnokov et al., "Investigation of Naphthyridines IV, Arylamides of 2-Anilinonicotinic Acid and Cyclization of Them to 4-Arylamino-2,3-Benzo-1,8-Naphthyridines," Plenum Publishing Corporation, 1975, pp. 217-218.
Yang et al., "Meta Conjugation Effect on the Torsional Motion of Aminostilbenes in the Photoinduced Intramolecular Charge-Transfer State," Journal of American Chemical Society, No. 129, pp. 13183-13192, 2007.
Berthiol et al., "Heck reaction with heteroaryl halides in the presence of a palladium-tetraphosphine catalyst," Tetrahedron Letters 43, pp. 5625-5628, 2002.
Majima et al., "Cis-Trans Isomerization and Oxidation of Radical Cations of Stilbene Derivatives," Journal of Organic Chemistry, vol. 61, No. 22, pp. 7793-7800, 1996.

(56) References Cited

OTHER PUBLICATIONS

Nov. 18, 2016 Office Action issued in European Patent Application No. 09 700 499.8.
Dec. 1, 2017 Office Action issued in U.S. Appl. No. 14/958,602.

* cited by examiner

COMPOUNDS FOR USE AS THERAPEUTIC AGENTS AFFECTING P53 EXPRESSION AND/OR ACTIVITY

FIELD OF THE INVENTION

The present invention is generally dedicated to compounds for use as therapeutic agents affecting p53 expression and/or activity.

BACKGROUND OF THE INVENTION p53 is a house-keeping protein, the activity and expression of which, as well as its cellular pathway, are critically implied in the maintaining of cell homeostasis, and the occurrence of numerous diseases. Indeed, numerous diseases may result from a deregulation of p53, either in its expression, or in its activity or cellular pathway, including its activating factors or its target genes.

The p53 gene is the most frequently mutated gene in cancers. Its tumour suppressor activity relies on its ability to control proliferation by inducing apoptosis, cell cycle arrest and senescence in response to cellular stresses, such as DNA damages. Almost all human cancer exhibit defects in p53 activation either by p53 gene mutation which occurs in around 50% of human cancers, or by the failure (shortcoming) of the pathways promoting its activation.

The p53 pathway is also implicated in other diseases such as inflammation, fibrosis, neurodegenerative diseases, ischemia, atherosclerosis, pathogenesis of a number of hepatic disorders, such as cholestasis, autoimmune diseases, ethanol-induced injuries such as alcoholic liver diseases (ALD) including fatty liver, alcoholic hepatitis and cirrhosis, ribosome biogenesis disorders such as Treacher Collins syndrome (TCS), male infertility, alopecia, neurological defects, endocrinopathy syndrome (ANE syndrome), Shwachman-Diamond syndrome (SDS) and neurofibromatosis type 1 (NF1), and HIV-associated pathologies such as dementia, diabetes and myocardial infarction.

Indeed, in diseases other than cancer, the inhibition of wild-type p53 may represent a new therapeutic strategy. Thus, inhibition of p53 activity or cellular pathway might be highly beneficial in the prevention of injury to diverse organs (Georgiev et al., Curr Pharm Des, 2006 12:2911), or in treatment of myocardial infarction (Matsusaka et al., 2006). Also, ischemia, or diseases associated with neurodegenerative pathological conditions, including AIDS-associated neurodegeneration, stroke, Parkinson's, Alzheimer's, and Huntington's diseases (Vousden & Lane, 2007, Nat Rev Mol Cell Biol. 2007 April; 8(4):275-83), clinical management of hepatic disease induced by toxic bile salts (Oh et al., 2002 Toxicol Appl Pharmacol. 2002 Jul. 1; 182(1):27-33), or atherosclerosis in which wild-type p53 is over-expressed (Iacopetta et al., Int J Oncol, 1995, 7, 399-402), may benefit from compounds able to curb deregulated p53.

Document WO2009/087238 discloses compounds effective in treating diseases related to the splicing process.

Up to now, to the knowledge of the inventors, no drug repressing mutated p53 expression has been described. Indeed activation of p53 pathway is generally obtained but no reduction of p53 pathway.

Therefore, there is an existing need to find out compounds able to compensate deregulated p53 expression, activity, or cellular pathway.

More particularly, there is a need to identify new compounds able to inhibit or reduce the expression of mutated p53 isoforms, preferably without affecting the expression of wild-type p53 isoforms.

There is a need to have compounds able to favour the expression of non-mutated p53 isoforms over mutated p53 isoforms.

There is also a need to have compounds able to modulate the p53 gene expression, and in particular able to specifically modulate the splicing of p53 isoforms.

There is also a need to have compounds able to prevent or reduce over expression of wild-type isoform(s) of p53.

There is also a need to have compounds able to prevent or increase low-expression of wild-type isoform(s) of p53.

More precisely, there is a need to find out compounds able to prevent, inhibit and/or treat a disease in a patient suffering thereof, said disease involving deregulated p53.

More particularly, there is a need to have compounds able to prevent, inhibit and/or treat a disease in a patient suffering thereof, said disease involving mutated p53, and/or deregulated wild-type p53.

More particularly, there is a need to have compounds able to prevent, inhibit and/or treat a cancer in a patient suffering thereof, said cancer involving a mutated p53 or deregulated wild-type p53, such as a low-expression of wild-type p53.

There is a need to have compounds able to prevent, inhibit and/or treat atherosclerosis in a patient suffering thereof, said atherosclerosis involving a mutated p53, or a deregulated wild-type isoform of p53, such as a low-expression of wild-type p53.

There is also a need to have compounds able to prevent, inhibit and/or treat a disease in a patient suffering thereof, said disease involving a deregulated wild-type p53, such as a disease chosen from inflammation, fibrosis, neurodegenerative diseases, ischemia, atherosclerosis, hepatic disorders, such as cholestasis, autoimmune diseases, and ethanol-induced injuries such as alcoholic liver diseases (ALD) including fatty liver, alcoholic hepatitis and cirrhosis, ribosome biogenesis disorders such as Treacher Collins syndrome (TCS), male infertility, alopecia, neurological defects, endocrinopathy syndrome (ANE syndrome), Shwachman-Diamond syndrome (SDS) and neurofibromatosis type 1 (NF1), and HIV-associated pathologies such as dementia, diabetes and myocardial infarction.

SUMMARY OF THE INVENTION

It has now been found that derivatives of formula (I) as defined hereinafter, which are partially described in document WO 2009/087238, are able to modulate the p53 expression and/or activity with a discriminating effect over wild-type and mutated p53, as well as at isoforms level, as illustrated in the experimental data hereinafter.

More particularly, said derivatives are able to inhibit the expression of mutated p53 and/or to modulate the expression of wild-type p53. Through their ability to modulate the expression of mutated p53 and possibly wild-type p53, specifically at an isoform level, i.e. short or long, the compounds of the invention are also advantageously able to modulate the activity or cellular pathway of those proteins, and in particular to affect the p53-dependent expression of target genes, such as Bcl2, Hdm2 or p21. Accordingly, the derivatives of the invention are able to curb a deregulated p53 expression, activity or cellular pathway.

The derivatives of formula (I) as described hereinafter are moreover able to exert a specific action on the short (truncated) or long isoform of p53.

Said compounds can selectively act on tumours involving a mutated p53. In other words, said compounds are particularly useful for treating patients affected by cancer and/or atherosclerosis involving a mutated p53, and more particularly expression of a mutated p53.

Also, the compounds of the invention are able to curb the expression, activity or cellular pathway of wild-type p53, more particularly in cells where wild-type p53 is overexpressed.

On the basis of such activity, the compounds are useful in the prevention, inhibiting and/or treatment of a disease involving a deregulated p53, such as a mutated p53 or a deregulated wild-type p53's pathway. In particular, the compounds of the invention are useful for preventing and/or treating cancer and/or atherosclerosis involving a mutated p53, and/or a deregulated wild-type p53, as well as for preventing, inhibiting and/or treating diseases involving a deregulated wild-type p53, such as inflammation, fibrosis, neurodegenerative diseases, ischemia, atherosclerosis, pathogenesis of a number of hepatic disorders, such as cholestasis, autoimmune diseases, and ethanol-induced injuries such as alcoholic liver diseases (ALD) including fatty liver, alcoholic hepatitis and cirrhosis, ribosome biogenesis disorders such as Treacher Collins syndrome (TCS), male infertility, alopecia, neurological defects, endocrinopathy syndrome (ANE syndrome), Shwachman-Diamond syndrome (SDS) and neurofibromatosis type 1 (NF1), and HIV-associated pathologies such as dementia, diabetes and myocardial infarction.

The compounds of the invention may be useful in the prevention and/or treatment of cancer involving a mutated p53.

More particularly the compounds are useful in the prevention and treatment of primary breast cancer, axillary node metastasis, HER2 positive and ER negative cancers with poor prognosis, and diseases involving a mutated p53, and in particular involving Δ133p53β isoform, and more particularly breast cancer and colon cancer.

The present invention therefore relates to compounds of formula (I) as defined below for use in a method for preventing, inhibiting or treating cancer and/or atherosclerosis in patients expressing a mutated p53, or inflammation, fibrosis, neurodegenerative diseases, ischemia, atherosclerosis, pathogenesis of a number of hepatic disorders such as cholestasis, autoimmune diseases and ethanol-induced injuries such as alcoholic liver diseases (ALD) including fatty liver, alcoholic hepatitis and cirrhosis, ribosome biogenesis disorders such as Treacher Collins syndrome (TCS), male infertility, alopecia, neurological defects, endocrinopathy syndrome (ANE syndrome), Shwachman-Diamond syndrome (SDS) and neurofibromatosis type 1 (NF1), and HIV-associated pathologies such as dementia, diabetes and myocardial infarction in patients in which wild-type of p53 is deregulated.

The neurodegenerative diseases more particularly considered may be chosen from AIDS-associated neurodegeneration, stroke, Parkinson's, Alzheimer's, and Huntington's diseases.

The present invention moreover relates to a method of preventing, inhibiting or treating diseases involving a deregulated p53, in particular a mutated p53 or a deregulated wild-type p53.

More particularly, the invention relates to a method for preventing, inhibiting or treating a cancer in patients said cancer involving a mutated p53, or a disease chosen from fibrosis, neurodegenerative diseases, ischemia, cholestasis or atherosclerosis in patients, said disease involving deregulation of expression, activity or pathway of wild-type p53, which comprises at least one step consisting in administering to a patient suffering thereof an effective amount of a compound as defined in formula (I) below or one of its pharmaceutically acceptable salts.

The present invention further relates to some particular derivatives as such, as defined below.

The present invention also provides pharmaceutical compositions comprising at least one of said particular compounds.

DETAILED DESCRIPTION OF THE INVENTION

According to a first aspect, a subject-matter of the present invention relates to a compound of formula (I)

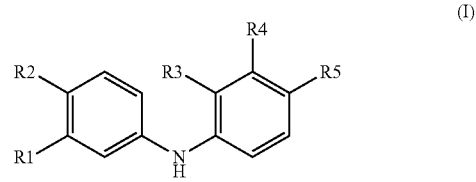

wherein:
R1 and R2 independently represent
a hydrogen atom, a $(C_1-C_4)$alkoxy group, a fluoro$(C_1-C_4)$alkoxy group, a hydroxyl group, a benzyloxy group, a di$(C_1-C_4)$alkylamino group,
a pyridyl-vinyl or pyrimidinyl-vinyl group, said two groups being optionally substituted by a halogen atom, a $(C_1-C_4)$alkyl group or a fluoro$(C_1-C_4)$alkyl group,
a styryl group optionally substituted by a $(C_1-C_4)$alkoxy group or a fluoro$(C_1-C_4)$alkoxy group,
a —NHCOphenyl group, the phenyl group being optionally substituted by a $(C_1-C_4)$alkoxy group or a fluoro $(C_1-C_4)$alkoxy group,
R3, R4 and R5 independently represent
a hydrogen atom, a $(C_1-C_4)$alkyl group,
a —CONHR6 group,
a —CONR7R8 group,
a —SO$_2$NHR6 group,
a heteroaryl group optionally substituted by a halogen atom, a —$(CH_2)_n$NR7R8 group or a hydroxy$(C_1-C_4)$ alkyl group,
R6 represents a hydrogen atom, a —$(CHR9)_m$ $(CH_2)_n$NR7R8 group or a $(C_1-C_6)$alkyl group optionally substituted by a hydroxyl group,
R7 and R8 independently represent a $(C_1-C_4)$alkyl group or form together with the nitrogen atom to which they are attached a saturated or insaturated 5- or 6-membered ring optionally containing a further heteroatom chosen among nitrogen and oxygen, said ring being optionally substituted by a $(C_1-C_4)$alkyl group,
R9 represents a $(C_1-C_2)$alkyl group,
m is 0 or 1,
n is 1, 2, 3, 4 or 5,
provided that two of R3, R4 and R5 are a hydrogen atom or a $(C_1-C_4)$alkyl group and the last is different from a hydrogen atom or a $(C_1-C_4)$alkyl group, and
or anyone of its pharmaceutically acceptable salt,
for use in a method for preventing, inhibiting or treating a disease in a patient suffering thereof, said disease involving a deregulated p53.

Within the invention, "a disease involving a deregulated p53" intends to encompass diseases where at least one isoform of p53, a, 13 or 7, full-length or truncated (short), has its expression, activity or cellular pathway altered, namely suppressed, reduced or increased.

The expression of p53 may be altered at a gene, mRNA and/or protein level.

The expression and/or activity and/or cellular pathway of p53 may be altered by a presence of a mutation in p53 or by an alteration of its activating factors.

The activity or the cellular pathway of p53 may be assessed by determination of the expression level of downstream target genes, such as Hdm-2, p21, Bcl-2 or Bax.

In one embodiment, a disease involving a deregulated p53 may be chosen from a disease involving a mutated p53 or a disease involving a deregulated wild-type p53.

Within the invention, "mutated p53" intends to encompass mutation in the p53 gene resulting either in a decrease or absence of p53 protein expression, or in an increase of p53 protein expression, or in expression of a mutated p53 protein exhibiting reduced, suppressed or increased wild-type activity. The alteration of expression and/or activity of mutated p53 may affect the whole family of p53, or only one isoform, or at least one isoform. Preferably, a mutated p53 relates to at least one mutated isoform of p53, such as an isoform chosen from α, β or γ, truncated or full-length.

Preferably, the invention relates to diseases involving mutated p53. In particular, diseases involving mutated p53 exhibit reduced or suppressed activity and/or expression of the mutated p53. More particularly such diseases may be chosen from cancer and/or atherosclerosis. In one embodiment, the invention relates more particularly to a cancer involving at least one mutated isoform of p53, preferably Δ133p53, and in particular a β and/or γ isoform(s).

According to another embodiment, the invention relates to diseases involving a deregulated wild-type p53. A "deregulated wild-type p53" encompasses suppressed, reduced or increased expression of wild-type p53, or suppressed, reduced or increased activity or cellular pathway of wild-type p53. "Wild-type p53" intends to relate to at least one isoform of p53, such as chosen from α, β or γ, truncated or full-length.

Preferably, diseases involving a deregulated wild-type p53 may be chosen from inflammation, fibrosis, neurodegenerative diseases, ischemia, atherosclerosis, hepatic disorders, such as cholestasis, autoimmune diseases, ethanol-induced injuries such as alcoholic liver diseases (ALD) including fatty liver, alcoholic hepatitis and cirrhosis, ribosome biogenesis disorders such as Treacher Collins syndrome (TCS), male infertility, alopecia, neurological defects, endocrinopathy syndrome (ANE syndrome), Shwachman-Diamond syndrome (SDS) and neurofibromatosis type 1 (NF1), and HIV-associated pathologies such as dementia, diabetes and myocardial infarction.

In one embodiment, the instant invention relates to a compound of formula (I) for use in a method for preventing, inhibiting or treating cancer, inflammation, fibrosis, neurodegenerative diseases, ischemia, atherosclerosis, hepatic disorders, cholestasis, atherosclerosis, autoimmune diseases, ethanol-induced injuries such as alcoholic liver diseases (ALD) including fatty liver, alcoholic hepatitis and cirrhosis, ribosome biogenesis disorders such as Treacher Collins syndrome (TCS), male infertility, alopecia, neurological defects, endocrinopathy syndrome (ANE syndrome), Shwachman-Diamond syndrome (SDS) and neurofibromatosis type 1 (NF1), and HIV-associated pathologies such as dementia, diabetes and myocardial infarction.

In a preferred embodiment, the invention relates to a compound of formula (I) as above-defined as an agent for preventing, inhibiting or treating a cancer in a patient exhibiting a mutated p53, or fibrosis, neurodegenerative diseases, ischemia, cholestasis or atherosclerosis in a patient exhibiting a deregulated wild-type p53.

The term "preventing", as used herein, means reducing the risk of onset or slowing the occurrence of a given phenomenom, namely in the present invention, a disease involving a deregulated p53 such as cancer, inflammation, fibrosis, neurodegenerative diseases, ischemia, atherosclerosis, hepatic disorders, cholestasis, atherosclerosis, autoimmune diseases, ethanol-induced injuries such as alcoholic liver diseases (ALD) including fatty liver, alcoholic hepatitis and cirrhosis, ribosome biogenesis disorders such as Treacher Collins syndrome (TCS), male infertility, alopecia, neurological defects, endocrinopathy syndrome (ANE syndrome), Shwachman-Diamond syndrome (SDS) and neurofibromatosis type 1 (NF1), and HIV-associated pathologies such as dementia, diabetes and myocardial infarction.

The pyridyl-vinyl group can be a 4-pyridyl-vinyl group, a 3-pyridyl-vinyl group or a 2-pyridyl-vinyl group and preferably a 4-pyridyl-vinyl group or a 2-pyridyl-vinyl.

When R7 and R8 form together with the nitrogen atom to which they are attached a saturated or insaturated 5- or 6-membered ring, said ring may preferably be a imidazolyl, a morpholinyl, a piperidinyl, a pyrrolidinyl or 4-methylpiperazinyl group.

According to one embodiment, the present invention relates to a compound of formula (I) as defined above, wherein one of R1 and R2 is a hydrogen atom and the other is different from a hydrogen atom, for use in a method for preventing, inhibiting or treating a disease in a patient suffering thereof, said disease involving deregulated p53.

According to another embodiment, the present invention relates to a compound of formula (I) as defined above, wherein R3 represents a hydrogen atom and one of R4 and R5 is a —CONHR6 group or a heteroaryl group optionally substituted by a —(CH$_2$)$_n$NR7R8 group or a hydroxy(C$_1$-C$_4$)alkyl group, wherein R6, R7, R8, R9 and n are as defined above, for use in a method for preventing, inhibiting or treating disease in a patient suffering thereof, said disease involving deregulated p53.

According to another embodiment, the present invention relates to a compound of formula (I)
wherein:
R1 and R2 independently represent
a hydrogen atom, a methoxy group, a trifluoromethoxy group, a hydroxyl group, a benzyloxy group, a dimethylamino group,
a pyridyl-vinyl or pyrimidinyl-vinyl group, said two groups being optionally substituted by a halogen atom, a methoxy group or a trifluoromethyl group,
a styryl group optionally substituted by a methoxy group or a trifluoromethoxy group,
a —NHCOphenyl group, the phenyl group being optionally substituted by a methoxy group or a trifluoromethoxy group,
R3, R4 and R5 independently represent
a hydrogen atom, a methyl group,
a —CONHR6 group,
a —CONR7R8 group,
a —SO$_2$NHR6 group, or
a triazolyl or imidazolyl group, said group being optionally substituted by a chlorine atom, a —(CH$_2$)$_n$NR7R8 group or a hydroxy(C$_1$-C$_4$)alkyl group, R6 represents a hydrogen atom, a —(CHR9)$_m$(CH$_2$)$_n$NR7R8 group or a (C$_1$-C$_6$)alkyl group optionally substituted by a hydroxyl group, R7 and R8 independently represent a (C$_1$-C$_4$)alkyl group or form together with the nitrogen atom to which they are attached a saturated or insaturated 5- or 6-membered ring optionally containing a further heteroatom chosen among nitrogen and oxygen, said ring being optionally substituted by a methyl group, and said ring being chosen among a imidazolyl, a morpholinyl, a piperidinyl, a pyrrolidinyl or 4-methylpiperazinyl group, R9 represents a (C$_1$-C$_2$)alkyl group, m is 0 or 1, n is 1, 2 or 3, provided that two of R3, R4 and R5 are a hydrogen atom or a methyl group and the last is different from a hydrogen atom or a methyl group and that one of R1 and R2 is a hydrogen atom and the other is different from a hydrogen atom, and or anyone of its pharmaceutically acceptable salt, for use in a method for preventing, inhibiting or treating a disease in a patient suffering thereof, said disease involving deregulated p53.

The compound of formula (I) in any embodiment as described above is more particularly useful as an agent for preventing, inhibiting or treating a disease in a patient, wherein the disease involves mutated p53 or altered wild-type p53 expression, activity or pathway.

In the context of the present invention, the term "patients suffering from diseases involving a mutated p53 gene or an altered wild-type p53 expression, activity or pathway" means a specific group of patients for which it has been detected by known methods, for example sequencing or immunodetection of mutated or wild-type p53 isoform(s) or methods aiming at assessing the expression, activity or pathway of p53, such as the assessment of p53 targets (Bcl-2, Hdm-2 or p21 . . . ), that p53 mutation(s) exists or a mutated p53 is expressed or that the expression, activity or cellular pathway of wild-type p53 is altered.

The compound of formula (I) in any embodiment as described above is more particularly useful as an agent for preventing, inhibiting or treating a disease in a patient wherein the disease involves an altered expression of wild-type p53, such as a low- or an over-expression, and in particular an over-expression.

The compounds of the invention may exist in the form of free bases or of addition salts with pharmaceutically acceptable acids.

Suitable physiologically acceptable acid addition salts of compounds of formula (I) include hydrobromide, tartrate, citrate, trifluoroacetate, ascorbate, hydrochloride, tartrate, triflate, maleate, mesylate, formate, acetate and fumarate.

The compounds of formula (I) and or salts thereof may form solvates (e.g. hydrates) and the invention includes all such solvates.

The terms "hydrates" and "solvates" simply mean that the compounds (I) according to the invention can be in the form of a hydrate or a solvate, i.e. combined or associated with one or more water or solvent molecules. This is only a chemical characteristic of such compounds, which can be applied for all organic compounds of this type.

In the context of the present invention, the term:

"halogen" is understood to mean chlorine, fluorine, bromine, or iodine, and in particular denotes chlorine, fluorine or bromine, "(C$_1$-C$_4$)alkyl" as used herein respectively refers to C$_1$-C$_4$ normal, secondary or tertiary saturated hydrocarbon. Examples are, but are not limited to, methyl, ethyl, 1-propyl, 2-propyl, "(C$_1$-C$_4$)alkoxy" as used herein respectively refers to —O—(C$_1$-C$_4$)alkyl moiety, wherein alkyl is as defined above. Examples are, but are not limited to, methoxy, ethoxy, 1-propoxy, 2-propoxy, "fluoroalkyl group" and "fluoroalkoxy group" refers respectively to alkyl group and alkoxy group as above-defined, said groups being substituted by at least one fluorine atom. Examples are perfluoroalkyl groups, such as trifluoromethyl, or perfluoropropyl or perfluoroalkoxy groups, such as trifluoromethoxy, "heteroaryl" group refers to an aromatic ring, where the ring structure is formed by 3 to 5 carbon atoms and by one to three hetereoatoms chosen among N, O or S. When the heteroaryl group is substituted, said heteroaryl group further bears one or more substituents. The following heteroaryl may be cited: thienyl, furyl, pyrrolyl, imidazolyl, pyrazolyl, pyridyl, pyrazinyl, pyrimidinyl, pyridazinyl, triazolyl, and preferably triazolyl and imidazolyl, and "patient" may extend to humans or domestic mammals or mammals of any economic value, such as cats or dogs.

According to a particular embodiment, an additional subject-matter of the present invention is a compound of formula (Iab)

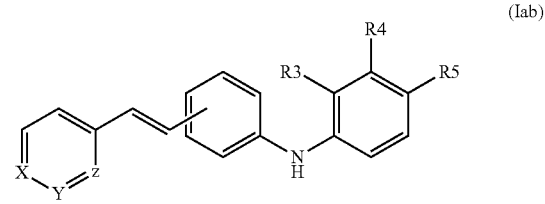

(Iab)

wherein:

X, Y and Z are independently C or N,

R3, R4 and R5 are as defined above in anyone of the embodiments of formula (I), provided that the lateral group

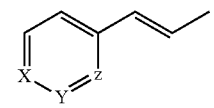

is in the meta or para position with respect to the —NH— group, and preferably in the meta position, provided that at most two of X, Y and Z are N, and that when Y is N, X and Z are C, and provided that two of R3, R4 and R5 are a hydrogen atom or a (C$_1$-C$_4$)alkyl group and the last is different from a hydrogen atom or a (C$_1$-C$_4$)alkyl group, or one of its pharmaceutically acceptable salt, for use in a method for preventing, inhibiting or treating a disease in a patient suffering thereof, said disease involving deregulated p53.

According to a more particular aspect of said embodiment, an additional subject-matter of the present invention is a compound of formula (Iab)

wherein:
R3 is hydrogen or a methyl group,
one of R4 and R5 represents
a —CONHR6 group, or
a triazolyl group being optionally substituted by a —(CH$_2$)$_n$NR7R8 group or a hydroxy(C$_1$-C$_4$)alkyl group,
R6 represents a (C$_1$-C$_6$)alkyl group or a —(CH$_2$)$_n$NR7R8 group,
R7 and R8 independently represent a (C$_1$-C$_4$)alkyl group or form together with the nitrogen atom to which they are attached a saturated or insaturated 5- or 6-membered ring optionally containing a further heteroatom chosen among nitrogen and oxygen, said ring being optionally substituted by a methyl group, and said ring being chosen among a imidazolyl, a morpholinyl, a piperidinyl, a pyrrolidinyl or 4-methylpiperazinyl group,
n is 1, 2 or 3,
and the other of R4 and R5 is a hydrogen atom,
or one of its pharmaceutically acceptable salt,
for use in a method for preventing, inhibiting or treating a disease in a patient suffering thereof said disease involving deregulated p53.

According to another particular embodiment, an additional subject-matter of the present invention is a compound of formula (Ia)

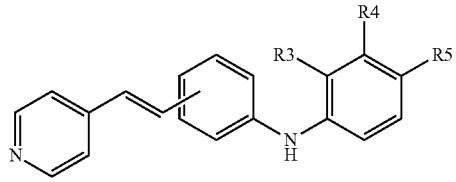

(Ia)

wherein:
R3, R4 and R5 are as defined above in anyone of the embodiments of formula (I),
provided that the lateral group

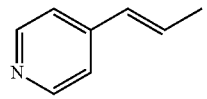

is in the meta or para position with respect to the —NH— group, and preferably in the meta position, and
provided that two of R3, R4 and R5 are a hydrogen atom or a (C$_1$-C$_4$)alkyl group and the last is different from a hydrogen atom or a (C$_1$-C$_4$)alkyl group,
or one of its pharmaceutically acceptable salt,
for use in a method for preventing, inhibiting or treating a disease in a patient suffering thereof, said disease involving deregulated p53.

According to a more particular aspect of said embodiment, an additional subject-matter of the present invention is a compound of formula (Ia)
wherein:
R3 is hydrogen or a methyl group,
one of R4 and R5 represents
a —CONHR6 group
a SO$_2$NHR6 group,
a CONR7R8 group, or
a triazolyl group being optionally substituted by a —(CH$_2$)$_n$NR7R8 group or a hydroxy(C$_1$-C$_4$)alkyl group,
R6 represents a hydrogen atom, a (C$_1$-C$_6$)alkyl group or a —(CH$_2$)$_n$NR7R8 group,
R7 and R8 independently represent a (C$_1$-C$_4$)alkyl group or form together with the nitrogen atom to which they are attached a saturated or insaturated 5- or 6-membered ring optionally containing a further heteroatom chosen among nitrogen and oxygen, said ring being optionally substituted by a methyl group, and said ring being chosen among a imidazolyl, a morpholinyl, a piperidinyl, a pyrrolidinyl or 4-methylpiperazinyl group,
n is 1, 2 or 3,
and the other of R4 and R5 is a hydrogen atom,
or one of its pharmaceutically acceptable salt,
for use in a method for preventing, inhibiting or treating a disease in a patient suffering thereof, said disease involving a deregulated p53.

According to another particular embodiment, an additional subject-matter of the present invention is a compound of formula (Ib)

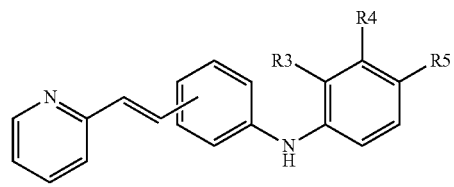

(Ib)

wherein:
R3, R4 and R5 are as defined above in anyone of the embodiments of formula (I),
provided that the lateral group

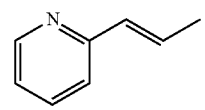

is in the meta or para position with respect to the —NH— group, and preferably in the meta position, and
provided that two of R3, R4 and R5 are a hydrogen atom or a (C$_1$-C$_4$)alkyl group and the last is different from a hydrogen atom or a (C$_1$-C$_4$)alkyl group,
or one of its pharmaceutically acceptable salt,
for use in a method for preventing, inhibiting or treating a disease in a patient suffering thereof, said disease involving a deregulated p53.

According to a more particular aspect of said embodiment, an additional subject-matter of the present invention is a compound of formula (Ib)
wherein:
R3 is hydrogen or a methyl group,
one of R4 and R5 represents
a —CONHR6 group, or
a triazolyl group being optionally substituted by a —(CH$_2$)$_n$NR7R8 group or a hydroxy(C$_1$-C$_4$)alkyl group,
R6 represents a (C$_1$-C$_6$)alkyl group or a —(CH$_2$)$_n$NR7R8 group, R7 and R8 independently represent a $(C_1-C_4)$alkyl group or form together with the nitrogen atom to which they are attached a saturated or insaturated 5- or 6-membered ring optionally containing a further heteroatom chosen among nitrogen and oxygen, said ring being optionally substituted by a methyl group, and said ring being chosen among a imidazolyl, a morpholinyl, a piperidinyl, a pyrrolidinyl or 4-methylpiperazinyl group, n is 1, 2 or 3, and the other of R4 and R5 is a hydrogen atom, or one of its pharmaceutically acceptable salt, for use in a method for preventing, inhibiting or treating a disease in a patient suffering thereof, said disease involving a deregulated p53.

According to another particular embodiment, an additional subject-matter of the present invention is a compound of formula (Ic)

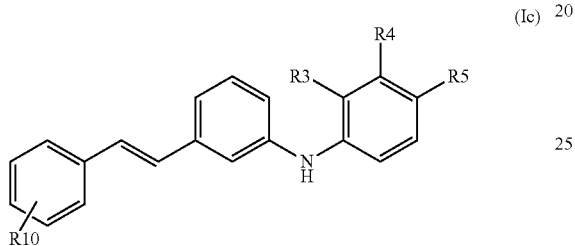

wherein:

R10 is a hydrogen atom, a $(C_1-C_4)$alkoxy group or a fluoro$(C_1-C_4)$alkoxy group, R3, R4 and R5 are as defined above in anyone of the embodiments of formula (I), provided that two of R3, R4 and R5 are a hydrogen atom or a $(C_1-C_4)$alkyl group and the last is different from a hydrogen atom or a $(C_1-C_4)$alkyl group, or one of its pharmaceutically acceptable salt, for use in a method for preventing, inhibiting or treating a disease in a patient suffering thereof, said disease involving a deregulated p53.

According to a more particular aspect of said embodiment, an additional subject-matter of the present invention is a compound of formula (Ic)

wherein:

R10 is a hydrogen atom, a methoxy group or a trifluoromethoxy group,

R3 is hydrogen or a methyl group, one of R4 and R5 represents a —CONHR6 group,

R6 represents a $(C_1-C_6)$alkyl group or a —$(CH_2)_n$NR7R8 group,

R7 and R8 independently represent a $(C_1-C_4)$alkyl group or form together with the nitrogen atom to which they are attached a saturated or insaturated 5- or 6-membered ring optionally containing a further heteroatom chosen among nitrogen and oxygen, said ring being optionally substituted by a methyl group, and said ring being chosen among a imidazolyl, a morpholinyl, a piperidinyl, a pyrrolidinyl or 4-methylpiperazinyl group, n is 1, 2 or 3, and the other of R4 and R5 is a hydrogen atom, or one of its pharmaceutically acceptable salt, for use in a method for preventing, inhibiting or treating diseases a disease in a patient suffering thereof, said disease involving a deregulated p53.

According to another particular embodiment, an additional subject-matter of the present invention is a compound of formula (Id)

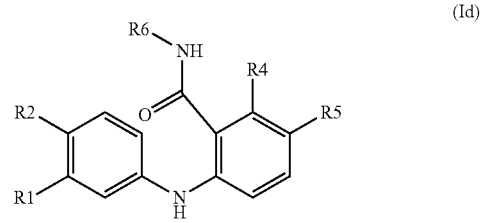

wherein:

R1, R2 and R6 are as defined above in anyone of the embodiments of formula (I),

R4 and R5 are independently a hydrogen atom or a $(C_1-C_4)$alkyl group, or one of its pharmaceutically acceptable salt, for use in a method for preventing, inhibiting or treating a disease in a patient suffering thereof, said disease involving a deregulated p53.

According to a more particular aspect of said embodiment, an additional subject-matter of the present invention is a compound of formula (Id)

wherein:

R1 and R2 independently represent a hydrogen atom, a methoxy group, a trifluromethoxy group, a hydroxyl group, a benzyloxy group or a dimethylamino group, R6 represents a $(C_1-C_6)$alkyl group or a —$(CHR9)_m$ $(CH_2)_n$NR7R8 group, R7 and R8 independently represent a $(C_1-C_4)$alkyl group or form together with the nitrogen atom to which they are attached a saturated or insaturated 5- or 6-membered ring optionally containing a further heteroatom chosen among nitrogen and oxygen, said ring being optionally substituted by a methyl group, and said ring being chosen among a imidazolyl, a morpholinyl, a piperidinyl, a pyrrolidinyl or 4-methylpiperazinyl group, R9 represents a $(C_1-C_2)$alkyl group, m is 0 or 1, n is 1, 2 or 3, provided that one of R1 and R2 is a hydrogen atom and the other is different from a hydrogen atom, or anyone of its pharmaceutically acceptable salt, for use in a method for preventing, inhibiting or treating a disease in a patient suffering thereof, said disease involving a deregulated p53.

According to another particular embodiment, an additional subject-matter of the present invention is a compound of formula (Ie)

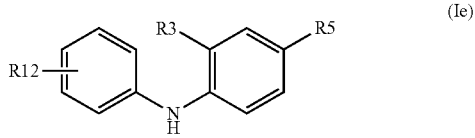

(Ie)

wherein:
R3 is a hydrogen atom or a $(C_1-C_4)$alkyl group,
R5 is as defined above in anyone of the embodiments of formula (I), and
R12 is a hydrogen atom, a $(C_1-C_4)$alkoxy group or a trifluoro$(C_1-C_4)$alkoxy group,
or one of its pharmaceutically acceptable salt,
for use in a method for preventing, inhibiting or treating a disease in a patient suffering thereof, said disease involving a deregulated p53.

According to a more particular aspect of said embodiment, an additional subject-matter of the present invention is a compound of formula (Ie)
wherein:
R3 is a hydrogen atom or a methyl group,
R5 represents
a —CONHR6 group, or
a triazolyl or imidazolyl group, said groups being optionally substituted by a chlorine atom, a —$(CH_2)_n$NR7R8 group or a hydroxy$(C_1-C_4)$alkyl group,
R6 represents a $(C_1-C_6)$alkyl group or a —$(CH_2)_n$NR7R8 group,
R7 and R8 independently represent a $(C_1-C_4)$alkyl group or form together with the nitrogen atom to which they are attached a saturated or insaturated 5- or 6-membered ring optionally containing a further heteroatom chosen among nitrogen and oxygen, said ring being optionally substituted by a methyl group, and said ring being chosen among a imidazolyl, a morpholinyl, a piperidinyl, a pyrrolidinyl or 4-methylpiperazinyl group,
n is 1, 2 or 3,
R12 is a hydrogen atom, a methoxy group, a trifluoromethoxy group or a benzyloxy group,
or one of its pharmaceutically acceptable salt,
for use in a method for preventing, inhibiting or treating a disease in a patient suffering thereof, said disease involving a deregulated p53.

According to another particular embodiment, an additional subject-matter of the present invention is a compound of formula (If)

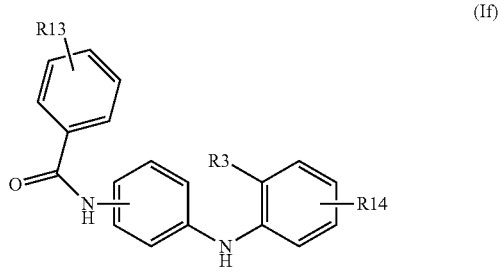

(If)

wherein:
R3 is a hydrogen atom or a $(C_1-C_4)$alkyl group,
R13 is a hydrogen atom, a $(C_1-C_4)$alkoxy group or a trifluoro$(C_1-C_4)$alkoxy group and can be in ortho, meta or para position, R14, which can be in meta or para position, represents
a —CONHR6 group,
a heteroaryl group optionally substituted by a —$(CH_2)_n$NR7R8 group or a hydroxy$(C_1-C_4)$alkyl group,
R6 represents a $(C_1-C_6)$alkyl group optionally substituted by a hydroxyl group, or a —$(CH_2)_n$NR7R8 group,
R7 and R8 independently represent a $(C_1-C_4)$alkyl group or form together with the nitrogen atom to which they are attached a saturated or insaturated 5- or 6-membered ring optionally containing a further heteroatom chosen among nitrogen and oxygen and optionally substituted by a $(C_1-C_4)$alkyl group, and said ring being chosen among a imidazolyl, a morpholinyl, a piperidinyl, a pyrrolidinyl or 4-methylpiperazinyl group,
or one of its pharmaceutically acceptable salt,
for use in a method for preventing, inhibiting or treating a disease in a patient suffering thereof, said disease involving a deregulated p53.

According to a more particular aspect of said embodiment, an additional subject-matter of the present invention is a compound of formula (If)
wherein:
R3 is a hydrogen atom or a methyl group,
R13 is a methoxy group and can be in meta or para position,
R14, which can be in meta or para position, represents
a —CONHR6 group,
a triazolyl or imidazolyl group, said groups being optionally substituted by a chlorine atom, a —$(CH_2)_n$NR7R8 group or a hydroxy$(C_1-C_4)$alkyl group,
R6 represents a $(C_1-C_6)$alkyl group optionally substituted by a hydroxyl group, or a —$(CH_2)_n$NR7R8 group,
R7 and R8 independently represent a $(C_1-C_4)$alkyl group or form together with the nitrogen atom to which they are attached a saturated or insaturated 5- or 6-membered ring optionally containing a further heteroatom chosen among nitrogen and oxygen and optionally substituted by a methyl group, and said ring being chosen among a imidazolyl, a morpholinyl, a piperidinyl, a pyrrolidinyl or 4-methylpiperazinyl group,
or one of its pharmaceutically acceptable salt,
for use in a method for preventing, inhibiting or treating a disease in a patient suffering thereof, said disease involving a deregulated p53.

According to a preferred embodiment of the present invention, the compound for use in a method for preventing, inhibiting or treating diseases involved with p53 expression, is chosen from one of the compounds as listed in table I below.

The chemical structures and spectroscopic data of some compounds of formula (I) of the invention are illustrated respectively in the following Table I and Table II.

TABLE I
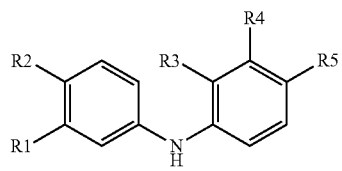
| Compound numbers | Formulae |
|---|---|
| | (Ia) |
| 1 | |
| 2 | |
| 3 | |
| 4 | |
| 5 | |
| 6 | |

TABLE I-continued
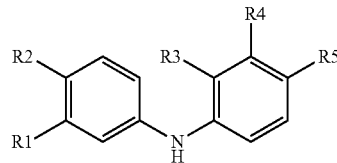
| Compound numbers | Formulae |
|---|---|
| 7 | |
| 8 | |
| 9 | |
| 10 | |
| 11 | |
| 12 | |

TABLE I-continued
| Compound numbers | Formulae |
|---|---|
| 13 | 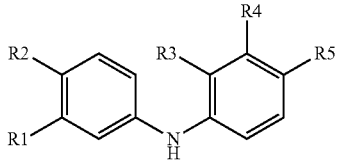 |
| 14 | 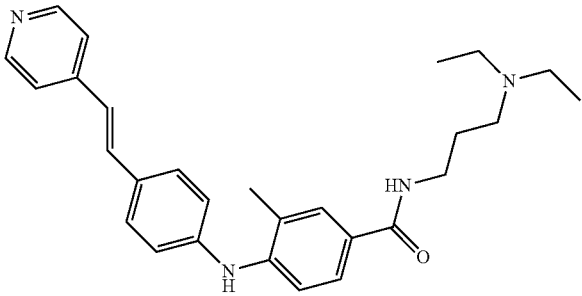 [SMILES: CCN(CC)CCCNC(=O)c1ccc(Nc2ccc(/C=C/c3ccncc3)cc2)c(C)c1] |
| 15 | 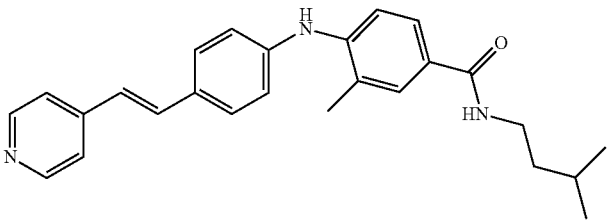 [SMILES: Cc1cc(C(=O)NCCC(C)C)ccc1Nc1ccc(/C=C/c2ccncc2)cc1] |
| 16 | 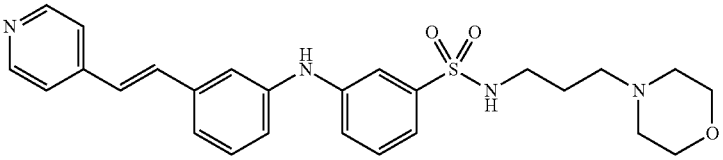 [SMILES: O=S(=O)(NCCCN1CCOCC1)c1cccc(Nc2cccc(/C=C/c3ccncc3)c2)c1] |
| 17 | 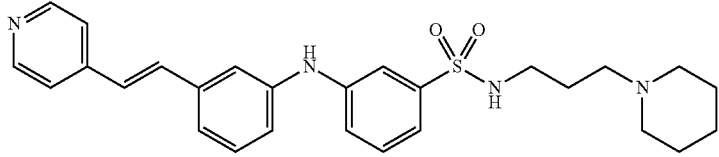 [SMILES: O=S(=O)(NCCCN1CCCCC1)c1cccc(Nc2cccc(/C=C/c3ccncc3)c2)c1] |
| 18 | 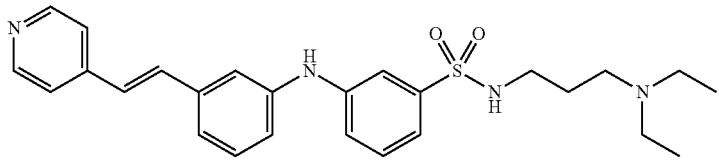 [SMILES: CCN(CC)CCCNS(=O)(=O)c1cccc(Nc2cccc(/C=C/c3ccncc3)c2)c1] |

TABLE I-continued

Structure (I): diarylamine with substituents R1, R2 on one ring and R3, R4, R5 on the other ring.

| Compound numbers | Formulae |
|---|---|
| 19 | (E)-N-(3-(3-(2-(pyridin-4-yl)vinyl)phenylamino)benzoyl)-3-(piperidin-1-yl)propan-1-amine |
| 20 | (E)-N-(3-(3-(2-(pyridin-4-yl)vinyl)phenylamino)benzoyl)-3-(morpholin-4-yl)propan-1-amine |
| 21 | (E)-N-(3-(3-(2-(pyridin-4-yl)vinyl)phenylamino)benzoyl)-3-(4-methylpiperazin-1-yl)propan-1-amine |
| 22 | (E)-N-(3-(3-(2-(pyridin-4-yl)vinyl)phenylamino)benzoyl)-3-(pyrrolidin-1-yl)propan-1-amine |
| 23 | (E)-(4-methylpiperazin-1-yl)(3-(3-(2-(pyridin-4-yl)vinyl)phenylamino)phenyl)methanone |
| 24 | (E)-3-(3-(2-(pyridin-4-yl)vinyl)phenylamino)-N-(2-(piperidin-1-yl)ethyl)benzenesulfonamide |
| 25 | (E)-3-(3-(2-(pyridin-4-yl)vinyl)phenylamino)-N-(2-(pyrrolidin-1-yl)ethyl)benzenesulfonamide |
| 127 | (E)-3-(3-(2-(pyridin-4-yl)vinyl)phenylamino)benzenesulfonamide |

TABLE I-continued
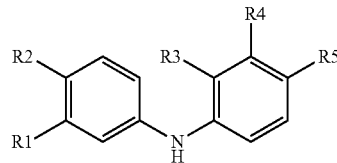
(I)
| Compound numbers | Formulae |
|---|---|
| 128 | 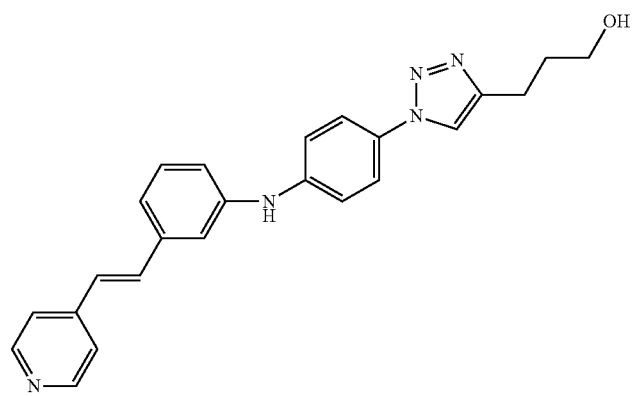 |
| 129 | 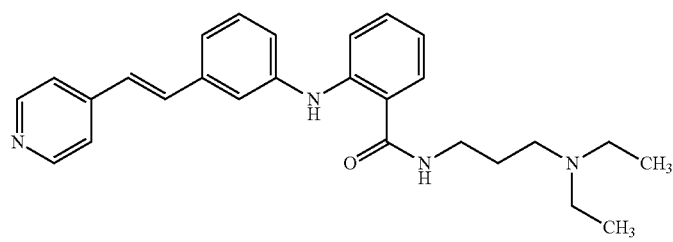 |
(Ib)
| 26 | 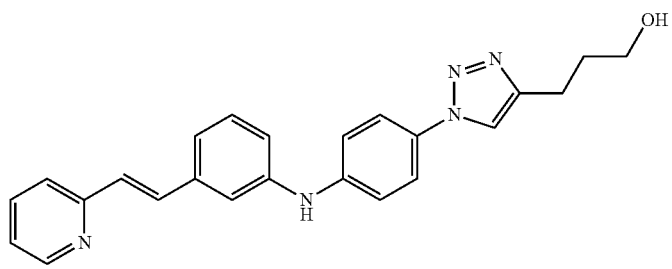 |
|---|---|
| 27 | 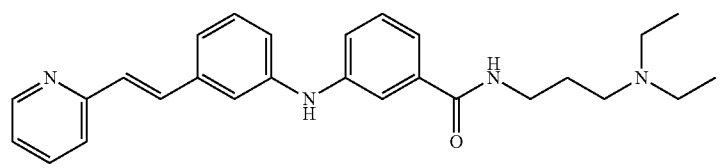 |
| 28 | 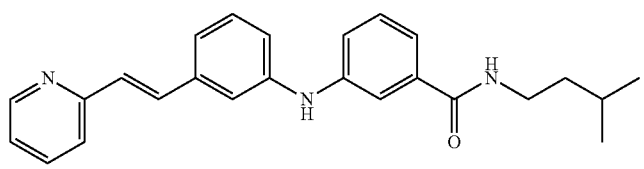 |

TABLE I-continued (I)

| Compound numbers | Formulae |
|---|---|
| 29 | |
| 30 | |
| 31 | |
| 32 | |
| 33 | |

TABLE I-continued
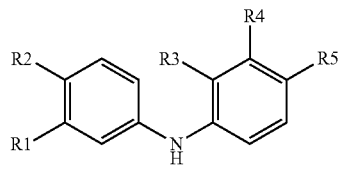
(I)
| Compound numbers | Formulae |
| --- | --- |
| 34 | |
| 35 | |
| 36 | |
| 130 | |
| 131 | |
| 132 | |
| 133 | |

TABLE I-continued
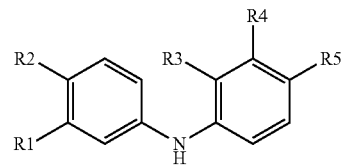
| Compound numbers | Formulae |
|---|---|
| 134 | |
| 135 | |
| 37 | |
| 38 | |
| 39 | |
| 40 | |
| 41 | |

TABLE I-continued
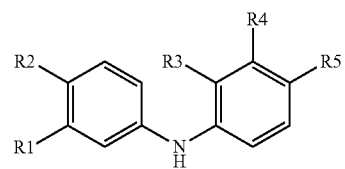
(I)
| Compound numbers | Formulae |
|---|---|
| 42 | 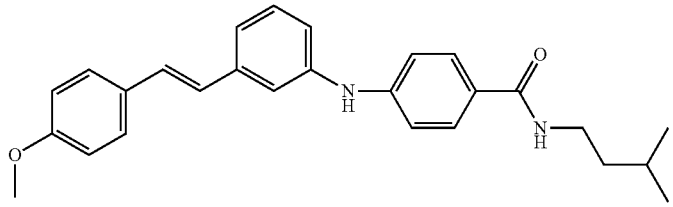 |
| 43 | 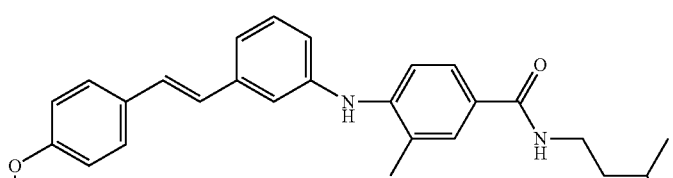 |
| 44 | 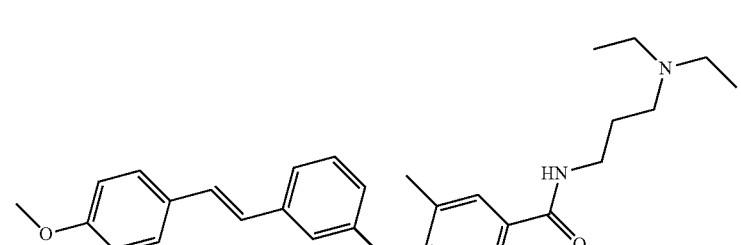 |
| 136 | 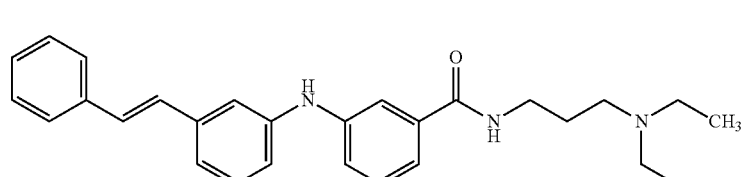 |
| | (Id) |
| 45 | 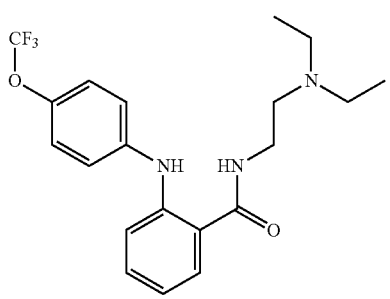 |

TABLE I-continued
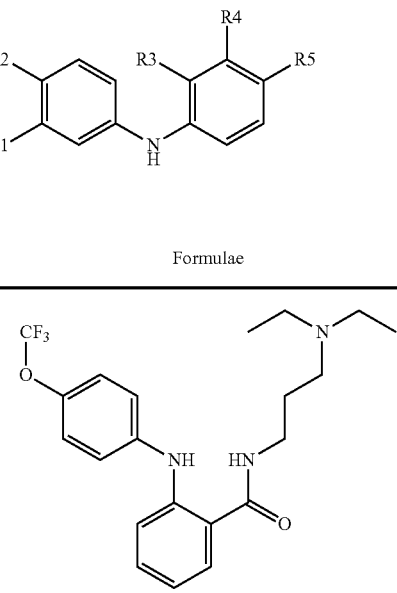
(I)
| Compound numbers | Formulae |
|---|---|
| 46 | 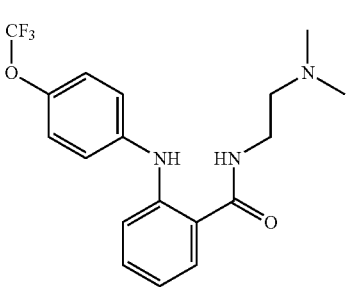 |
| 47 | |
| 48 | 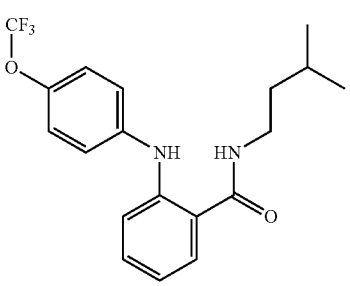 |
| 49 | 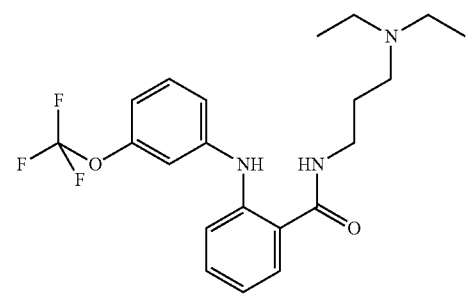 |

TABLE I-continued

Structure (I): R1, R2 on one phenyl ring; R3, R4, R5 on other phenyl ring connected via NH.

| Compound numbers | Formulae |
|---|---|
| 50 | 2-((4-(benzyloxy)phenyl)amino)-N-(3-(diethylamino)propyl)benzamide |
| 51 | N-(3-(diethylamino)propyl)-2-(phenylamino)benzamide |
| 52 | N-(3-(diethylamino)propyl)-2-((4-hydroxyphenyl)amino)benzamide |
| 53 | N-(2-(dimethylamino)ethyl)-2-((4-methoxyphenyl)amino)benzamide |

TABLE I-continued
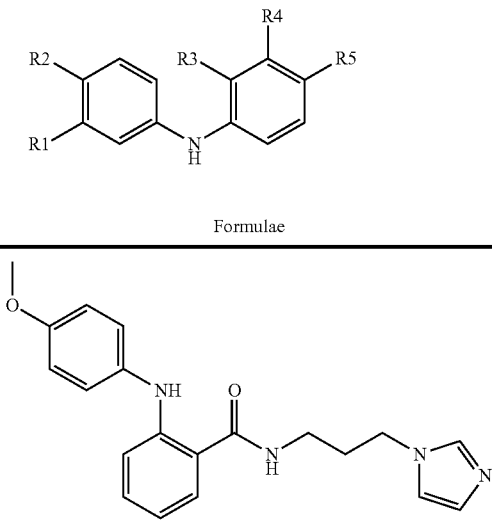
(I)
| Compound numbers | Formulae |
|---|---|
| 54 | 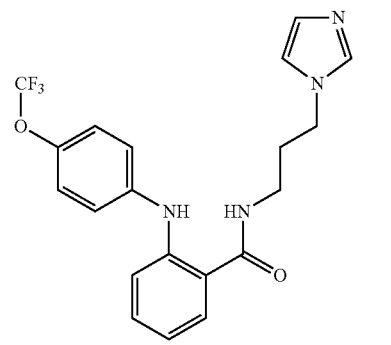 |
| 55 | 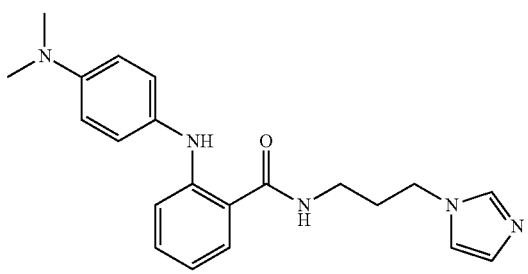 |
| 56 | 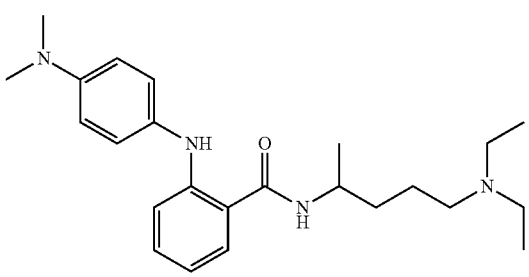 |
| 57 | 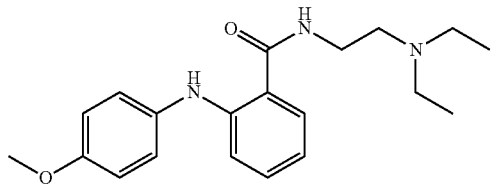 |
| 58 | |

TABLE I-continued

| Compound numbers | Formulae |
|---|---|
| 59 | 2-((4-methoxyphenyl)amino)-N-(3-(diethylamino)propyl)benzamide |
| 60 | 2-((3-methoxyphenyl)amino)-N-(3-(1H-imidazol-1-yl)propyl)benzamide |
| 61 | 4-((4-(trifluoromethoxy)phenyl)amino)-N-(3-(1H-imidazol-1-yl)propyl)benzamide (Ie) |
| 62 | 4-((3-methoxyphenyl)amino)-N-(2-(dimethylamino)ethyl)benzamide |
| 63 | 4-((4-(trifluoromethoxy)phenyl)amino)-N-(2-(dimethylamino)ethyl)benzamide |
| 64 | 4-((4-methoxyphenyl)amino)-N-(2-(dimethylamino)ethyl)-3-methylbenzamide |

TABLE I-continued
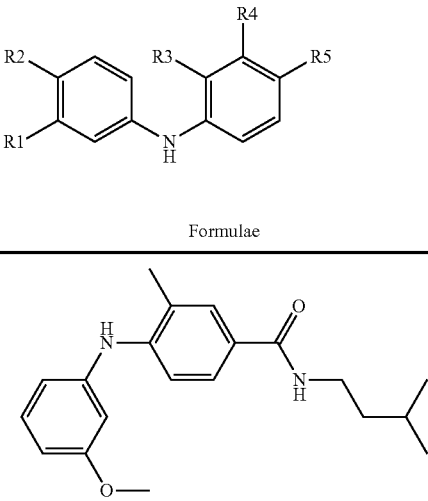
| Compound numbers | Formulae |
|---|---|
| 65 | 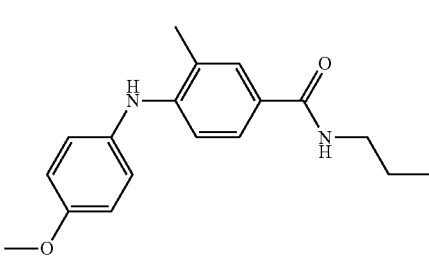 |
| 66 | 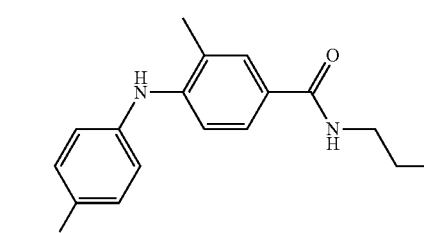 |
| 67 | 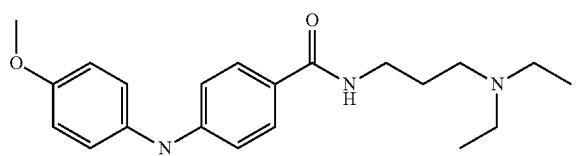 |
| 68 | 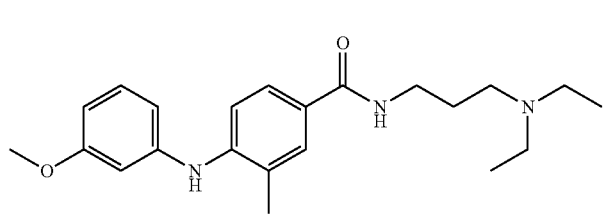 |
| 69 | 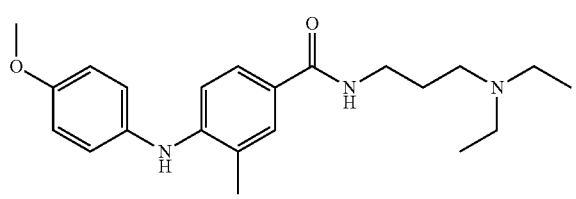 |
| 70 | |

TABLE I-continued

Structure (I): Two phenyl rings connected by NH; left ring has R1, R2; right ring has R3, R4, R5.

| Compound numbers | Formulae |
| --- | --- |
| 71 | 4-(trifluoromethoxy)phenyl-NH-(3-methyl-4-aminophenyl)-C(=O)-NH-CH₂CH₂CH₂-N(Et)₂ |
| 72 | 4-(trifluoromethoxy)phenyl-NH-(3-methyl-4-aminophenyl)-C(=O)-NH-CH₂CH₂-N(Me)₂ |
| 73 | 3-methoxyphenyl-NH-phenyl-(1,2,3-triazol-1-yl)-4-(CH₂CH₂CH₂OH) |
| 74 | 4-(hydroxymethyl)phenyl-NH-phenyl-(1,2,3-triazol-1-yl)-4-(CH₂CH₂CH₂OH) |
| 75 | 4-ethylphenyl-NH-phenyl-C(=O)-NH-CH₂CH₂CH₂-N(Me)₂ |
| 76 | 4-methoxyphenyl-NH-(3-methylphenyl)-(5-chloro-1H-imidazol-2-yl) |
| 77 | 4-methoxyphenyl-NH-phenyl-C(=O)-NH-CH₂CH₂-N(Et)₂ |

TABLE I-continued

![Structure (I): Diphenylamine core with substituents R1, R2 on one ring and R3, R4, R5 on the other ring, connected via NH]

| Compound numbers | Formulae |
|---|---|
| 78 | 3-methoxyphenyl-NH-phenyl-(1,2,3-triazol-1-yl)-CH2-N(Et)2 |
| 79 | 4-methoxyphenyl-NH-phenyl-(1,2,3-triazol-1-yl)-CH2-N(Et)2 |
| 80 | 4-(trifluoromethoxy)phenyl-NH-phenyl-(1,2,3-triazol-1-yl)-CH2-N(Et)2 |
| 81 | 3-methoxyphenyl-NH-phenyl-C(O)NH-CH2CH2CH(CH3)2 |
| 82 | 4-methoxyphenyl-NH-phenyl-C(O)NH-CH2CH2CH(CH3)2 |
| 83 | 2-(trifluoromethoxy)phenyl-NH-phenyl-C(O)NH-CH2CH2CH(CH3)2 |

TABLE I-continued
(I)
| Compound numbers | Formulae |
|---|---|
| 84 | 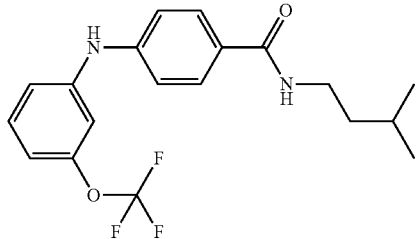 |
| 85 | 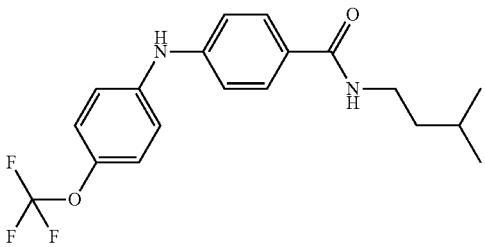 |
| 86 | 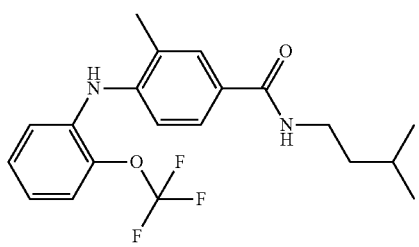 |
| 87 | 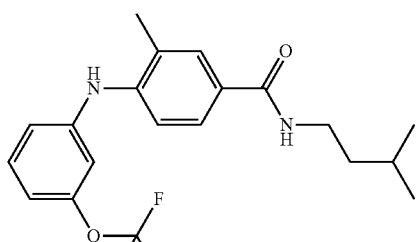 |
| 88 | 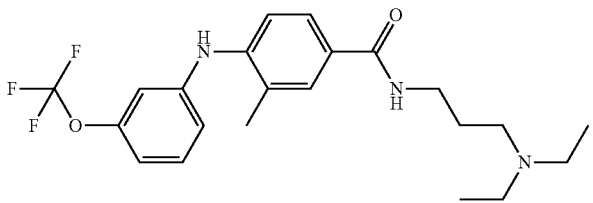 |

TABLE I-continued (I)

| Compound numbers | Formulae |
|---|---|
| 89 | (structure: 4-(phenylamino)-3-methyl-N-(3-(diethylamino)propyl)benzamide) |
| 90 | (structure: 4-((3-methoxyphenyl)amino)-N-(3-(1H-imidazol-1-yl)propyl)benzamide) |
| 91 | (structure: 4-((3-methoxyphenyl)amino)-3-methyl-N-(3-(1H-imidazol-1-yl)propyl)benzamide) |
| 92 | (structure: 4-((3-methoxyphenyl)amino)-3-methyl-N-(2-(dimethylamino)ethyl)benzamide) |

(If)

| 93 | (structure: 3-methoxy-N-(3-((3-((3-(diethylamino)propyl)carbamoyl)phenyl)amino)phenyl)benzamide) |
| 94 | (structure: 3-methoxy-N-(3-((4-((3-(diethylamino)propyl)carbamoyl)-2-methylphenyl)amino)phenyl)benzamide) |

TABLE I-continued
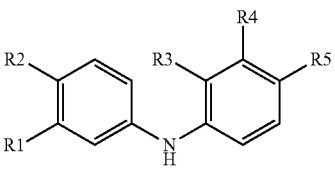
(I)
| Compound numbers | Formulae |
|---|---|
| 95 | 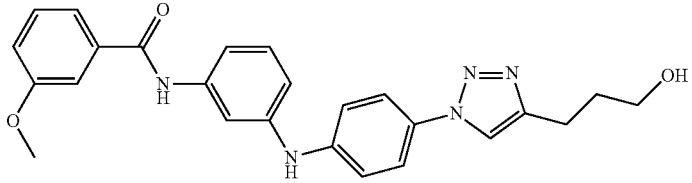 |
| 96 | 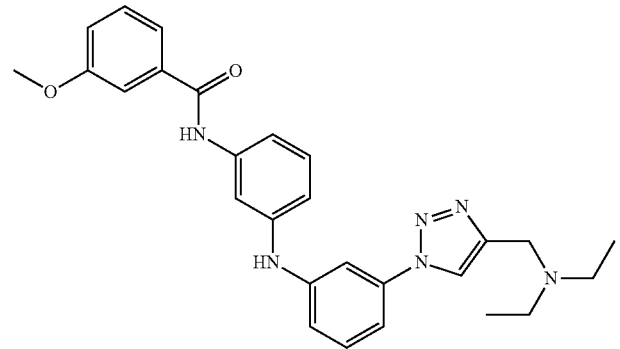 |
| 97 | 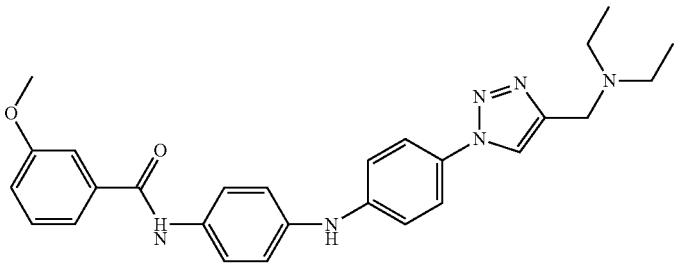 |
| 98 | 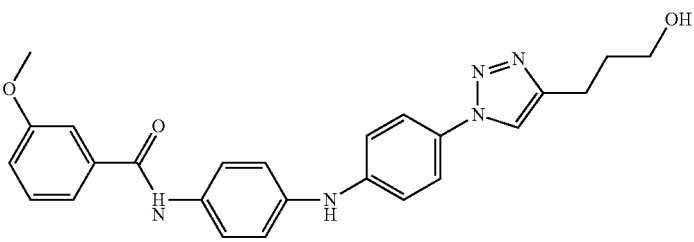 |

TABLE I-continued
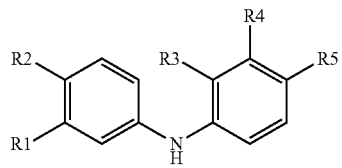
| Compound numbers | Formulae |
|---|---|
| 99 | |
| 100 | |
| 101 | |
| 102 | |
| 103 | |
| 104 | |

TABLE I-continued
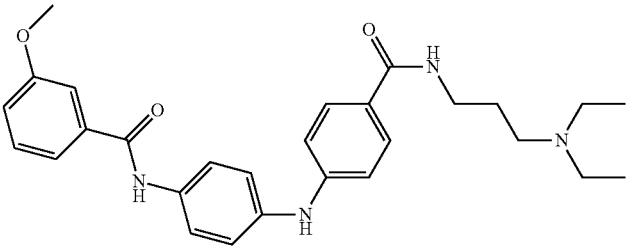
| Compound numbers | Formulae |
| --- | --- |
| 105 | 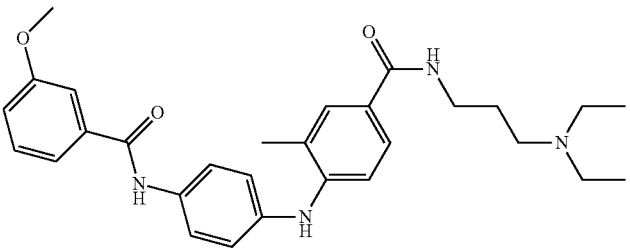 |
| 106 | 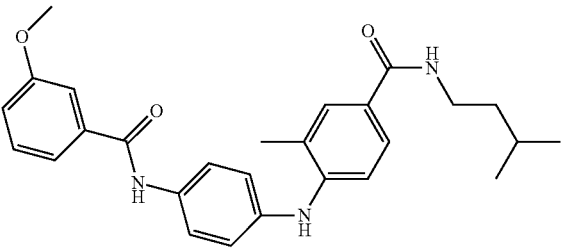 |
| 107 | 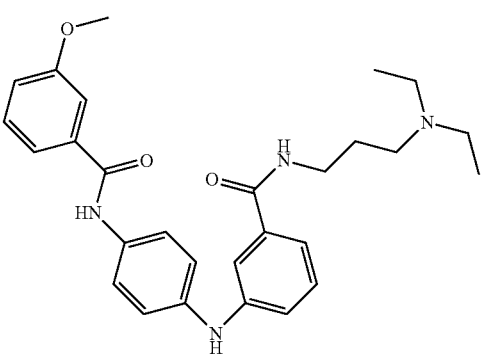 |
| 108 | |

TABLE I-continued
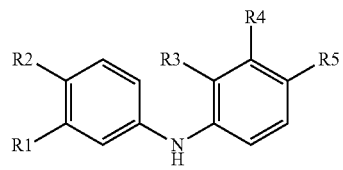
| Compound numbers | Formulae |
| --- | --- |
| 109 | |
| 110 | |
| 111 | |
| 112 | |

TABLE I-continued
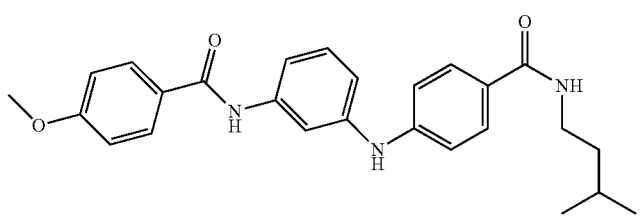
| Compound numbers | Formulae |
|---|---|
| 113 | 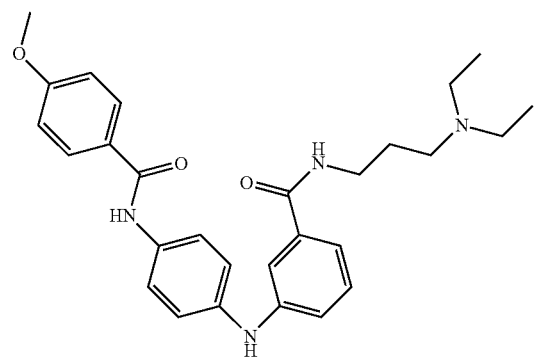 |
| 114 | 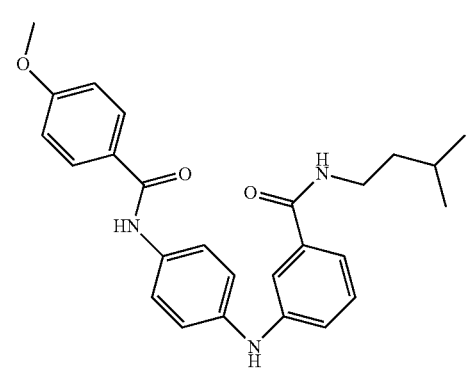 |
| 115 | 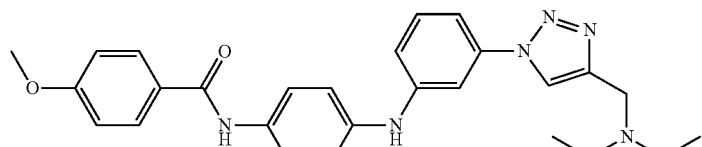 |
| 116 | |

TABLE I-continued

Structure (I):
Diphenylamine core with substituents R1, R2 on one ring and R3, R4, R5 on the other ring, connected via NH.

| Compound numbers | Formulae |
|---|---|
| 117 | 4-methoxy-N-[4-({3-[4-(3-hydroxypropyl)-1H-1,2,3-triazol-1-yl]phenyl}amino)phenyl]benzamide |
| 118 | 4-methoxy-N-{4-[(4-{[3-(diethylamino)propyl]carbamoyl}-2-methylphenyl)amino]phenyl}benzamide |
| 119 | 4-methoxy-N-{4-[(4-{[(3-methylbutyl)amino]carbonyl}phenyl)amino]phenyl}benzamide |
| 120 | 3-methoxy-N-{3-[(4-{[(5-hydroxypentyl)amino]carbonyl}-2-methylphenyl)amino]phenyl}benzamide |
| 121 | 3-methoxy-N-(3-{[4-(5-chloro-1H-imidazol-2-yl)-2-methylphenyl]amino}phenyl)benzamide |

TABLE I-continued (I)

[Structure of Formula (I): 3-R1, 4-R2 substituted phenyl-NH-phenyl (2-R3, 3-R4, 4-R5)]

| Compound numbers | Formulae |
|---|---|
| 122 | 3-methoxybenzamide-N-(4-aminophenyl) linked to 3-methyl-4-amino-N-hexylbenzamide |
| 123 | 4-(trifluoromethoxy)benzamide-N-(4-aminophenyl) linked to 3-[4-((diethylamino)methyl)-1H-1,2,3-triazol-1-yl]aniline |
| 124 | 2-methoxybenzamide-N-(4-aminophenyl) linked to 3-[4-((diethylamino)methyl)-1H-1,2,3-triazol-1-yl]aniline |
| 125 | benzamide-N-(4-aminophenyl) linked to 3-[4-((diethylamino)methyl)-1H-1,2,3-triazol-1-yl]aniline |

TABLE I-continued
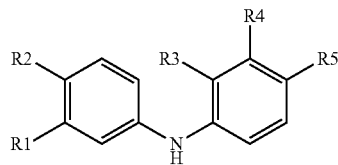
| Compound numbers | Formulae |
|---|---|
| 126 | 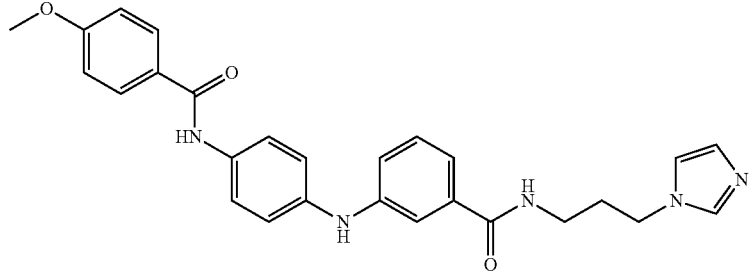 |
| 137 | 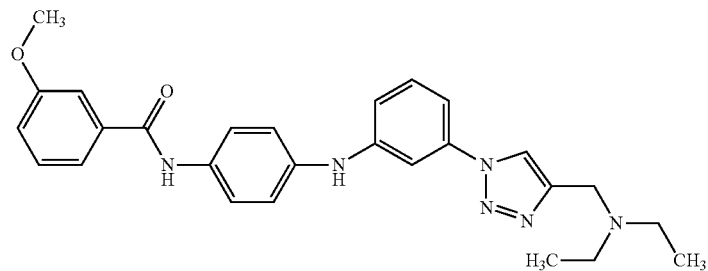 |
| 138 | 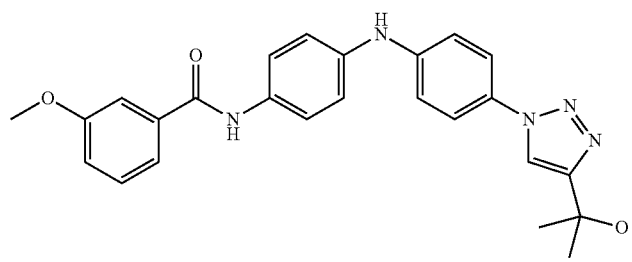 |
| 139 | 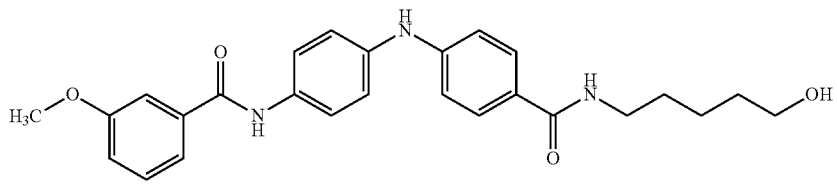 |
| 140 | 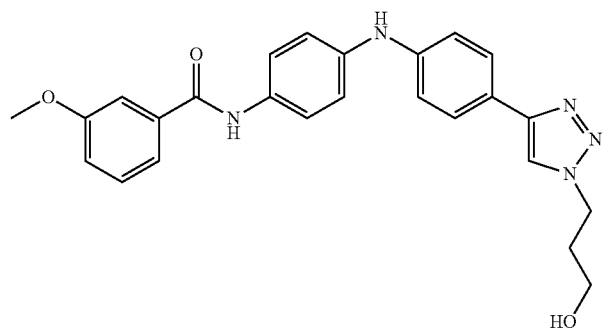 |

TABLE II

| Ex | Characterizations |
|---|---|
| 1 | ¹H NMR (300 MHz, DMSO-d6) δ 8.52 (d, J = 5.7 Hz, 2H), 8.39 (s, 1H), 8.35-8.30 (m, 1H), 7.55 (d, J = 6.0 Hz, 2H), 7.50 (d, J = 16.7 Hz, 1H), 7.32-7.27 (m, 5H), 7.20 (d, J = 7.6 Hz, 2H), 7.15 (d, J = 11.4 Hz, 1H), 7.05 (d, J = 8.2 Hz, 1H), 3.22 (q, J = 6.9 Hz, 2H), 1.58 (heptuplet, J = 6.6 Hz, 1H), 1.37 (q, J = 6.9 Hz, 2H), 0.87 (d, J = 6.6 Hz, 6H).<br>¹³C NMR (75 MHz, DMSO-d6) δ 166.3, 150.0, 143.6, 143.4, 137.2, 136.1, 133.3, 129.7, 129.1, 125.8, 120.9, 119.0, 118.8, 118.2, 117.5, 115.8, 115.6, 38.1, 37.4, 25.3, 22.5.<br>[M + H]⁺ = 386.2 |
| 2 | ¹H NMR (300 MHz, CDCl₃) δ 8.70 (s, 1H), 8.51 (d, J = 4.9 Hz, 2H), 7.61 (s, 1H), 7.30-7.14 (m, 8H), 7.08-7.00 (m, 2H), 6.89 (d, J = 16.4 Hz, 1H), 6.58 (s, 1H), 3.52-3.48 (m, 2H), 2.59-2.40 (m, 6H), 1.69-1.65 (m, 2H), 0.95 (t, J = 7.1 Hz, 6H).<br>¹³C NMR (75 MHz, CDCl₃) δ 167.1, 150.3, 144.7, 143.6, 143.5, 137.6, 136.5, 133.3, 130.0, 129.4, 126.3, 121.1, 120.3, 120.2, 119.1, 118.8, 117.1, 116.9, 53.4, 46.9, 41.4, 25.0, 11.6.<br>[M + H]⁺ = 429.2 |
| 3 | ¹H NMR (300 MHz, CDCl₃) δ 8.55 (bs, 2H), 7.96 (s, 1H), 7.55 (s, 1H), 7.42-7.03 (m, 10H), 6.96 (d, J = 16.2 Hz, 1H), 6.53 (s, 1H), 3.87 (s, 2H), 2.62 (q, J = 7.0 Hz, 4H), 1.10 (t, J = 7.1 Hz, 6H).<br>[M + H]⁺ = 425.2 |
| 4 | ¹H NMR (300 MHz, CDCl₃) δ 8.52 (bs, 2H), 7.73 (s, 1H), 7.50 (s, 1H), 7.38-7.05 (m, 9H), 6.95 (d, J = 16.2 Hz, 1H), 6.55 (s, 1H), 2.89 (t, J = 7.4 Hz, 2H), 2.52 (s, 1H), 1.98 (t, J = 6.9 Hz, 2H), 1.23 (t, J = 7.0 Hz, 2H).<br>[M + H]⁺ = 398 |
| 5 | [M + H]⁺ = 386 |
| 6 | [M + H]⁺ = 443 |
| 7 | ¹H NMR (300 MHz, CDCl₃) δ 8.47 (d, J = 4.9 Hz, 2H), 7.58 (s, 1H), 7.46 (dd, J = 8.4, 2.0 Hz, 1H), 7.36-7.31 (m, 1H), 7.27 (d, J = 5.2 Hz, 2H), 7.25-7.03 (m, 5H), 7.00-6.78 (m, 1H), 6.11 (s, 1H), 5.71 (s, 1H), 3.38 (q, J = 6.5 Hz, 2H), 2.22 (s, 3H), 1.62 (heptuplet, J = 6.7 Hz, 1H), 1.43 (q, J = 6.1 Hz, 2H), 0.83 (d, J = 6.6 Hz, 6H).<br>[M + H]⁺ = 400 |
| 8 | ¹H NMR (300 MHz, DMSO) δ 8.60 (s, 1H), 8.50-8.45 (m, 2H), 8.15 (t, J = 6.0 Hz, 1H), 7.75 (d, J = 8.7 Hz, 2H), 7.56 (d, J = 4.3 Hz, 2H), 7.50-7.14 (m, 6H), 7.08 (d, J = 8.5 Hz, 2H), 3.26 (q, J = 6.4 Hz, 2H), 1.60 (heptuplet, J = 6.6 Hz, 1H), 1.40 (q, J = 7.0 Hz, 2H), 0.90 (d, J = 6.6 Hz, 6H). |
| 9 | ¹H NMR (300 MHz, C₅D₅N) δ 8.43 (s, 1H), 8.23 (d, J = 5.8, 2H), 7.89 (s, 1H), 7.48 (d, J = 7.3, 1H), 7.10-6.75 (m, 11H), 6.68 (d, J = 16.4, 1H).<br>¹³C NMR (75 MHz, C₅D₅N) δ 170.4, 151.2, 145.4, 145.3, 138.6, 137.6, 134.3, 130.8, 130.3, 127.0, 121.8, 121.0, 120.4, 120.2, 119.0, 117.9, 117.4.<br>[M + H]⁺ = 316 |
| 10 | [M + H]⁺ = 398 |
| 11 | [M + H]⁺ = 425 |
| 12 | [M + H]⁺ = 398 |
| 13 | ¹H NMR (300 MHz, CDCl₃) δ 8.71 (s, 1H), 8.50 (s, 2H), 7.39 (d, J = 7.7 Hz, 2H), 7.35-7.13 (m, 7H), 7.06 (d, J = 8.1 Hz, 2H), 6.81 (d, J = 16.6 Hz, 1H), 6.68 (s, 1H), 3.52 (s, 2H), 2.54 (m, 6H), 1.71 (s, 2H), 0.97 (t, J = 6.8 Hz, 6H).<br>[M + H]⁺ = 429.2 |
| 14 | ¹H NMR (300 MHz, CDCl₃) δ 8.47 (d, J = 5.0 Hz, 2H), 7.67-7.45 (m, 4H), 7.42-7.06 (m, 4H), 7.06-6.94 (m, 3H), 6.88 (d, J = 17.4 Hz, 1H), 5.72 (s, 1H), 3.55-3.45 (m, 2H), 2.36-2.26 (m, 2H), 2.22 (s, 3H), 1.69 (m, 6H), 1.20 (t, 6H).<br>[M + H]⁺ = 443 |
| 15 | ¹H NMR (300 MHz, CDCl₃) δ 8.48 (d, J = 5.8 Hz, 2H), 7.66-7.31 (m, 6H), 7.30-7.15 (m, 3H), 7.06-6.79 (m, 2H), 5.98 (s, 1H), 5.70 (s, 1H), 3.40 (q, J = 6.6 Hz, 2H), 2.23 (s, 3H), 1.62 (quint, J = 6.5 Hz, 2H), 1.44 (q, J = 7.1 Hz, 2H), 0.89 (d, J = 6.5 Hz, 6H).<br>[M + H]⁺ = 400 |
| 16 | ¹H NMR (300 MHz, CDCl₃) δ 8.50 (s, 2H), 7.52 (s, 1H), 7.38-7.18 (m, 7H), 7.18-7.00 (m, 3H), 6.93 (d, J = 16.2 Hz, 1H), 6.66 (s, 1H), 3.76-3.40 (m, 4H), 3.15-2.91 (m, 2H), 2.46-2.12 (m, 2H + 4H), 1.69-1.45 (m, 2H).<br>[M + H]⁺ = 479.2 |
| 17 | ¹H NMR (300 MHz, CDCl₃) δ 8.59 (s, 2H), 7.57 (s, 1H), 7.38 (s, 4H), 7.30 (d, J = 5.5 Hz, 4H), 7.15 (dd, J = 27.1, 6.6 Hz, 2H), 7.01 (d, J = 16.9 Hz, 1H), 6.29 (s, 1H), 3.17-3.00 (m, 2H), 2.59-2.20 (m, 6H), 1.74-1.52 (m, 6H), 1.52-1.35 (m, 2H).<br>[M + H]⁺ = 477.2 |
| 18 | ¹H NMR (300 MHz, CDCl₃) δ 8.55 (d, J = 5.8 Hz, 2H), 7.58 (s, 1H), 7.39-7.32 (m, 4H), 7.31-7.24 (m, 3H), 7.21 (s, 1H), 7.15 (d, J = 7.7 Hz, 1H), 7.10 (d, J = 7.9 Hz, 1H), 6.98 (d, J = 16.3 Hz, 1H), 6.64 (d, J = 8.4 Hz, 1H), 3.15-3.00 (m, 2H), 2.52-2.35 (m, 2H + 4H), 1.68-1.53 (m, 2H), 0.96 (t, J = 7.1 Hz, 6H).<br>[M + H]⁺ = 465.2 |
| 19 | ¹H NMR (300 MHz, CDCl₃) δ 8.54 (d, J = 4.4 Hz, 2H), 7.61 (s, 1H), 7.38-7.16 (m, 7H), 7.10 (d, J = 7.8 Hz, 2H), 7.05 (d, J = 7.8 Hz, 2H), 6.93 (d, J = 16.3 Hz, 1H), 6.30 (s, 1H), 3.53 (q, J = 5.0 Hz, 2H), 2.55-2.50-2.46 (m, 2H), 2.45-2.40 (m, 4H), 1.78-1.72 (s, 2H), 1.55-1.50 (s, 4H), 1.48-1.35 (m, 2H).<br>¹³C NMR (75 MHz, CDCl₃) δ 167.45, 150.34, 144.72, 143.56, 137.58, 136.62, 133.29, 130.03, 129.37, 126.34, 121.07, 120.26, 119.38, 118.61, 117.36, 116.65, 59.28, 54.91, 41.23, 26.04, 24.45, 24.26.<br>[M + H]⁺ = 441.1 |

TABLE II-continued

| Ex | Characterizations |
|---|---|
| 20 | $^1$H NMR (300 MHz, CDCl$_3$) δ 8.50 (d, J = 4.2 Hz, 2H), 8.01 (s, 1H), 7.58 (s, 1H), 7.32-7.13 (m, 8H), 7.07 (d, J = 7.9 Hz, 1H), 7.03 (d, J = 7.9 Hz, 1H), 6.90 (d, J = 16.3 Hz, 1H), 6.54 (s, 1H), 3.70-3.55 (m, 4H), 3.51 (q, J = 4.8 Hz, 2H), 2.50-2.40 (m, 6H), 1.84-1.54 (m, 2H).<br>$^{13}$C NMR (75 MHz, CDCl$_3$) δ 167.56, 150.30, 144.69, 143.82, 143.29, 137.59, 136.47, 133.23, 130.04, 129.54, 126.38, 121.07, 120.37, 120.13, 118.82, 116.90, 66.97, 58.68, 53.93, 40.63, 24.36.<br>[M + H]$^+$ = 443.2 |
| 21 | $^1$H NMR (300 MHz, CDCl$_3$) δ 8.49 (d, J = 3.6 Hz, 2H), 8.23 (s, 1H), 7.56 (s, 1H), 7.39-7.11 (m, 7H), 7.14-6.98 (m, 3H), 6.90 (d, J = 15.8 Hz, 1H), 6.53 (s, 1H), 3.49 (s, 2H), 3.23 (s, 2H), 2.2.5-2.30 (m, 8H), 2.20 (s, 3H), 1.75-1.70 (m, 2H).<br>$^{13}$C NMR (75 MHz, CDCl$_3$) δ 167.47, 150.25, 144.65, 143.65, 143.38, 137.49, 136.43, 133.24, 129.95, 129.35, 126.26, 121.02, 120.13, 119.99, 119.17, 118.56, 117.07, 116.68, 58.36, 55.12, 53.37, 46.13, 40.93, 24.40.<br>[M + H]$^+$ = 456.2 |
| 22 | $^1$H NMR (300 MHz, CDCl$_3$) δ 8.69 (s, 1H), 8.52 (bs, 2H), 7.59 (s, 1H), 7.39-7.15 (m, 8H), 7.09 (d, J = 8.2 Hz, 1H), 7.06 (d, J = 8.2 Hz, 1H), 6.93 (d, J = 15.5 Hz, 1H), 6.38 (s, 1H), 3.54 (s, 2H), 2.70-2.60 (m, 2H), 2.55-2.50 (m, 4H), 1.80-1.70 (m, 6H).<br>[M + H]$^+$ = 427.2 |
| 23 | $^1$H NMR (300 MHz, CDCl$_3$) δ 8.54 (s, 2H), 7.36-7.30 (d, J = 4.0 Hz, 2H), 7.29-7.16 (m, 4H), 7.11 (d, J = 8.8 Hz, 3H), 7.03 (d, J = 7.5 Hz, 2H), 6.98-6.86 (m, 2H), 6.59 (s, 1H), 3.90-3.70 (m, 2H), 3.58-3.31 (m, 2H), 2.50-2.21 (m, 4H + 3H).<br>[M + H]$^+$ = 399.2 |
| 24 | $^1$H NMR (300 MHz, CDCl$_3$) δ 8.55 (s, 2H), 7.58 (s, 1H), 7.43-7.23 (m, 7H), 7.23-7.04 (m, 3H), 6.97 (d, J = 16.3 Hz, 1H), 6.67 (s, 1H), 4.51 (br s, 1H), 3.07-2.91 (m, 2H), 2.43-2.28 (m, 2H), 2.26-2.03 (m, 4H), 1.53-1.40 (m, 4H), 1.40-1.31 (m, 2H).<br>[M + H]$^+$ = 463.2 |
| 25 | $^1$H NMR (300 MHz, CDCl$_3$) δ 8.57 (s, 2H), 7.58 (s, 1H), 7.43-7.23 (m, 7H), 7.23-7.05 (m, 3H), 6.98 (d, J = 15.6 Hz, 1H), 6.55 (s, 1H), 4.67 (br s, 1H), 3.13-2.93 (m, 2H), 2.61-2.44 (m, 2H), 2.43-2.17 (m, 4H), 1.78-1.51 (m, 4H).<br>[M + H]$^+$ = 449.2 |
| 127 | $^1$H NMR (300 MHz, MeOD) δ 8.43 (s, 2H), 7.67 (s, 1H), 7.53 (d, J = 5.2 Hz, 2H), 7.42 (d, J = 16.5 Hz, 1H), 7.38-7.13 (m, 8H), 7.13-7.07 (m, 1H), 7.09 (d, J = 16.5 Hz, 1H).<br>[M + H]$^+$ = 352.1 |
| 128 | $^1$H NMR (300 MHz, MeOD) δ 8.47 (dd, J = 4.8, 1.5 Hz, 2H), 8.18 (s, 1H), 7.66 (dd, J = 6.7, 2.1 Hz, 2H), 7.58 (dd, J = 4.8, 1.5 Hz, 2H), 7.47 (d, J = 16.4 Hz, 1H), 7.40 (t, J = 1.6 Hz, 1H), 7.32 (t, J = 7.8 Hz, 1H), 7.24 (dd, J = 6.7, 2.1 Hz, 2H), 7.18-7.11 (m, 2H), 7.15 (d, J = 16.4 Hz, 1H), 3.65 (q, J = 7.1 Hz, 2H), 2.86 (t, J = 7.4 Hz, 2H), 1.95 (q, J = 7.4 Hz, 2H). |
| 129 | $^1$H NMR (300 MHz, DMSO) δ 9.72 (s, 1H), 8.65 (t, J = 5.3 Hz, 1H), 8.54 (br s, 1H), 7.63 (d, J = 7.7 Hz, 1H), 7.59-7.52 (m, 2H), 7.52 (d, J = 16.4 Hz, 1H), 7.41 (s, 1H), 7.37-7.30 (m, 3H), 7.29-7.20 (m, 1H), 7.24 (d, J = 16.4 Hz, 1H), 7.12 (d, J = 8.1 Hz, 1H), 6.91-6.83 (m, 1H), 3.31-3.21 (m, 2H), 2.61-2.39 (m, 6H), 1.74-1.59 (m, 2H), 0.95 (t, J = 6.7 Hz, 6H).<br>[M + H]$^+$ = 429.3 |
| 26 | $^1$H NMR (300 MHz, CDCl$_3$) δ 8.51 (d, J = 4.5, 1H), 7.61 (s, 1H), 7.56 (d, J = 7.6, 1H), 7.48 (d, J = 16.1, 1H), 7.41 (d, J = 8.7, 2H), 7.30 (d, J = 7.8, 1H), 7.21 (s, 1H), 7.17 (d, J = 7.7, 1H), 7.12-7.01 (m, 5H), 6.97 (d, J = 7.8, 1H), 6.87 (s, 1H), 4.19 (s, 1H), 3.70 (t, J = 6.2, 2H), 2.84 (t, J = 7.4, 2H), 2.00 (quint, J = 6.7, 2H).<br>$^{13}$C NMR (75 MHz, CDCl$_3$) δ 155.6, 149.8, 148.2, 144.0, 142.7, 138.1, 136.9, 132.7, 130.3, 130.0, 128.4, 122.4, 122.1, 121.0, 119.5, 118.9, 117.7, 117.3, 61.9, 32.2, 22.3.<br>[M + H]$^+$ = 398 |
| 27 | $^1$H NMR (300 MHz, MeOD) δ 8.49 (s, 1H), 7.81 (m, 1H), 7.65-7.45 (m, 4H), 7.35-7.05 (m, 9H), 3.45 (m, 2H), 3.31 (m, 4H), 2.06 (m, 2H), 1.28 (m, 6H), 0.89 (m, 2H).<br>[M + H]$^+$ = 429 |
| 28 | $^1$H NMR (300 MHz, CDCl$_3$) δ 8.59 (d, J = 3.9 Hz, 1H), 7.64 (m, 1H), 7.55 (d, J = 16.1 Hz, 1H), 7.48 (s, 1H), 7.44-7.32 (m, 2H), 7.31-6.94 (m, 8H), 6.24 (s, 1H), 6.12 (s, 1H), 3.44 (q, J = 6.1 Hz, 2H), 1.66 (heptuplet, J = 6.6 Hz, 1H), 1.48 (q, J = 7.0 Hz, 2H), 0.93 (d, J = 6.6 Hz, 6H).<br>[M + H]$^+$ = 386 |
| 29 | [M + H]$^+$ = 398 |
| 30 | [M + H]$^+$ = 429 |
| 31 | $^1$H NMR (300 MHz, CDCl$_3$) δ 8.58 (d, J = 3.0 Hz, 1H), 7.85-6.73 (m, 12H), 6.25 (t, J = 5.3 Hz, 1H), 5.75 (s, 1H), 3.46 (q, J = 6.7 Hz, 2H), 2.27 (s, 3H), 1.68 (heptuplet, J = 6.7 Hz, 1H), 1.50 (q, J = 7.1 Hz, 2H), 0.94 (q, J = 6.6 Hz, 6H).<br>[M + H]$^+$ = 400 |
| 32 | $^1$H NMR (300 MHz, CDCl$_3$) δ 8.59 (d, J = 5.5 Hz, 1H), 7.81-7.48 (m, 6H), 7.47-7.32 (m, 3H), 7.19 (d, J = 8.8 Hz, 2H), 7.16-7.02 (m, 2H), 6.98 (s, 1H), 6.09 (s, 1H), 3.77 (t, J = 6.1 Hz, 2H), 2.92 (t, J = 7.3 Hz, 2H), 2.04-1.98 (m, 2H).<br>[M + H]$^+$ = 398 |
| 33 | [M + H]$^+$ = 429 |
| 34 | $^1$H NMR (300 MHz, CDCl$_3$) δ 8.59 (d, J = 4.2 Hz, 1H), 7.70-7.46 (m, 5H), 7.45-7.19 (m, 5H), 7.16-6.99 (m, 3H), 6.01 (s, 1H), 5.93 (s, 1H), 3.47 (q, J = 5.9 Hz, 2H), 1.68 (heptuplet, J = 6.6 Hz, 1H), 1.51 (q, J = 7.6 Hz, 2H), 0.96 (d, J = 6.6 Hz, 6H).<br>[M + H]$^+$ = 386 |
| 35 | [M + H]$^+$ = 429 |
| 36 | [M − H]$^−$ = 386 |
| 130 | $^1$H NMR (300 MHz, MeOD) δ 8.52-8.46 (m, 1H), 7.81 (td, J = 7.7, 1.7 Hz, 1H), 7.64 (d, J = 7.9 Hz, 1H), 7.58-7.50 (m, 2H), 7.36-7.23 (m, 6H), 7.22-7.15 (m, 2H), 7.19 (d, J = 16.3 Hz, 1H), 7.19 (s, 1H), 7.13-7.07 (m, 1H), 3.42 (t, J = 6.7 Hz, 2H), 2.91-2.41 (m, 10H), 2.38 (s, 3H), 1.89-1.77 (m, 2H). |

TABLE II-continued

| Ex | Characterizations |
|---|---|
| 131 | ¹H NMR (300 MHz, MeOD) δ 8.51-8.46 (m, 1H), 7.80 (td, J = 7.8, 1.8 Hz, 1H), 7.66-7.58 (m, 2H), 7.53 (d, J = 16.4 Hz, 1H), 7.36-7.24 (m, 6H), 7.18 (d, J = 16.4 Hz, 1H), 7.18 (s, 1H), 7.13-7.07 (m, 1H), 3.47 (t, J = 6.6 Hz, 2H), 3.15-3.06 (m, 4H), 3.05-2.97 (m, 2H), 2.04-1.92 (m, 6H). |
| 132 | ¹H NMR (300 MHz, MeOD) δ 8.50-8.45 (m, 1H), 7.77 (td, J = 7.7, 1.8 Hz, 1H), 7.63-7.57 (m, 2H), 7.51 (d, J = 16.3 Hz, 1H), 7.35-7.21 (m, 6H), 7.16 (d, J = 16.3 Hz, 1H), 7.16 (s, 1H), 7.12-7.06 (m, 1H), 3.40 (t, J = 6.7 Hz, 2H), 2.72-2.55 (m, 6H), 1.95-1.83 (m, 2H), 1.72-1.59 (m, 4H), 1.54-1.41 (m, 2H). |
| 133 | ¹H NMR (300 MHz, MeOD) δ 8.51-8.47 (m, 1H), 7.65-7.59 (m, 1H), 7.59-7.57 (m, 1H), 7.54 (d, J = 16.4 Hz, 1H), 7.43-7.24 (m, 6H), 7.23-7.18 (m, 1H), 7.19 (d, J = 16.3 Hz, 1H), 7.14-7.08 (m, 1H), 2.95 (t, J = 6.5 Hz, 2H), 2.75-2.61 (m, 6H), 1.77-1.62 (m, 2H), 1.07 (t, J = 7.2 Hz, 6H). |
| 134 | ¹H NMR (300 MHz, MeOD) δ 8.50-8.44 (m, 1H), 7.76 (td, J = 7.7, 1.7 Hz, 1H), 7.63-7.55 (m, 2H), 7.51 (d, J = 16.3 Hz, 1H), 7.36-7.20 (m, 6H), 7.16 (d, J = 16.3 Hz, 1H), 7.16 (s, 1H), 7.12-7.06 (m, 1H), 3.65 (t, J = 4.5 Hz, 4H), 3.40 (t, J = 6.8 Hz, 2H), 2.55-2.41 (m, 6H), 1.81 (dt, J = 14.0, 6.9 Hz, 2H). |
| 135 | ¹H NMR (300 MHz, MeOD) δ 8.51-8.46 (m, 1H), 7.78 (td, J = 7.7, 1.8 Hz, 1H), 7.63-7.56 (m, 2H), 7.52 (d, J = 16.3 Hz, 1H), 7.42-7.22 (m, 6H), 7.18 (d, J = 16.3 Hz, 1H), 7.18 (s, 1H), 7.11 (dd, J = 7.9, 1.1 Hz, 1H), 2.93 (t, J = 6.6 Hz, 2H), 2.61-2.45 (m, 6H), 1.79-1.67 (m, 2H), 1.66-1.55 (m, 4H), 1.51-1.38 (m, 2H). |
| 37 | ¹H NMR (300 MHz, CDCl₃) δ 8.62 (s, 1H), 7.59 (s, 1H), 7.49 (d, J = 7.3 Hz, 2H), 7.24 (m, Hz, 6H), 7.06 (m, 5H), 6.10 (s, 1H), 3.55 (q, 2H), 2.74-2.40 (m, 6H), 1.75 (m, 2H), 1.01 (t, 6H).<br>[M + H]⁺ = 512 |
| 38 | [M + H]⁺ = 539 |
| 39 | ¹H NMR (300 MHz, CDCl₃) δ 8.22 (s, 1H), 7.58 (s, 1H), 7.44-7.17 (m, 9H), 7.11 (d, J = 7.3 Hz, 2H), 7.03 (d, J = 2.6 Hz, 2H), 6.16 (s, 1H), 3.55 (q, J = 5.0 Hz, 3H), 2.60-2.40 (m, 10H), 2.25 (s, 3H), 1.88-1.55 (m, 2H).<br>[M + H]⁺ = 539 |
| 40 | ¹H NMR (300 MHz, CDCl₃) δ 8.59 (s, 1H), 7.52 (s, 1H), 7.43 (d, J = 8.7 Hz, 2H), 7.27 (d, J = 7.0 Hz, 2H), 7.23 (d, J = 7.3 Hz, 2H), 7.18 (s, 1H), 7.13-6.92 (m, 4H), 6.89 (d, J = 8.7 Hz, 2H), 3.82 (s, 3H), 3.59-3.47 (m, 2H), 2.62-2.46 (m, 6H), 1.72 (quint, J = 5.7 Hz, 2H), 0.99 (t, J = 7.2 Hz, 6H).<br>¹³C NMR (75 MHz, CDCl₃) δ 167.2, 159.5, 144.0, 143.2, 139.1, 136.4, 130.2, 129.8, 129.4, 128.6, 127.9, 119.8, 118.9, 117.6, 116.6, 114.3, 55.5, 53.3, 46.9, 41.3, 25.1, 11.6.<br>[M + H]⁺ = 458.3 |
| 41 | ¹H NMR (300 MHz, CDCl₃) δ 7.45-7.31 (m, 4H), 7.25-7.20 (m, 1H), 7.19 (s, 1H), 7.17-7.10 (m, 3H), 7.09-6.98 (m, 1H), 6.96-6.75 (m, 4H), 3.75 (s, 3H), 1.59 (heptuplet, J = 13.3, 6.6 Hz, 1H), 1.42 (q, J = 8.7, 7.1 Hz, 2H), 0.87 (d, J = 6.6 Hz, 6H)<br>¹³C NMR (75 MHz, CDCl₃) δ 167.6, 159.5, 144.0, 142.8, 139.2, 136.4, 130.1, 129.8, 129.6, 129.1, 128.7, 128.5, 127.9, 126.5, 120.0, 119.8, 118.6, 117.7, 116.5, 116.3, 114.3, 55.4, 38.6, 38.5, 26.1, 22.6<br>[M + H]⁺ = 415 |
| 42 | [M + H]⁺ = 415 |
| 43 | [M + H]⁺ = 429 |
| 44 | ¹H NMR (300 MHz, CDCl₃) δ 10.77 (s, 1H), 8.15 (s, 1H), 7.75 (s, 1H), 7.66 (d, J = 9.0 Hz, 1H), 7.39 (d, J = 8.3 Hz, 2H), 7.30-7.05 (m, 3H), 7.0-6.90 (m, 3H), 6.86 (s, 1H), 6.84 (d, J = 8.5 Hz, 2H), 3.77 (s, 3H), 3.55-3.49 (m, 2H), 2.95-2.80 (m, 6H), 2.26 (s, 3H), 2.15-2.05 (m, 2H), 1.30 (t, J = 7.2 Hz, 6H).<br>[M + H]⁺ = 472 |
| 136 | ¹H NMR (300 MHz, MeOD) δ 7.57-7.53 (m, 2H), 7.52 (s, 1H), 7.36-7.21 (m, 8H), 7.15-7.10 (m, 3H), 7.04 (ddd, J = 7.9, 2.2, 1.0 Hz, 1H), 3.39 (t, J = 6.7 Hz, 2H), 2.68-2.58 (m, 6H), 1.87-1.74 (m, 2H), 1.05 (t, J = 7.2 Hz, 6H). |
| 45 | ¹H NMR (300 MHz, CDCl₃) δ 9.55 (s, 1H), 7.48 (d, J = 7.7 Hz, 1H), 7.30-7.21 (m, 3H), 7.15 (d, J = 9.1 Hz, 2H), 7.10 (d, J = 9.1 Hz, 2H), 6.78 (t, J = 7.3 Hz, 1H), 3.44 (t, J = 5.9 Hz, 2H), 2.62 (t, J = 5.9 Hz, 2H), 2.54 (q, J = 7.1 Hz, 4H), 1.02 (t, J = 7.1 Hz, 6H).<br>¹³C NMR (75 MHz, CDCl₃) δ 169.5, 145.2, 143.9, 140.8, 132.2, 127.8, 122.3, 121.4, 119.1, 118.7, 115.6, 51.3, 46.9, 37.2, 12.1.<br>[M + H]⁺ = 396 |
| 46 | ¹H NMR (300 MHz, CDCl₃) δ 9.83 (s, 1H), 8.84 (s, 1H), 7.42 (d, J = 7.3 Hz, 1H), 7.28 (t, J = 7.1 Hz, 2H), 7.20-7.07 (m, 5H), 6.75 (t, J = 6.7 Hz, 1H), 3.52 (q, J = 5.2 Hz, 2H), 2.82-2.40 (m, 6H), 1.80-1.70 (m, 2H), 1.03 (t, J = 7.1 Hz, 6H)<br>¹³C NMR (75 MHz, CDCl₃) δ 169.4, 145.3, 143.7, 140.9, 132.0, 127.9, 122.2, 121.3, 119.0, 118.7, 118.2, 115.4, 53.6, 46.9, 41.2, 24.8, 11.5<br>[M + H]⁺ = 410 |
| 47 | ¹H NMR (300 MHz, CDCl₃) δ 9.50 (s, 1H), 7.47 (d, J = 7.4 Hz, 1H), 7.35-7.23 (m, 2H), 7.18 (d, J = 9.0 Hz, 2H), 7.14 (d, J = 9.0 Hz, 2H), 6.94 (bs, 1H), 6.80 (t, J = 6.3 Hz, 1H), 3.48 (bs, 2H), 2.54 (bs, 2H), 2.28 (s, 6H).<br>[M + H]⁺ = 368 |
| 48 | ¹H NMR (300 MHz, CDCl₃) δ 8.31 (d, J = 8.9 Hz, 1H), 7.95 (d, J = 2.8 Hz, 1H), 7.61 (t, J = 9.1 Hz, 2H), 6.97 (d, J = 8.9 Hz, 1H), 6.84 (d, J = 8.8 Hz, 1H), 6.59 (d, J = 8.5 Hz, 1H), 4.25 (t, J = 5.4 Hz, 2H), 3.92 (s, 3H), 3.79-3.72 (m, 1H), 2.92 (t, J = 5.5 Hz, 2H), 2.68-2.60 (m, 5H)<br>[M + H]⁺ = 367.2 |
| 49 | ¹H NMR (300 MHz, CDCl₃) δ 9.90 (s, 1H), 8.74 (s, 1H), 7.58 (d, J = 6.4 Hz, 1H), 7.45-7.21 (m, 3H), 7.09 (d, J = 11.1 Hz, 2H), 6.83 (dd, J = 16.4, 7.7 Hz, 2H), 3.76-3.40 (m, 2H), 3.13-2.41 (m, 2H + 4H), 2.10-1.69 (m, 2H), 1.15 (t, J = 7.2 Hz, 6H).<br>[M + H]⁺ = 410.2 |
| 50 | ¹H NMR (300 MHz, CDCl₃) δ 9.64 (s, 1H), 8.74 (s, 1H), 7.49-7.30 (m, 6H), 7.23-7.08 (m, 4H), 6.95 (d, J = 8.9 Hz, 2H), 6.66 (t, J = 7.4 Hz, 1H), 5.06 (s, 2H), 3.61-3.45 (m, 2H), 2.73-2.47 (m, |

TABLE II-continued

| Ex | Characterizations |
|---|---|
| | 2H + 4H), 1.84-1.71 (m, 2H), 1.07 (t, J = 7.1 Hz, 6H).<br>$^{13}$C NMR (75 MHz, CDCl$_3$) δ 169.7, 155.1, 147.6, 137.3, 135.0, 132.0, 128.7, 128.1, 127.8, 127.7, 124.4, 116.7, 116.5, 115.7, 114.3, 70.5, 53.5, 46.8, 41.0, 24.8, 11.5.<br>[M + H]$^+$ = 432.2 |
| 51 | $^1$H NMR (300 MHz, CDCl$_3$) δ 9.77 (s, 1H), 8.77 (s, 1H), 7.43 (d, J = 7.8 Hz, 1H), 7.35 (t, J = 8.7 Hz, 1H), 7.30-7.14 (m, 5H), 6.99 (t, J = 7.1 Hz, 1H), 6.73 (t, J = 7.4 Hz, 1H), 3.60-3.46 (m, 2H), 2.68-2.50 (m, 2H + 4H), 1.84-1.69 (m, 2H), 1.05 (t, J = 7.1 Hz, 6H).<br>$^{13}$C NMR (75 MHz, CDCl$_3$) δ 169.5, 145.7, 141.9, 131.9, 129.3, 127.8, 122.2, 120.8, 118.3, 117.6, 115.3, 53.5, 46.8, 41.0, 24.8, 11.4.<br>[M + H]$^+$ = 326.3 |
| 52 | $^1$H NMR (300 MHz, CDCl$_3$) δ 9.50 (s, 1H), 8.75 (s, 1H), 7.41 (d, J = 7.8 Hz, 1H), 7.25-7.14 (m, 1H), 7.06 (d, J = 8.3 Hz, 2H), 7.00-6.89 (m, 1H), 6.80 (d, J = 8.2 Hz, 2H), 6.66 (t, J = 7.4 Hz, 1H), 3.69-3.42 (m, 2H), 2.71-2.52 (m, 2H + 4H), 1.89-1.72 (m, 2H), 1.07 (t, J = 7.1 Hz, 6H).<br>[M + H]$^+$ = 342.3 |
| 53 | [M + H]$^+$ = 414 |
| 54 | [M + H]$^+$ = 351 |
| 55 | [M + H]$^+$ = 405 |
| 56 | [M + H]$^+$ = 364 |
| 57 | [M + H]$^+$ = 397 |
| 58 | [M + H]$^+$ = 342 |
| 59 | [M + H]$^+$ = 356 |
| 60 | $^1$H NMR (300 MHz, CDCl$_3$) δ 9.23 (s, 1H), 7.40 (s, 1H), 7.31 (d, J = 8.3 Hz, 1H), 7.20-7.00 (m, 3H), 6.97 (t, J = 8.1 Hz, 1H), 6.76-6.61 (m, 3H), 6.47 (d, J = 7.5 Hz, 1H), 6.22 (t, J = 8.7 Hz, 1H), 6.16 (s, 1H), 4.01 (m, 2H), 3.70 (s, 3H), 3.32 (m, 2H), 2.08 (m, 2H).<br>[M + H]$^+$ = 351 |
| 61 | [M + H]$^+$ = 405 |
| 62 | [M + H]$^+$ = 314 |
| 63 | [M + H]$^+$ = 368 |
| 64 | [M + H]$^+$ = 328 |
| 65 | $^1$H NMR (300 MHz, CDCl$_3$) δ 7.62 (s, 1H), 7.50 (dd, J = 1.9, 8.5 Hz, 1H), 7.23-7.14 (m, 2H), 6.69-6.59 (m, 2H), 6.54 (dd, J = 2.2, 8.1 Hz, 1H), 6.30 (d, J = 5.4 Hz, 1H), 5.73 (s, 1H), 3.75 (s, 3H), 3.40 (q, J = 7.0 Hz, 2H), 2.23 (s, 3H), 1.69 (heptuplet, J = 6.6 Hz, 1H), 1.50 (q, J = 7.0 Hz, 2H), 0.93 (d, J = 6.6 Hz, 6H).<br>$^{13}$C NMR (75 MHz, CDCl$_3$) 167.4, 160.9, 144.7, 143.6, 130.4, 130.1, 126.7, 125.8, 125.7, 115.5, 112.2, 107.7, 105.4, 55.4, 38.8, 38.5, 26.2, 22.7, 18.0.<br>[M + H]$^+$ = 327 |
| 66 | $^1$H NMR (300 MHz, CDCl$_3$) δ 7.57 (d, J = 1.5 Hz, 1H), 7.52-7.32 (m, 2H), 7.07 (d, J = 8.9 Hz, 2H), 6.87 (d, J = 8.9 Hz, 2H), 5.96 (s, 1H), 5.46 (s, 1H), 3.79 (s, 3H), 3.42 (q, J = 7.4 Hz, 2H), 2.25 (s, 3H), 1.65 (quint, J = 7.4 Hz, 1H), 1.46 (q, J = 7.4 Hz, 2H), 0.92 (d, J = 6.6 Hz, 6H).<br>[M + H]$^+$ = 327 |
| 67 | $^1$H NMR (300 MHz, CDCl$_3$) δ 7.65 (s, 1H), 7.51 (d, J = 8.4 Hz, 1H), 7.16 (d, J = 8.6 Hz, 3H), 7.07 (d, J = 8.9 Hz, 2H), 6.02 (s, 1H), 5.65 (s, 1H), 3.47 (q, J = 7.0 Hz, 2H), 2.29 (s, 3H), 1.75-1.64 (m, 1H), 1.51 (q, J = 7.0 Hz, 2H), 0.96 (d, J = 6.6 Hz, 6H).<br>[M + H]$^+$ = 381 |
| 68 | [M + H]$^+$ = 356 |
| 69 | $^1$H NMR (300 MHz, CDCl$_3$) δ 8.48 (s, 1H), 7.68 (s, 1H), 7.56 (d, J = 8.4 Hz, 1H), 7.26-7.17 (m, 2H), 6.74-6.60 (m, 2H), 6.57 (d, J = 8.4 Hz, 1H), 5.59 (s, 1H), 3.79 (s, 3H), 3.56 (q, J = 5.3 Hz, 2H), 2.71-2.51 (m, 2H + 4H), 2.29 (s, 3H), 1.78 (quint, J = 5.9 Hz, 2H), 1.07 (t, J = 7.1 Hz, 6H).<br>$^{13}$C NMR (75 MHz, CDCl$_3$) δ 167.0, 160.8, 144.4, 143.7, 130.3, 130.1, 126.8, 125.9, 125.6, 115.4, 112.1, 107.6, 105.3, 58.6, 55.4, 46.9, 27.0, 18.6, 18.0, 11.5.<br>[M + H]$^+$ = 370 |
| 70 | $^1$H NMR (300 MHz, CDCl$_3$) δ 8.34 (s, 1H), 7.62 (s, 1H), 7.47 (d, J = 8.8 Hz, 1H), 7.08 (d, J = 8.8 Hz, 2H), 6.88 (d, J = 8.7 Hz, 3H), 5.44 (s, 1H), 3.80 (s, 3H), 3.52 (q, J = 5.3 Hz, 2H), 2.61 (t, J = 5.1 Hz, 2H), 2.57 (q, J = 7.1 Hz, 4H), 2.26 (s, 3H), 1.73 (quint, J = 5.7 Hz, 2H), 1.04 (t, J = 7.1 Hz, 6H).<br>[M + H]$^+$ = 370 |
| 71 | $^1$H NMR (300 MHz, CDCl$_3$) δ 8.55 (s, 1H), 7.68 (s, 1H), 7.56 (d, J = 8.5 Hz, 1H), 7.18-7.12 (m, 3H), 7.06 (d, J = 9.0 Hz, 2H), 5.81 (s, 1H), 3.54 (qd, J = 5.5 Hz, 2H), 2.70-2.60 (m, 2H), 2.62 (q, J = 7.1 Hz, 4H), 2.27 (s, 3H), 1.77 (heptuplet, J = 5.6 Hz, 2H), 1.07 (t, J = 7.1 Hz, 6H).<br>[M + H]$^+$ = 424 |
| 72 | [M + H]$^+$ = 382 |
| 73 | [M + H]$^+$ = 325 |
| 74 | [M + H]$^+$ = 325 |
| 75 | $^1$H NMR (300 MHz, CDCl$_3$) δ 8.05 (s, 1H), 7.61 (d, J = 8.6 Hz, 2H), 7.10 (d, J = 8.8 Hz, 2H), 6.85 (dd, J = 12.4, 8.8 Hz, 4H), 6.08 (s, 1H), 3.79 (s, 3H), 3.49 (dd, J = 11.4, 5.7 Hz, 3H), 2.43 (t, J = 6.2 Hz, 3H), 2.24 (s, 6H), 1.73 (dd, J = 12.1, 6.0 Hz, 3H), 1.25 (s, 6H). |
| 76 | $^1$H NMR (300 MHz, CDCl$_3$) δ 10.20 (s, 1H), 9.91 (s, 1H), 7.60 (s, 1H), 7.40 (d, J = 8.4 Hz, 1H), 7.03 (d, J = 8.4 Hz, 2H), 6.95-6.80 (m, 3H), 5.34 (s, 1H), 3.80 (s, 3H), 2.17 (s, 3H) |
| 77 | $^1$H NMR (300 MHz, CDCl$_3$) δ 7.59 (d, J = 8.7 Hz, 2H), 7.06 (d, J = 8.9 Hz, 1H), 6.84 (d, J = 8.9 Hz, 2H), 6.79 (d, J = 8.7 Hz, 2H), 3.41 (q, J = 5.3 Hz, 2H), 2.58 (t, J = 7.1 Hz,, 2H), 2.51 (q, J = 7.1 Hz, 4H), 0.98 (t, J = 7.1 Hz, 6H).<br>[M + H]$^+$ = 342 |
| 78 | [M + H]$^+$ = 352 |
| 79 | [M + H]$^+$ = 352 |
| 80 | $^1$H NMR (300 MHz, CDCl$_3$) δ 7.84 (s, 1H), 7.53 (d, J = 8.7 Hz, 2H), 7.09 (d, J = 8.0 Hz, 2H), 7.06 (d, J = 8.0 Hz, 2H), 7.03 (d, J = 8.0 Hz, 2H), 5.96 (s, 1H), 3.82 (s, 2H), 2.57 (q, J = 7.1 Hz, 4H), 1.06 (t, J = 7.1 Hz, 6H).<br>[M + H]$^+$ = 406 |

TABLE II-continued

| Ex | Characterizations |
|---|---|
| 81 | M + H]+ = 313 |
| 82 | ¹H NMR (300 MHz, CDCl₃) δ 7.59 (d, J = 8.7 Hz, 2H), 7.09 (d, J = 8.9 Hz, 2H), 6.86 (d, J = 8.9 Hz, 2H), 6.81 (d, J = 8.7 Hz, 2H), 5.80 (s, 1H), 3.79 (s, 3H), 3.42 (q, J = 7.1 Hz, 2H), 1.65 (quint, J = 6.6 Hz, 1H), 1.47 (q, 7.1 Hz, 1H), 0.92 (d, J = 6.6 Hz, 6H).<br>M + H]+ = 313 |
| 83 | ¹H NMR (300 MHz, CDCl₃) δ 7.72 (d, J = 8.6 Hz, 2H), 7.40 (d, J = 7.8 Hz, 1H), 7.27 (d, J = 7.8 Hz, 1H), 7.20 (t, J = 7.8 Hz, 1H), 7.08 (d, J = 8.6 Hz, 2H), 6.96 (t, J = 7.8 Hz, 1H), 6.24 (s, 1H), 6.13 (s, 1H), 3.52-3.39 (q, J = 6.6 Hz, 2H), 1.67 (hept, J = 6.6 Hz, 1H), 1.50 (q, J = 6.6 Hz, 2H), 0.94 (d, J = 6.6 Hz, 6H).<br>[M + H]+ = 367.1 |
| 84 | ¹H NMR (300 MHz, CDCl₃) δ 7.69 (d, J = 8.7 Hz, 1H), 7.27 (d, J = 7.5 Hz, 1H), 7.06 (d, J = 8.7 Hz, 1H), 7.04-6.94 (m, 2H), 6.82 (d, J = 7.5 Hz, 1H), 6.27 (s, 1H), 6.07 (s, 1H), 3.46 (q, J = 6.6 Hz, 2H), 1.68 (hept, J = 6.6 Hz, 1H), 1.50 (q, J = 6.6 Hz, 2H), 0.95 (d, J = 6.6 Hz, 1H).<br>¹³C NMR (75 MHz, CDCl₃) δ 167.1, 150.3, 145.4, 143.5, 130.6, 128.7, 127.3, 116.8, 116.6, 114.0, 111.0, 38.7, 38.5, 26.1, 22.6.<br>[M + H]+ = 367.1 |
| 85 | ¹H NMR (300 MHz, CDCl₃) δ 7.69 (d, J = 8.6 Hz, 2H), 7.21-7.07 (m, 2H), 7.02 (d, J = 8.6 Hz, 2H), 6.08-5.90 (m, 2H), 3.48 (q, J = 6.6 Hz, 2H), 1.70 (hept, J = 6.6 Hz, 1H), 1.51 (q, J = 6.6 Hz, 2H), 0.96 (d, J = 6.6 Hz, 6H).<br>[M + H]+ = 367.1 |
| 86 | ¹H NMR (300 MHz, CDCl₃) δ 7.66 (s, 1H), 7.54 (d, J = 8.3 Hz, 1H), 7.45-7.37 (m, 1H), 7.31-7.16 (m, 4H), 6.97-6.89 (m, 1H), 6.08 (s, 1H), 3.47 (q, J = 6.6 Hz, 2H), 2.29 (s, 3H), 1.68 (hept, J = 6.6 Hz, 1H), 1.51 (q, J = 6.6 Hz, 2H), 0.96 (d, J = 6.6 Hz, 6H).<br>¹³C NMR (75 MHz, CDCl₃) δ 167.2, 143.5, 143.1, 135.8, 130.1, 129.1, 128.5, 128.4, 128.1, 127.6, 125.8, 122.1, 121.3, 118.4, 117.5, 38.8, 38.5, 26.1, 22.6, 17.8.<br>[M + H]+ = 381.1 |
| 87 | ¹H NMR (300 MHz, CDCl₃) δ 7.66 (s, 1H), 7.52 (d, J = 8.4 Hz, 1H), 7.47-7.38 (m, 1H), 7.30 (d, J = 8.4 Hz, 1H), 7.24 (d, J = 8.4 Hz, 1H), 6.95 (d, J = 8.0 Hz, 1H), 6.89 (s, 1H), 6.82 (d, J = 8.0 Hz, 1H), 6.07 (s, 1H), 5.75 (s, 1H), 3.47 (q, J = 6.6 Hz, 2H), 2.29 (s, 3H), 1.69 (hept, J = 6.6 Hz, 1H), 1.51 (q, J = 6.6 Hz, 2H), 0.96 (d, J = 6.6 Hz, 6H).<br>¹³C NMR (75 MHz, CDCl₃) δ 167.2, 150.3, 144.3, 143.6, 130.6, 130.3, 129.1, 128.5, 128.0, 127.1, 125.7, 116.7, 116.6, 113.6, 110.9, 38.8, 38.5, 26.1, 22.6, 18.0.<br>[M + H]+ = 381.1 |
| 88 | ¹H NMR (300 MHz, CDCl₃) δ 8.21 (s, 1H), 7.89 (s, 1H), 7.80 (d, J = 8.3 Hz, 1H), 7.37-7.20 (m, 2H), 6.98 (d, J = 8.1 Hz, 1H), 6.90 (s, 1H), 6.80 (d, J = 8.0 Hz, 1H), 5.90 (s, 1H), 3.70-3.52 (m, 2H), 3.34-3.00 (m, 2H + 4H), 2.29 (s, 3H), 2.25-2.08 (m, 2H), 1.36 (t, J = 7.2 Hz, 6H).<br>¹³C NMR (75 MHz, CDCl₃) δ 167.9, 150.3, 144.2, 143.9, 130.7, 130.5, 126.9, 126.5, 116.8, 116.4, 113.5, 111.0, 49.5, 46.2, 41.1, 36.6, 23.9, 18.0, 8.4.<br>[M + H]+ = 424.1 |
| 89 | ¹H NMR (300 MHz, CDCl₃) δ 8.50 (s, 1H), 7.68 (s, 1H), 7.54 (d, J = 8.4 Hz, 1H), 7.32 (t, J = 7.1 Hz, 2H), 7.20 (d, J = 8.5 Hz, 1H), 7.11 (d, J = 7.5 Hz, 2H), 7.02 (t, J = 7.1 Hz, 1H), 5.61 (s, 1H), 3.70-3.40 (m, 2H), 2.76-2.46 (m, 2H + 4H), 2.29 (s, 3H), 1.85-1.66 (m, 2H), 1.06 (t, J = 6.8 Hz, 6H).<br>¹³C NMR (75 MHz, CDCl₃) δ 167.0, 144.7, 142.2, 130.1, 129.6, 126.5, 125.9, 125.1, 122.3, 119.9, 114.5, 53.3 (CH2), 46.9 (CH2 Et), 25.1 (CH2), 18.0, 11.5.<br>[M + H]+ = 339.9 |
| 90 | ¹H NMR (300 MHz, CDCl₃) δ 7.65 (d, J = 8.4 Hz, 2H), 7.60 (d, J = 6.2 Hz, 1H), 7.22 (d, J = 8.1 Hz, 1H), 7.04 (d, J = 8.3 Hz, 2H), 6.82-6.67 (m, 2H), 6.60 (d, J = 8.1 Hz, 1H), 6.18 (s, 1H), 6.03 (s, 1H), 4.07 (t, J = 6.7 Hz, 2H), 3.80 (s, 3H), 3.53-3.43 (m, 2H), 2.29-2.03 (m, 2H).<br>[M + H]+ = 351.1 |
| 91 | ¹H NMR (300 MHz, CDCl₃) δ 7.63 (s, 1H), 7.49 (d, J = 8.5 Hz, 1H), 7.26 (d, J = 7.8 Hz, 1H), 7.21 (d, J = 7.8 Hz, 1H), 7.09 (s, 1H), 7.01 (s, 1H), 6.75-6.64 (m, 2H), 6.59 (d, J = 8.2 Hz, 1H), 6.39 (s, 1H), 5.66 (s, 1H), 4.06 (t, J = 6.8 Hz, 2H), 3.79 (s, 3H), 3.47 (q, J = 6.4 Hz, 2H), 2.29 (s, 3H), 2.18-2.05 (quint, J = 6.6 Hz, 2H).<br>¹³C NMR (75 MHz, CDCl₃) δ 160.8, 145.1, 143.2, 130.4, 130.1, 125.9, 125.4, 115.0, 112.4, 107.9, 105.8, 55.4, 45.0, 37.3, 31.5, 17.9.<br>[M + H]+ = 365.1 |
| 92 | ¹H NMR (300 MHz, CDCl₃) δ 7.69 (s, 1H), 7.56 (d, J = 8.4 Hz, 1H), 7.26 (d, J = 7.8 Hz, 1H), 7.21 (d, J = 7.8 Hz, 1H), 6.81 (br s, 1H), 6.73-6.63 (m, 2H), 6.58 (d, J = 8.2 Hz, 1H), 5.60 (s, 1H), 3.80 (s, 3H), 3.55 (q, J = 5.7 Hz, 2H), 2.58 (t, J = 5.7 Hz, 2H), 2.33 (s, 6H), 2.31 (s, 3H).<br>[M + H]+ = 328.3 |
| 93 | [M + H]+ = 475 |
| 94 | [M + H]+ = 489 |
| 95 | [M + H]+ = 444 |
| 96 | [M + H]+ = 471 |
| 97 | [M + H]+ = 471 |
| 98 | [M + H]+ = 444 |
| 99 | ¹H NMR (300 MHz, CDCl₃) δ 8.05-7.95 (m, 2H), 7.86-7.65 (m, 2H), 7.70-7.54 (m, 2H), 7.48-7.30 (m, 5H), 7.15-6.95 (m, 3H), 6.87 (d, J = 8.4 Hz, 1H), 3.85 (s, 3H), 3.72 (t, J = 6.5 Hz, 2H), 2.90 (t, J = 6.5 Hz, 2H), 1.97 (quint, J = 6.5 Hz, 2H).<br>[M + H]+ = 444 |
| 100 | [M + H]+ = 432 |
| 101 | ¹H NMR (300 MHz, CDCl₃) δ 8.41 (s, 1H), 7.88 (s, 1H), 7.76 (d, J = 8.7 Hz, 2H), 7.56 (d, J = 14.7 Hz, 2H), 7.36-7.29 (m, 1H), 7.25-6.93 (m, 5H), 6.87 (d, J = 8.8 Hz, 2H), 6.71 (d, J = 8.2 Hz, 1H), 5.88 (s, 1H), 3.77 (s, 3H), 3.43 (q, J = 6.0 Hz, 2H), 2.55-2.45 (m, 6H), 0.91 (t, J = 7.1 Hz, 6H)<br>[M + H]+ = 475 |
| 102 | [M + H]+ = 446 |
| 103 | [M + H]+ = 471 |

TABLE II-continued

| Ex | Characterizations |
| --- | --- |
| 104 | [M + H]⁺ = 444 |
| 105 | [M + H]⁺ = 475 |
| 106 | [M + H]⁺ = 489 |
| 107 | [M + H]⁺ = 446 |
| 108 | [M + H]⁺ = 475 |
| 109 | [M + H]⁺ = 432 |
| 110 | [M + H]⁺ = 432 |
| 111 | [M + H]⁺ = 471 |
| 112 | [M + H]⁺ = 444 |
| 113 | [M + H]⁺ = 432 |
| 114 | [M + H]⁺ = 475 |
| 115 | $^1$H NMR (300 MHz, CDCl$_3$) δ 7.85 (d, J = 8.8 Hz, 2H), 7.53 (d, J = 8.7 Hz, 2H), 7.44-7.36 (m, 2H), 7.30-7.11 (m, 2H), 7.08 (d, J = 8.8 Hz, 2H), 6.96 (d, J = 8.9 Hz, 2H), 6.09 (s, 1H), 5.83 (s, 1H), 3.87 (s, 3H), 3.45 (q, J = 7.1 Hz, 2H), 1.80-1.63 (m, 1H), 1.49 (q, J = 7.1 Hz, 2H), 0.94 (d, J = 6.6 Hz, 6H). [M + H]⁺ = 432 |
| 116 | $^1$H NMR (300 MHz, CDCl$_3$) δ 7.98 (s, 1H), 7.96 (s, 1H), 7.86 (d, J = 8.8 Hz, 2H), 7.57 (d, J = 8.7 Hz, 2H), 7.39 (s, 1H), 7.30 (t, J = 8.0 Hz, 1H), 7.13 (d, J = 8.7 Hz, 3H), 7.01 (d, J = 8.0 Hz, 1H), 6.95 (d, J = 8.8 Hz, 2H), 6.13 (s, 1H), 3.91 (s, 2H), 3.86 (s, 3H), 2.66 (q, J = 7.1 Hz, 2H), 1.14 (t, J = 7.2 Hz, 6H). [M + H]⁺ = 471 |
| 117 | [M + H]⁺ = 475 |
| 118 | [M + H]⁺ = 489 |
| 119 | [M + H]⁺ = 432 |
| 120 | [M + H]⁺ = 462 |
| 121 | [M + H]⁺ = 433 |
| 122 | [M + H]⁺ = 462 |
| 123 | $^1$H NMR (300 MHz, CDCl$_3$) δ 8.62 (s, 1H), 7.94 (d, J = 9.0 Hz, 3H), 7.54 (d, J = 8.6 Hz, 2H), 7.40 (s, 1H), 7.23 (d, J = 8.2 Hz, 2H), 7.11-6.95 (m, 4H), 6.43 (s, 1H), 3.83 (s, 2H), 2.59 (q, J = 7.1 Hz, 4H), 1.09 (t, J = 7.1 Hz, 6H). [M + H]⁺ = 525.1 |
| 124 | $^1$H NMR (300 MHz, CDCl$_3$) δ 9.74 (s, 1H), 8.23 (d, J = 7.8 Hz, 1H), 7.90 (s, 1H), 7.55 (d, J = 8.7 Hz, 2H), 7.47-7.36 (m, 2H), 7.24 (t, J = 8.0 Hz, 1H), 7.10 (d, J = 8.8 Hz, 2H), 7.09-6.94 (m, 4H), 6.63 (s, 1H), 3.99 (s, 3H), 3.82 (s, 2H), 2.56 (q, J = 7.1 Hz, 4H), 1.07 (t, J = 7.1 Hz, 6H). $^{13}$C NMR (75 MHz, CDCl$_3$) δ 163.3, 157.4, 145.9, 145.6, 138.3, 138.1, 133.5, 133.4, 132.6, 130.6, 122.2, 121.8, 121.1, 121.0, 116.0, 111.7, 111.4, 107.9, 56.4, 47.8, 46.9, 11.9. [M + H]⁺ = 471.1 |
| 125 | $^1$H NMR (300 MHz, CDCl$_3$) δ 8.27 (s, 1H), 8.01 (s, 1H), 7.91 (d, J = 7.2 Hz, 2H), 7.61 (d, J = 8.4 Hz, 2H), 7.57-7.45 (m, 3H), 7.39 (s, 1H), 7.34 (t, J = 8.2 Hz, 1H), 7.17 (d, J = 8.4 Hz, 3H), 7.05 (d, J = 8.4 Hz, 1H), 6.14 (s, 1H), 4.08 (s, 2H), 2.85 (q, J = 7.0 Hz, 4H), 1.25 (t, J = 7.0 Hz, 6H). [M + H]⁺ = 441.1 |
| 126 | $^1$H NMR (300 MHz, CDCl$_3$) δ 8.34 (s, 1H), 7.93 (s, 1H), 7.86 (d, J = 8.9 Hz, 2H), 7.69 (d, J = 8.0 Hz, 1H), 7.61 (d, J = 8.1 Hz, 1H), 7.45 (d, J = 8.5 Hz, 4H), 7.39 (s, 1H), 7.21 (s, 1H), 7.00 (d, J = 8.7 Hz, 3H), 6.93 (d, J = 8.8 Hz, 3H), 6.13 (br s, 1H), 4.06-3.94 (m, 2H), 3.85 (s, 3H), 3.47-3.34 (m, 2H), 2.14-2.01 (m, 2H). [M + H]⁺ = 470.2 |
| 137 | $^1$H NMR (300 MHz, MeOD) δ 8.68 (s, 1H), 7.60 (d, J = 8.9 Hz, 2H), 7.52-7.45 (m, 3H), 7.39 (t, J = 7.9 Hz, 1H), 7.34 (t, J = 8.1 Hz, 1H), 7.20 (d, J = 2.9 Hz, 1H), 7.17 (d, J = 9.0 Hz, 2H), 7.11 (dd, J = 8.2, 3.3 Hz, 2H), 4.22 (s, 2H), 3.85 (s, 3H), 2.94 (q, J = 7.2 Hz, 4H), 1.28 (t, J = 7.2 Hz, 6H). |
| 138 | $^1$H NMR (300 MHz, DMSO) δ 10.13 (s, 1H), 8.42 (s, 1H), 8.38 (s, 1H), 7.68 (d, J = 11.4 Hz, 4H), 7.55-7.46 (m, 2H), 7.43 (t, 1H), 7.13 (d, J = 8.8 Hz, 4H), 3.83 (s, 3H), 1.51 (s, 6H). |
| 139 | $^1$H NMR (300 MHz, MeOD) δ 8.17 (t, J = 5.6 Hz, 1H), 7.69 (d, J = 8.8 Hz, 2H), 7.59 (d, J = 8.8 Hz, 2H), 7.52-7.44 (m, 2H), 7.37 (t, J = 7.9 Hz, 1H), 7.14 (d, J = 8.8 Hz, 2H), 7.09 (dd, J = 7.8, 2.9 Hz, 1H), 7.02 (d, J = 8.8 Hz, 2H), 3.82 (s, 3H), 3.55 (t, J = 6.4 Hz, 2H), 3.40-3.29 (m, 2H), 1.67-1.51 (m, 4H), 1.47-1.37 (m, 2H). |
| 140 | $^1$H NMR (300 MHz, MeOD) δ 8.08 (s, 1H), 7.62 (d, J = 8.7 Hz, 2H), 7.55 (d, J = 8.9 Hz, 2H), 7.48 (d, J = 7.5 Hz, 2H), 7.37 (t, J = 7.9 Hz, 1H), 7.13-7.10 (d, J = 8.7 Hz, 2H), 7.10-7.06 (d, J = 8.9 Hz, 3H), 4.48 (t, J = 7.0 Hz, 2H), 3.82 (s, 3H), 3.59 (m, 2H), 2.21-2.04 (m, 2H). |

Among said compounds, compounds (1), (2), (3), (4), (8), (26), (40), (45), (46) and (61) are of particular interest.

The present invention therefore extends to compounds (1), (2), (3), (4), (8), (26), (40), (45), (46) and (61) or one of its pharmaceutically acceptable salts for use in a method for preventing, inhibiting or treating a disease in a patient exhibiting a deregulated p53.

Some of the disclosed compounds are new and form part of the present invention: (9), (16), (17), (18), (19), (20), (21), (22), (23), (24), (25), (37), (38), (39), (48), (49), (50), (52), (83), (84), (85), (86), (87), (88), (89), (90), (91), (92), (123), (124), (125) (126), (127), (128), (129), (130), (131), (132), (133), (134), (135), (136), (137), (138), (139) and (140).

The compounds of formulae (I), (Iab), (Ia), (Ib), (Ic), (Id), (Ie) and (If) can comprise one or more asymmetric carbon atoms. They can thus exist in the form of enantiomers or of diastereoisomers. These enantiomers, diastereoisomers and their mixtures, including the racemic mixtures, are encompassed within the scope of the present invention.

The compounds of the present invention can be prepared by conventional methods of organic synthesis practiced by those skilled in the art. The general reaction sequences outlined below represent a general method useful for preparing the compounds of the present invention and are not meant to be limiting in scope or utility.

The compounds of general formula (I) can be prepared according to scheme 1 below.

Scheme 1

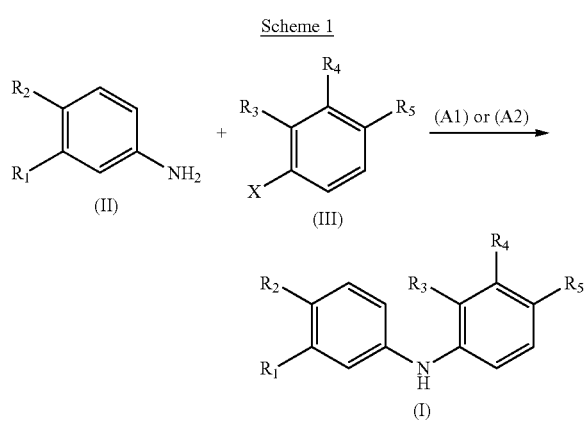

The synthesis is based on a coupling reaction starting from a halogeno aromatic compound of formula (III), wherein $R_3$, $R_4$, $R_5$ are as defined above and X is a chlorine atom, an iodine atom or a bromine atom.

According to route (A1), the compound of formula (III) is placed in a protic solvent such as tert-butanol. The compound of formula (II) is then added in a molar ratio ranging from 1 to 1.5 with respect to the compound of formula (III) in presence of an inorganic base, such as $Cs_2CO_3$ or $K_2CO_3$ in a molar ratio ranging from 1 to 2, in the presence of a diphosphine, such as Xantphos (4,5-Bis(diphenylphosphino)-9,9-dimethylxanthene) or X-Phos (2-Dicyclohexylphosphino-2',4',6'-triisopropylbiphenyl) in an amount ranging from 2 mol % to 10 mol % relative to the total amount of compound of formula (III), and in the presence of a catalyst, such as $Pd(OAc)_2$ or $Pd_2dba_3$ in an amount ranging from 2 mol % and 10 mol % relative to the total amount of compound of formula (III). The reaction mixture can then be heated at a temperature ranging from 80 to 120° C., for example at 90° C. and stirred for a time ranging from 15 to 25 hours, for example during 20 hours, under inert gas and for example argon. The reaction mixture can be concentrated under reduced pressure and the residue can be diluted with an organic solvent such as ethyl acetate. The organic phase can be washed with water, decanted and dried over magnesium sulphate. Finally, solid can be dried under vacuum overnight to give product (I).

According to route (A2), the compound of formula (III) is placed in a polar solvent such as dimethylformamide. The compound of formula (II) is then added in a molar ratio ranging from 1 to 1.5 with respect to the compound of formula (III) in presence of an inorganic base, such as $Cs_2CO_3$ or $K_2CO_3$ in a molar ratio ranging from 1 to 2, in the presence of a L-proline in an amount ranging from 10 mol % to 20 mol % relative to the total amount of compound of formula (III), and in the presence of a catalyst, such as CuI in an amount ranging from 2 mol % and 10 mol % relative to the total amount of compound of formula (III). The reaction mixture can then be heated at a temperature ranging from 60 to 120° C., for example at 80° C. and stirred for a time ranging from 24 to 72 hours, for example during 48 hours, under inert gas and for example argon. The reaction mixture can be concentrated under reduced pressure and the residue can be diluted with an organic solvent such as ethyl acetate. The organic phase can be washed with water, decanted and dried over magnesium sulphate. Finally, solid can be dried under vacuum overnight to give product (I).

The starting compounds of formula (II), (III) are available or can be prepared according to methods known to the person skilled in the art.

More particularly, compounds of formula (II) (i.e. respectively (IIa), (IIb) and (IIc)) when used to prepare compounds of formulae (Ia), (Ib) and (Ic) can be prepared according to scheme 2 below.

Preparation of (II) for (Ia), (Ib), (Ic)

Scheme 2

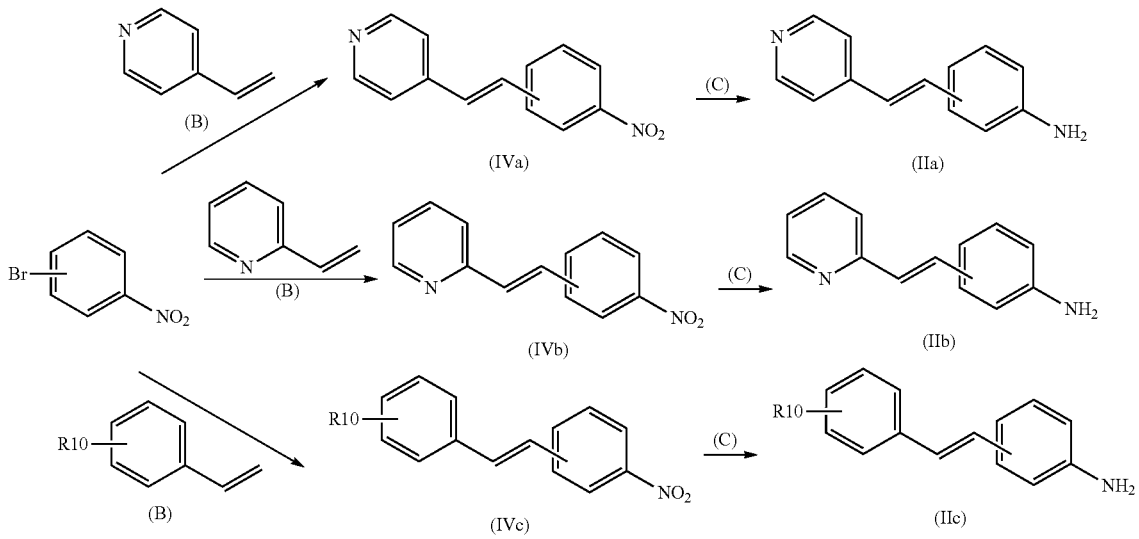

According to route (B), bromonitrobenzene is placed in a polar solvent such as dimethylformamide. Vinylpyridine or styrene is then added in a molar ratio ranging from 1 to 1.5 with respect to the bromonitrobenzene in presence of an inorganic base such as sodium acetate or potassium acetate in a molar ratio ranging from 1 to 3, in the presence of a phosphine such as triphenylphosphine in an amount ranging from 5% to 15 mol % relative to the amount of bromonitrobenzene, and in the presence of a catalyst such as $Pd(OAc)_2$ or $Pd_2dba_3$ in an amount ranging from 2% to 10% relative to the amount of bromonitrobenzene. The reaction mixture can then be heated at a temperature ranging from 80 to 140° C., for example at 135° C., and stirred for a time ranging from 15 to 30 hours for example 24 hours under inert gas for example argon. The reaction mixture can be concentrated under reduced pressure. The reaction mixture can be concentrated under reduced pressure and the residue can be diluted with an organic solvent such as ethyl acetate. The organic phase can be washed with water, decanted and dried over magnesium sulphate. Finally, solid can be dried under vacuum overnight to give product (IVa-c).

According to route (C), the compound of formula (IVa-c) and tin (II) chloride dihydrate in a ratio ranging from 3 to 8 equivalents are placed in a protic solvent such as ethanol. The reaction mixture can then be heated at a temperature ranging from 40 to 80° C., for example at 60° C. and stirred for a time ranging from 15 to 25 hours, for example during 20 hours. The mixture can be poured into 1N NaOH aqueous solution and extracted with an organic solvent such as ethyl acetate. The organic phase can be decanted and dried over magnesium sulphate. Finally, solid can be dried under vacuum overnight to give product (IIa-c).

More particularly, compounds of formula (II) (i.e. (IIc)) when R10 is trifluoromethoxy) when used to prepare compounds of formula (Ic) can be prepared according to scheme 3 below.

Preparation of (II) for (Ic) when R10=OCF$_3$

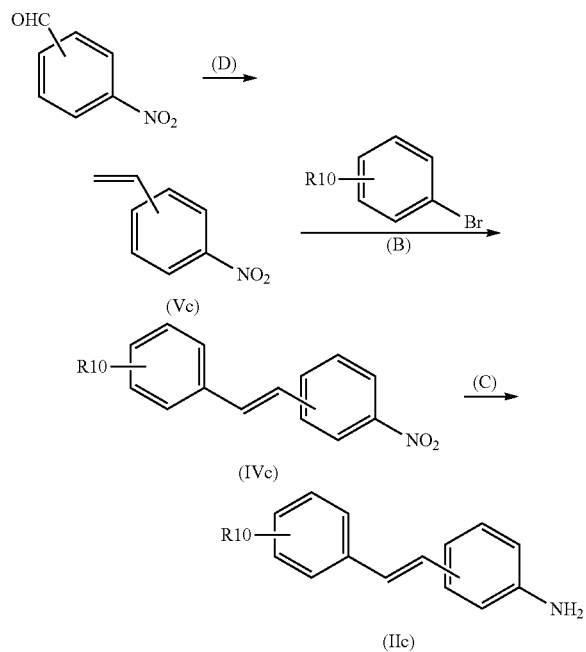

Scheme 3

(Vc)

(IVc)

(IIc)

According to route (D), methyl-triphenylphosphonium bromide in a ratio ranging from 1.5 to 3 equivalents with respect to the nitrobenzaldehyde and potassium tert-butoxide in a ratio ranging from 1.5 to 3 equivalents with respect to the nitrobenzaldehyde are placed in an aprotic solvent such as toluene. The reaction mixture can be heated at a temperature ranging from 50 to 110° C., for example at 70° C. and stirred for a time ranging from 15 to 50 minutes for example 30 minutes under an inert atmosphere of argon. Nitrobenzaldehyde is then added. The reaction mixture can then be heated at a temperature ranging from 70 to 110° C., for example at 110° C. and for a time ranging from 1 to 4 hours for example 2 hours under an inert atmosphere of argon. Upon cooling to room temperature, the reaction mixture can be diluted with water and the resulting solution can be extracted with an organic solvent such as ethyl acetate. The organic phase can be decanted and dried over magnesium sulphate. Finally, solid can be dried under vacuum overnight to give product (Vc).

The compounds of formula (II) (i.e. (IIf)), when used to prepare compounds of formula (If) can be prepared according to scheme 4 below.

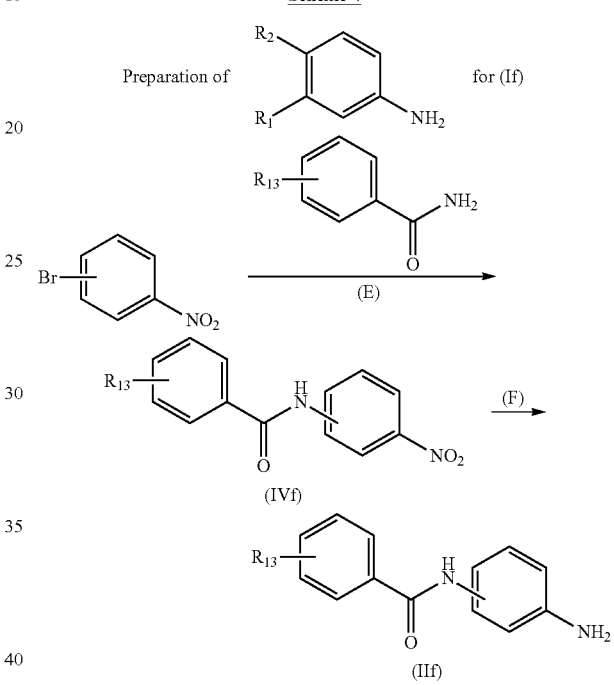

Scheme 4

Preparation of ... for (If)

(IVf)

(IIf)

According to route (E), bromonitrobenzene is placed in a protic solvent such as tert-butanol. Benzamide is then added in a molar ratio ranging from 1 to 1.5 with respect to bromonitrobenzene in presence of an inorganic base, such as Cs$_2$CO$_3$ or K$_2$CO$_3$ in a molar ratio ranging from 1 to 2, in the presence of a diphosphine, such as Xantphos (4,5-Bis(diphenylphosphino)-9,9-dimethylxanthene) or X-Phos (2-Dicyclohexylphosphino-2',4',6'-triisopropylbiphenyl) in an amount ranging from 2 mol % to 10 mol % relative to the total amount of bromonitrobenzene, and in the presence of a catalyst, such as Pd(OAc)$_2$ or Pd$_2$dba$_3$ in an amount ranging from 2 mol % and 10 mol % relative to the total amount of bromonitrobenzene. The reaction mixture can then be heated at a temperature ranging from 80 to 120° C., for example at 90° C. and stirred for a time ranging from 15 to 25 hours, for example during 20 hours, under inert gas and for example argon. The reaction mixture can be concentrated under reduced pressure and the residue can be diluted with an organic solvent such as ethyl acetate. The organic phase can be washed with water, decanted and dried over magnesium sulphate. Finally, solid can be dried under vacuum overnight to give product (IVf).

According to route (F), the compound of formula (IVf) and 10% Pd/C in a ratio ranging from 2% to 10% relative to the amount of benzamide are placed in a protic solvent such as ethanol. The reaction mixture can then be stirred for a time ranging from 2 to 18 hours for example 6 hours under an atmosphere of $H_2$. The reaction mixture can then be filtered and the filtrate can be concentrated under reduced pressure to give product (IIf).

LEGENDS OF FIGURES

FIG. 1. Effect of drugs (40), (1) and (45) on p53 pathway in MCF7 cell lines. (A) Analysis of p53 (total iso forms, blue panel) and its target gene, Δ133p53 (Δ133 forms, purple panel), at mRNA level by RT-qPCR (B) Analysis of p53 expression at protein level using 4 different antibodies. (C) Quantification of western blot (B) by densitometry using ImageJ software. (D) Analysis of p53-target genes expression by western blot. (E) Quantification of western blot (D) by densitometry using ImageJ software.

Figure 2:
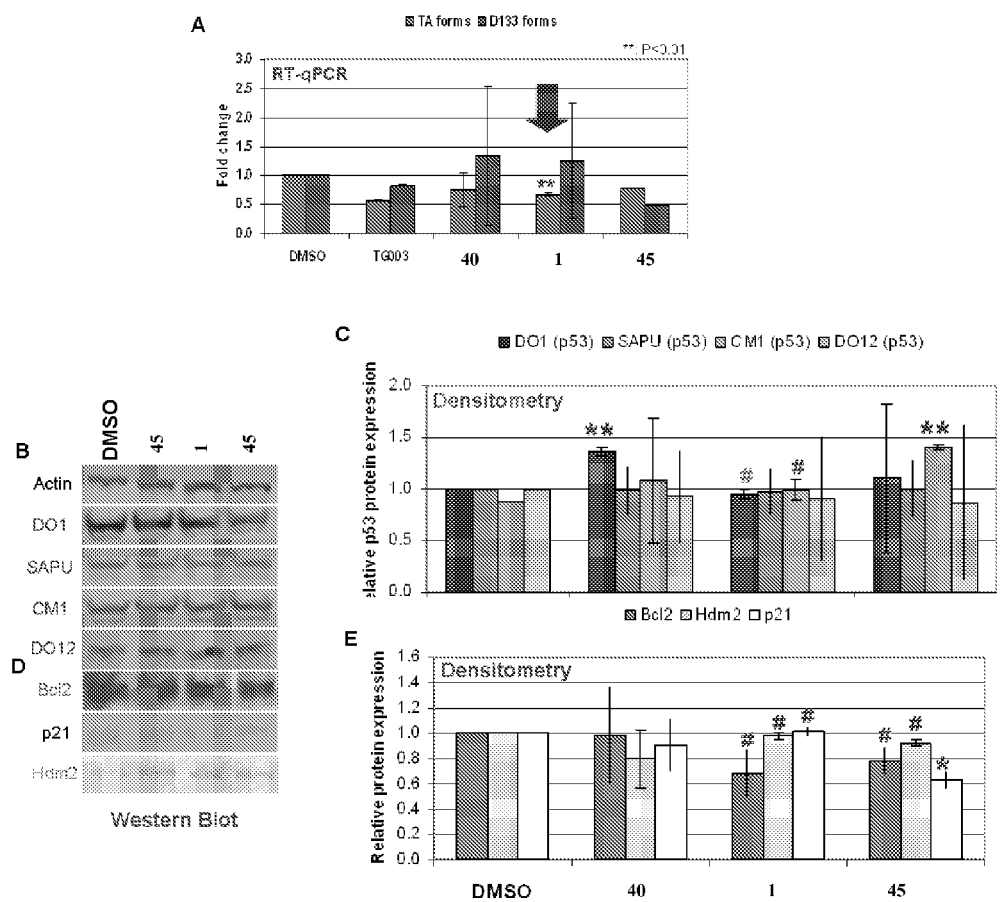

FIG. 2. Effect of drugs (40), (1) and (45) on p53 pathway in MDA-MB-231-Luc-D3H2N cell lines maintained in normal medium. (A) Analysis of p53 (TA forms, blue panel) and its target gene, Δ133p53 (Δ133 forms, purple panel), at mRNA level by RT-qPCR (B) Analysis of p53 expression at protein level using 4 different antibodies. (C) Quantification of western blot (B) by densitometry using ImageJ software. (D) Analysis of p53-target genes expression by western blot. (E) Quantification of western blot (D) by densitometry using ImageJ software.

Figure 3:
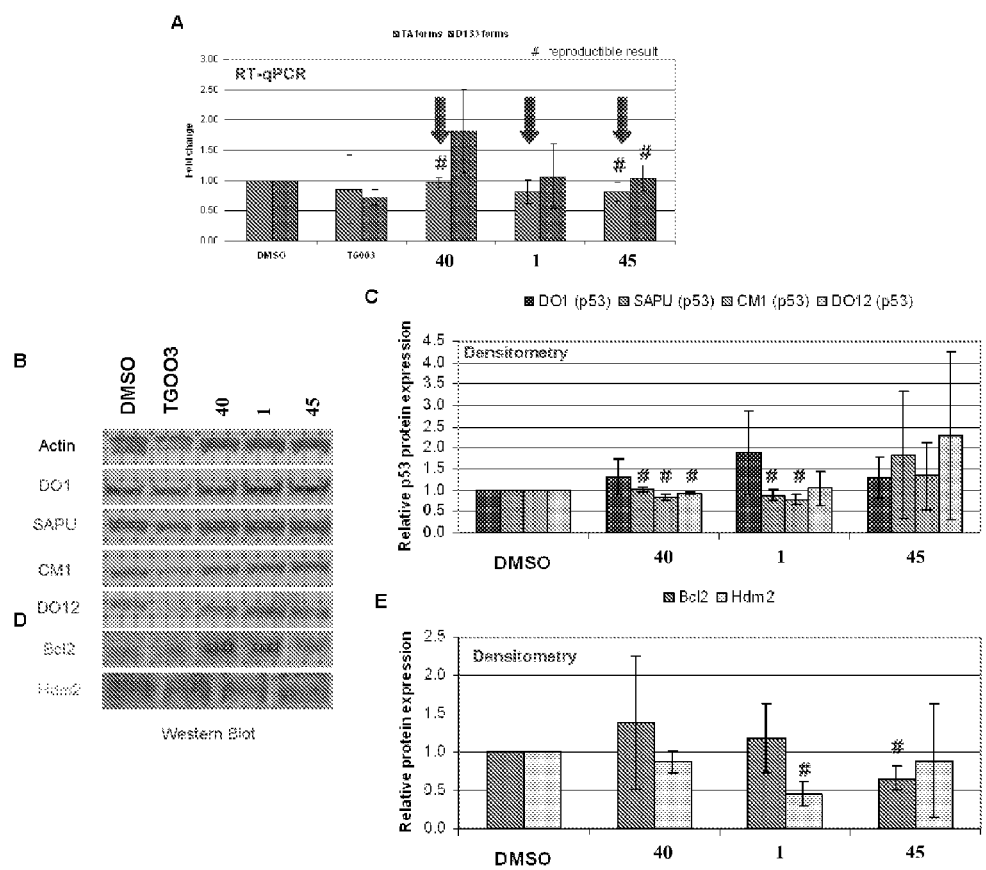

FIG. 3. Effect of drugs (40), (1) and (45) on p53 pathway in MDA-MB-231-Luc-D3H2N cell lines maintained in FCS-free medium. (A) Analysis of p53 (TA forms, blue panel) and its target gene, Δ133p53 (Δ133 forms, purple panel), at mRNA level by RT-qPCR (B) Analysis of p53 expression at protein level using 4 different antibodies. (C) Quantification of western blot (B) by densitometry using ImageJ software. (D) Analysis of p53-target genes expression by western blot. (E) Quantification of western blot (D) by densitometry using ImageJ software.

Figure 4:
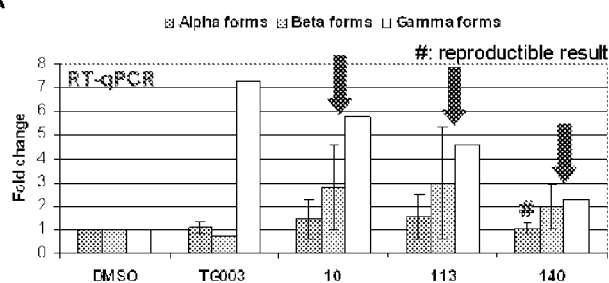
Figure 4:
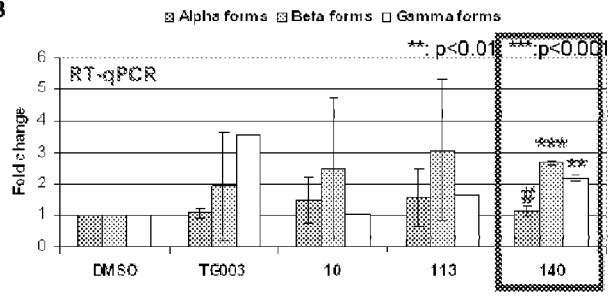
Figure 4:
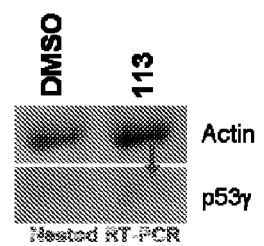
Figure 4:
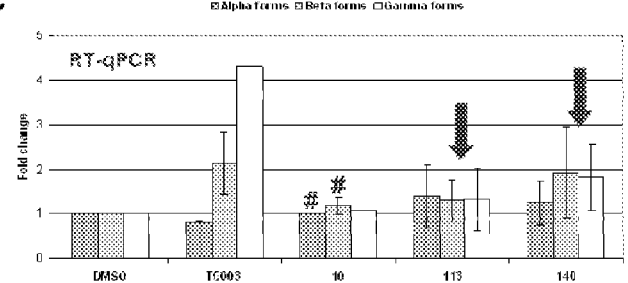
Figure 4:
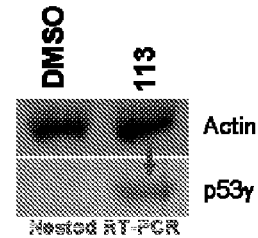

FIG. 4. Effect of drugs (40), (1) and (45) on p53 isoforms expression in MCF7 (A), MDA-MB-231-Luc-D3H2N cell lines maintained in normal medium (B) or in FCS-free medium (D). Analysis of C-terminal p53 isofroms produced by alternative splicing (a, b and g forms) at mRNA level by RT-qPCR (left panel). An example of restoration of p53g-forms expression is shown by nested RT-PCR (right panel).

The following example illustrates in detail the preparation of compounds (2), (1), (18), (9), (21), (127), (26), (40), (39), (45), (48), (49), (50), (52), (65) and (116) according to the invention and the pharmacological data.

EXAMPLES

Example 1: Compound (2) in Table I

According to route (B), 4-vinylpyridine (5.9 mL, 55 mmoles, 1.1 eq.) was placed in dimethylformamide (50 mL) with 1-bromo-3-nitrobenzene (10.1 g, 50 mmoles, 1 eq.), NaOAc (8.2 g, 100 mmoles, 2 eq.), Pd(OAc)$_2$ (561 mg, 2.5 mmoles, 5 mol %), PPh$_3$ (1.5 g, 6.0 mmoles, 12 mol %). The reaction mixture was heated at 135° C. and stirred for 24 hours under an inert atmosphere of argon. Upon cooling to room temperature, the reaction mixture was concentrated under reduced pressure and the resulting residue was partitioned between ethyl acetate and water. Upon decantation, the aqueous phase was further extracted with dichloromethane. The organic phases were gathered, dried over MgSO$_4$, filtered and concentrated under reduced pressure. The resulting residue was purified by column chromatography on silica gel to give (E)-4-[2-(3-nitrophenyl)vinyl]pyridine (6.0 g, 53%).

$^1$H NMR (300 MHz, CDCl$_3$) δ 8.63 (d, J=6.1 Hz, 2H), 8.41 (s, 1H), 8.17 (dd, J=8.2, 2.1 Hz, 1H), 7.84 (d, J=7.8 Hz, 1H), 7.57 (t, J=8.0 Hz, 1H), 7.40 (d, J=6.1 Hz, 2H), 7.34 (d, J=16.4 Hz, 1H), 7.16 (d, J=16.4 Hz, 1H).

According to route (C), (E)-4-[2-(3-nitrophenyl)vinyl]pyridine (3.0 g, 13.3 mmoles, 1 eq.) and tin (II) chloride dihydrate (15.0 g, 66.5 mmoles, 5 eq.) were placed in EtOH (130 mL). The reaction mixture was heated at 60° C. and stirred for 16 hours under an inert atmosphere of argon. The reaction mixture was then concentrated under reduced pressure and the resulting residue was diluted with ethyl acetate. The organic phase was washed with a 1N NaOH aqueous solution then with water, dried over MgSO$_4$, filtered and concentrated under reduced pressure to afford (E)-3-(2-pyridin-4-ylvinyl)phenylamine (1.9 g, 73%).

$^1$H NMR (300 MHz, CDCl$_3$) δ 8.57 (d, J=6.3 Hz, 2H), 7.35 (d, J=6.3 Hz, 2H), 7.26-7.15 (m, 2H), 7.01-6.93 (m, 2H), 6.87 (s, 1H), 6.67 (dd, J=7.9, 2.3 Hz, 1H), 3.74 (br s, 2H).

N,N-diethylpropylenediamine (7 mL, 44 mmoles, 1.1 eq.) was placed in a 3N NaOH aqueous solution (56 mL) and dichloromethane (24 mL) was added to the solution. The reaction mixture was cooled down to 0° C. with an ice bath and a solution of 3-bromobenzoyl chloride (5.3 mL, 40 mmoles, 1 eq.) in dichloromethane (40 mL) was added dropwise. The reaction mixture was then stirred at room temperature for 18 hours under an inert atmosphere of argon. Upon decantation, the organic phase was washed with water, dried over MgSO$_4$, filtered and concentrated under reduced pressure to afford 3-bromo-N-(3-diethylamino-propyl)benzamide (12.5 g, 99%).

$^1$H NMR (300 MHz, CDCl$_3$) δ 9.11 (br s, 1H), 7.90 (t, J=1.9 Hz, 1H), 7.72 (dt, J=7.9, 1.2 Hz, 1H), 7.56 (ddd, J=7.9, 1.9, 1.0 Hz, 1H), 7.26 (t, J=7.9 Hz, 1H), 3.53 (dt, J=5.7, 4.6 Hz, 2H), 2.64-2.51 (m, 6H), 1.73 (quint, J=5.7 Hz, 2H), 1.02 (t, J=7.2 Hz, 6H).

According to route (A1), a reaction mixture of 3-bromo-N-(3-diethylamino-propyl)benzamide (1.4 g, 4.6 mmoles, 1 eq.), (E)-3-(2-pyridin-4-ylvinyl)phenylamine (1 g, 5.1 mmoles, 1.1 eq.), Pd$_2$(dba)$_3$ (211 mg, 0.23 mmole, 5 mol %), XPhos (219 mg, 0.46 mmole, 10 mol %) and K$_2$CO$_3$ (2.6 g, 18.4 mmoles, 4 eq.) in t-BuOH (6.3 mL) was heated at 80° C. and stirred for 20 hours under an inert atmosphere of argon. The reaction mixture was then concentrated under reduced pressure and the resulting residue was diluted with ethyl acetate. The organic phase was washed with water, dried over MgSO$_4$, filtered and concentrated under reduced pressure. The resulting residue was purified by column chromatography on alumina to give (E)-N-(3-diethylamino-propyl)-3-[3-(2-pyridin-4-ylvinyl)phenylamino]benzamide (2) (1.15 g, 58%).

$^1$H NMR (300 MHz, CDCl$_3$) δ 8.70 (s, 1H), 8.51 (d, J=4.9 Hz, 2H), 7.61 (s, 1H), 7.30-7.14 (m, 8H), 7.08-7.00 (m, 2H), 6.89 (d, J=16.4 Hz, 1H), 6.58 (s, 1H), 3.52-3.48 (m, 2H), 2.59-2.40 (m, 6H), 1.69-1.65 (m, 2H), 0.95 (t, J=7.1 Hz, 6H).

$^{13}$C NMR (75 MHz, CDCl$_3$) δ 167.1, 150.3, 144.7, 143.6, 143.5, 137.6, 136.5, 133.3, 130.0, 129.4, 126.3, 121.1, 120.3, 120.2, 119.1, 118.8, 117.1, 116.9, 53.4, 46.9, 41.4, 25.0, 11.6.

[M+H]$^+$=429.2

Example 2: Compound (1) in Table I

According to route (B), 4-vinylpyridine (2.35 mL, 22 mmoles, 1.1 eq.) was placed in dimethylformamide (20 mL)

with 1-bromo-3-nitrobenzene (4 g, 20 mmoles, 1 eq.), NaOAc (3.3 g, 40 mmoles, 2 eq.), Pd(OAc)$_2$ (225 mg, 1 mmole, 5 mol %), PPh$_3$ (629 mg, 2.4 mmoles, 12 mol %). The reaction mixture was heated at 135° C. and stirred for 24 hours under an inert atmosphere of argon. Upon cooling to room temperature, the reaction mixture was concentrated under reduced pressure and the resulting residue was partitioned between ethyl acetate and water. Upon decantation, the organic phase was further washed with water, dried over MgSO$_4$, filtered and concentrated under reduced pressure to give (E)-4-[2-(3-nitrophenyl)vinyl]pyridine (2.9 g, 65%).

$^1$H NMR (300 MHz, CDCl$_3$) δ 8.64 (d, J=4.8 Hz, 2H), 8.41 (s, 1H), 8.17 (dd, J=8.2, 1.1 Hz, 1H), 7.84 (d, J=7.8 Hz, 1H), 7.58 (t, J=8.0 Hz, 1H), 7.40 (d, J=5.7 Hz, 2H), 7.34 (d, J=16.4 Hz, 1H), 7.16 (d, J=16.4 Hz, 1H).

According to route (C), (E)-4-[2-(3-nitrophenyl)vinyl]pyridine (910 mg, 4 mmoles, 1 eq.) and tin (II) chloride dihydrate (4.5 g, 20 mmoles, 5 eq.) were placed in EtOH (40 mL). The reaction mixture was heated at 60° C. and stirred for 16 hours under an inert atmosphere of argon. The reaction mixture was then concentrated under reduced pressure and the resulting residue was diluted with ethyl acetate. The organic phase was washed with a 1N NaOH aqueous solution then with water, dried over MgSO$_4$, filtered and concentrated under reduced pressure to afford (E)-3-(2-pyridin-4-ylvinyl)phenylamine (763 mg, 97%).

$^1$H NMR (300 MHz, CDCl$_3$) δ 8.57 (d, J=5.9 Hz, 2H), 7.35 (d, J=5.9 Hz, 2H), 7.26-7.14 (m, 2H), 7.01-6.92 (m, 2H), 6.87 (s, 1H), 6.67 (dd, J=7.9, 1.4 Hz, 2H), 3.74 (br s, 2H).

3-methyl-1-butanamine (2.5 mL, 22 mmoles, 1.1 eq.) was placed in a 3N NaOH aqueous solution (15 mL) and dichloromethane (5 mL) was added to the solution. The reaction mixture was cooled down to 0° C. with an ice bath and a solution of 3-bromobenzoyl chloride (2.6 mL, 20 mmoles, 1 eq.) in dichloromethane (5 mL) was added dropwise. The reaction mixture was then stirred at room temperature for 18 hours under an inert atmosphere of argon. Upon decantation, the organic phase was washed with water, dried over MgSO$_4$, filtered and concentrated under reduced pressure to afford 3-bromo-N-(3-methylbutyl)benzamide (5.4 g, 100%).

$^1$H NMR (300 MHz, CDCl$_3$) δ 7.89 (s, 1H), 7.67 (d, J=7.9 Hz, 1H), 7.60 (d, J=7.9 Hz, 1H), 7.29 (d, J=7.9 Hz, 1H), 6.24 (br s, 1H), 3.45 (q, J=7.0 Hz, 2H), 1.66 (heptuplet, J=6.6 Hz, 1H), 1.50 (q, J=7.0 Hz, 2H), 0.94 (d, J=6.6 Hz, 6H).

According to route (A1), a reaction mixture of 3-bromo-N-(3-methylbutyl)benzamide (373 mg, 1.38 mmole, 1 eq.), (E)-3-(2-pyridin-4-ylvinyl)phenylamine (300 mg, 1.53 mmole, 1.1 eq.), Pd$_2$(dba)$_3$ (63 mg, 69 moles, 5 mol %), XPhos (66 mg, 138 moles, 10 mol %) and K$_2$CO$_3$ (763 mg, 5.52 mmoles, 4 eq.) in t-BuOH (1.7 mL) was heated at 90° C. and stirred for 20 hours under an inert atmosphere of argon. The reaction mixture was then concentrated under reduced pressure and the resulting residue was diluted with ethyl acetate. The organic phase was washed with water, dried over MgSO$_4$, filtered and concentrated under reduced pressure. The resulting residue was purified by column chromatography on silica gel to give (E)-N-(3-methylbutyl)-3-[3-(2-pyridin-4-ylvinyl)phenylamino]benzamide (1) (333 mg, 63%).

$^1$H NMR (300 MHz, DMSO-d6) δ 8.52 (d, J=5.7 Hz, 2H), 8.39 (s, 1H), 8.35-8.30 (m, 1H), 7.55 (d, J=6.0 Hz, 2H), 7.50 (d, J=16.7 Hz, 1H), 7.32-7.27 (m, 5H), 7.20 (d, J=7.6 Hz, 2H), 7.15 (d, J=11.4 Hz, 1H), 7.05 (d, J=8.2 Hz, 1H), 3.22 (q, J=6.9 Hz, 2H), 1.58 (heptuplet, J=6.6 Hz, 1H), 1.37 (q, J=6.9 Hz, 2H), 0.87 (d, J=6.6 Hz, 6H).

$^{13}$C NMR (75 MHz, DMSO-d6) δ 166.3, 150.0, 143.6, 143.4, 137.2, 136.1, 133.3, 129.7, 129.1, 125.8, 120.9, 119.0, 118.8, 118.2, 117.5, 115.8, 115.6, 38.1, 37.4, 25.3, 22.5.

[M+H]$^+$=386.2

Example 3: Compound (18) in Table I

According to route (B), 4-vinylpyridine (6.4 mL, 59.9 mmoles, 1.1 eq.) was placed in dimethylformamide (55 mL) with 1-bromo-3-nitrobenzene (11 g, 54.4 mmoles, 1 eq.), NaOAc (9 g, 108.8 mmoles, 2 eq.), Pd(OAc)$_2$ (610 mg, 2.7 mmoles, 5 mol %), PPh$_3$ (1.4 g, 5.4 mmoles, 10 mol %). The reaction mixture was heated at 135° C. and stirred for 24 hours under an inert atmosphere of argon. Upon cooling to room temperature, the reaction mixture was concentrated under reduced pressure and the resulting residue was partitioned between ethyl acetate and water. Upon decantation, the organic phase was further washed with water, dried over MgSO$_4$, filtered and concentrated under reduced pressure. The resulting residue was purified by column chromatography on silica gel to give (E)-4-[2-(3-nitrophenyl)vinyl]pyridine (7.9 g, 64%).

$^1$H NMR (300 MHz, CDCl$_3$) δ 8.61 (d, J=5.0 Hz, 2H), 8.38 (s, 1H), 8.15 (d, J=8.1 Hz, 1H), 7.82 (d, J=7.6 Hz, 1H), 7.56 (t, J=7.9 Hz, 1H), 7.38 (d, J=5.0 Hz, 2H), 7.32 (d, J=16.4 Hz, 1H), 7.14 (d, J=16.4 Hz, 1H).

According to route (C), (E)-4-[2-(3-nitrophenyl)vinyl]pyridine (7.9 g, 35 mmoles, 1 eq.) and tin (II) chloride dihydrate (39 g, 175 mmoles, 5 eq.) were placed in EtOH (350 mL). The reaction mixture was heated at 60° C. and stirred for 48 hours under an inert atmosphere of argon. The reaction mixture was then concentrated under reduced pressure and the resulting residue was diluted with ethyl acetate. The organic phase was washed with a 1N NaOH aqueous solution then with water, dried over MgSO$_4$, filtered and concentrated under reduced pressure to afford (E)-3-(2-pyridin-4-ylvinyl)phenylamine (5.2 g, 76%).

$^1$H NMR (300 MHz, CDCl$_3$) δ 8.57 (d, J=6.3 Hz, 2H), 7.35 (d, J=6.3 Hz, 2H), 7.30-7.16 (m, 2H), 7.03-6.91 (m, 2H), 6.86 (s, 1H), 6.72-6.60 (m, 1H), 3.74 (br s, 2H).

3-bromobenzenesulfonyl chloride (0.56 mL, 3.9 mmoles, 1 eq.) and N,N-diisopropylethylamine (1.02 mL, 5.9 mmoles, 1.5 eq.) were placed in anhydrous dichloromethane (20 mL). The reaction mixture was cooled down to 0° C. with an ice bath and N,N-diethylpropylenediamine (1.23 mL, 7.8 mmoles, 2 eq.) was added dropwise. The reaction mixture was then stirred at 0° C. for 2 hours under an inert atmosphere of argon. The mixture was washed with saturated aqueous solutions of NH$_4$Cl and then NaCl. The aqueous phases were extracted with dichloromethane. The organic phases were gathered, dried over MgSO$_4$, filtered and concentrated under reduced pressure to afford 3-bromo-N-(3-diethylaminopropyl)benzenesulfonamide (524 mg, 38%).

$^1$H NMR (300 MHz, CDCl$_3$) δ 7.98 (s, 1H), 7.78 (d, J=7.9 Hz, 1H), 7.66 (d, J=7.9 Hz, 1H), 7.37 (t, J=7.9 Hz, 1H), 3.12-2.96 (m, 2H), 2.67-2.43 (m, 6H), 1.77-1.58 (m, 2H), 1.06 (t, J=7.1 Hz, 6H).

According to route (A1), a reaction mixture of 3-bromo-N-(3-diethylaminopropyl)benzenesulfonamide (175 mg, 0.50 mmole, 1 eq.), (E)-3-(2-pyridin-4-ylvinyl)phenylamine (108 mg, 0.55 mmole, 1.1 eq.), Pd$_2$(dba)$_3$ (23 mg, 0.025 mmole, 5 mol %), XPhos (24 mg, 0.05 mmole, 10 mol %) and K$_2$CO$_3$ (276 mg, 2 mmoles, 4 eq.) in t-BuOH (2 mL) was heated at 90° C. and stirred for 20 hours under an inert atmosphere of argon. The reaction mixture was then concentrated under reduced pressure and the resulting residue was diluted with ethyl acetate. The organic phase was washed with water, dried over MgSO$_4$, filtered and concentrated under reduced pressure. The resulting residue was purified by column chromatography on silica gel to give N-(3-diethylaminopropyl)-3-[3-(2-pyridin-4-ylvinyl)phenylamino]benzenesulfonamide (18) (100 mg, 43%).

$^1$H NMR (300 MHz, CDCl$_3$) δ 8.55 (d, J=5.8 Hz, 2H), 7.58 (s, 1H), 7.39-7.32 (m, 4H), 7.31-7.19 (m, 4H), 7.15 (d, J=7.7 Hz, 1H), 7.10 (d, J=7.9 Hz, 1H), 6.98 (d, J=16.3 Hz, 1H), 6.64 (d, J=8.4 Hz, 1H), 3.15-3.00 (m, 2H), 2.52-2.35 (m, 6H), 1.68-1.53 (m, 2H), 0.96 (t, J=7.1 Hz, 6H).

[M+H]$^+$=465.2

Example 4: Compound (9) in Table I

According to route (B), 4-vinylpyridine (5.9 mL, 55 mmoles, 1.1 eq.) was placed in dimethylformamide (50 mL) with 1-bromo-3-nitrobenzene (10.1 g, 50 mmoles, 1 eq.), NaOAc (8.2 g, 100 mmoles, 2 eq.), Pd(OAc)$_2$ (561 mg, 2.5 mmoles, 5 mol %), PPh$_3$ (1.5 g, 6.0 mmoles, 12 mol %). The reaction mixture was heated at 135° C. and stirred for 24 hours under an inert atmosphere of argon. Upon cooling to room temperature, the reaction mixture was concentrated under reduced pressure and the resulting residue was partitioned between ethyl acetate and water. Upon decantation, the aqueous phase was further extracted with dichloromethane. The organic phases were gathered, dried over MgSO$_4$, filtered and concentrated under reduced pressure. The resulting residue was purified by column chromatography on silica gel to give (E)-4-[2-(3-nitrophenyl)vinyl]pyridine (6.0 g, 53%).

$^1$H NMR (300 MHz, CDCl$_3$) δ 8.63 (d, J=6.1 Hz, 2H), 8.41 (s, 1H), 8.17 (dd, J=8.2, 2.1 Hz, 1H), 7.84 (d, J=7.8 Hz, 1H), 7.57 (t, J=8.0 Hz, 1H), 7.40 (d, J=6.1 Hz, 2H), 7.34 (d, J=16.4 Hz, 1H), 7.16 (d, J=16.4 Hz, 1H).

According to route (C), (E)-4-[2-(3-nitrophenyl)vinyl] pyridine (3.0 g, 13.3 mmoles, 1 eq.) and tin (II) chloride dihydrate (15.0 g, 66.5 mmoles, 5 eq.) were placed in EtOH (130 mL). The reaction mixture was heated at 60° C. and stirred for 16 hours under an inert atmosphere of argon. The reaction mixture was then concentrated under reduced pressure and the resulting residue was diluted with ethyl acetate. The organic phase was washed with a 1N NaOH aqueous solution then with water, dried over MgSO$_4$, filtered and concentrated under reduced pressure to afford (E)-3-(2-pyridin-4-ylvinyl)phenylamine (1.9 g, 73%).

$^1$H NMR (300 MHz, CDCl$_3$) δ 8.57 (d, J=6.3 Hz, 2H), 7.35 (d, J=6.3 Hz, 2H), 7.26-7.15 (m, 2H), 7.01-6.93 (m, 2H), 6.87 (s, 1H), 6.67 (dd, J=7.9, 2.3 Hz, 1H), 3.74 (br s, 2H).

NH4OH solution (5.8 mL) was placed in water (24 mL) at −10° C. 3-bromobenzoyl chloride (10 mmol, 1.3 mL) was placed in tetrahydrofurane (8 mL) and added to the aqueous solution. The mixture was stirred for 1 hour at −10° C. The reaction mixture was filtered and further washed with water to give 3-beomo-benzamide (1.7 g, 85%).

$^1$H NMR (300 MHz, MeOD) δ 8.04 (s, 1H), 7.84 (d, J=7.0 Hz, 1H), 7.70 (d, J=6.6 Hz, 1H), 7.40-7.38 (t, J=6.8 Hz, 1H).

According to route (A1), a reaction mixture of 3-bromo-benzamide (99 mg, 0.5 mmoles, 1 eq.), (E)-3-(2-pyridin-4-ylvinyl)phenylamine (108 mg, 0.55 mmoles, 1.1 eq.), Pd$_2$(dba)$_3$ (23 mg, 0.025 mmole, 5 mol %), XPhos (143 mg, 0.05 mmole, 10 mol %) and K$_2$CO$_3$ (276 mg, 2.0 mmoles, 4 eq.) in t-BuOH (2.0 mL) was heated at 90° C. and stirred for 20 hours under an inert atmosphere of argon. The reaction mixture was then concentrated under reduced pressure and the resulting residue was partitioned between ethyl acetate and water. Upon decantation, the aqueous phase was further extracted with dichloromethane. The organic phases were gathered, dried over MgSO$_4$, filtered and concentrated under reduced pressure. The resulting residue was purified by column chromatography on silica gel to give 3-[3-(2-pyridin-4-ylvinyl)phenylamino]benzamide (9) (100 mg, 63%).

$^1$H NMR (300 MHz, MeOD) δ 8.46 (d, J=6.2 Hz, 1H), 7.62 (s, 1H), 7.57 (d, J=6.1 Hz, 1H), 7.46 (d, J=16.1 Hz, 1H), 7.38-7.30 (m, 2H), 7.28 (d, J=8.1 Hz, 1H), 7.18 (d, J=7.8 Hz, 1H), 7.16-7.07 (m, 1H).

[M+H]+=314.0

Example 5: Compound (21) in Table I

According to route (B), 4-vinylpyridine (5.9 mL, 55 mmoles, 1.1 eq.) was placed in dimethylformamide (50 mL) with 1-bromo-3-nitrobenzene (10.1 g, 50 mmoles, 1 eq.), NaOAc (8.2 g, 100 mmoles, 2 eq.), Pd(OAc)$_2$ (561 mg, 2.5 mmoles, 5 mol %), PPh$_3$ (1.5 g, 6.0 mmoles, 12 mol %). The reaction mixture was heated at 135° C. and stirred for 24 hours under an inert atmosphere of argon. Upon cooling to room temperature, the reaction mixture was concentrated under reduced pressure and the resulting residue was partitioned between ethyl acetate and water. Upon decantation, the aqueous phase was further extracted with dichloromethane. The organic phases were gathered, dried over MgSO$_4$, filtered and concentrated under reduced pressure. The resulting residue was purified by column chromatography on silica gel to give (E)-4-[2-(3-nitrophenyl)vinyl]pyridine (6.0 g, 53%).

$^1$H NMR (300 MHz, CDCl$_3$) δ 8.63 (d, J=6.1 Hz, 2H), 8.41 (s, 1H), 8.17 (dd, J=8.2, 2.1 Hz, 1H), 7.84 (d, J=7.8 Hz, 1H), 7.57 (t, J=8.0 Hz, 1H), 7.40 (d, J=6.1 Hz, 2H), 7.34 (d, J=16.4 Hz, 1H), 7.16 (d, J=16.4 Hz, 1H).

According to route (C), (E)-4-[2-(3-nitrophenyl)vinyl] pyridine (3.0 g, 13.3 mmoles, 1 eq.) and tin (II) chloride dihydrate (15.0 g, 66.5 mmoles, 5 eq.) were placed in EtOH (130 mL). The reaction mixture was heated at 60° C. and stirred for 16 hours under an inert atmosphere of argon. The reaction mixture was then concentrated under reduced pressure and the resulting residue was diluted with ethyl acetate. The organic phase was washed with a 1N NaOH aqueous solution then with water, dried over MgSO$_4$, filtered and concentrated under reduced pressure to afford (E)-3-(2-pyridin-4-ylvinyl)phenylamine (1.9 g, 73%).

$^1$H NMR (300 MHz, CDCl$_3$) δ 8.57 (d, J=6.3 Hz, 2H), 7.35 (d, J=6.3 Hz, 2H), 7.26-7.15 (m, 2H), 7.01-6.93 (m, 2H), 6.87 (s, 1H), 6.67 (dd, J=7.9, 2.3 Hz, 1H), 3.74 (br s, 2H). 3-(4-methyl-piperazinyl)-propylamine (1.9 mL, 11 mmoles, 1.1 eq.) was placed in a 3N NaOH aqueous solution (14 mL) and dichloromethane (2 mL) was added to the solution. The reaction mixture was cooled down to 0° C. with an ice bath and a solution of 3-bromobenzoyl chloride (1.9 mL, 10 mmoles, 1 eq.) in dichloromethane (14 mL) was added dropwise. The reaction mixture was then stirred at room temperature for 18 hours under an inert atmosphere of argon. Upon decantation, the organic phase was washed with water, dried over MgSO$_4$, filtered and concentrated under reduced pressure to afford 3-bromo-N-[3-(4-methyl-piperarinyl)]-propylamine (2.8 g, 85%).

$^1$H NMR (300 MHz, CDCl$_3$) δ 8.59 (s, 1H), 7.90 (s, 1H), 7.79 (d, J=8.4 Hz, 1H), 7.59 (d, J=7.9 Hz, 1H), 7.28 (t, J=8.2 Hz, 1H), 3.54 (d, J=4.7 Hz, 2H), 2.63-2.50 (m, 4H), 2.46 (broad s, 4H), 2.30 (s, 5H), 1.89-1.54 (m, 2H).

According to route (A1), a reaction mixture of 3-bromo-N-[3-(4-methyl-piperarinyl)]-propylamine (169 mg, 0.50 mmoles, 1 eq.), (E)-3-(2-pyridin-4-ylvinyl)phenylamine (108 mg, 0.55 mmoles, 1.1 eq.), Pd$_2$(dba)$_3$ (23 mg, 0.025 mmole, 5 mol %), XPhos (24 mg, 0.05 mmole, 10 mol %) and K$_2$CO$_3$ (276 mg, 2.0 mmoles, 4 eq.) in t-BuOH (2 mL) was heated at 80° C. and stirred for 20 hours under an inert atmosphere of argon. The reaction mixture was then concentrated under reduced pressure and the resulting residue was diluted with ethyl acetate. The organic phase was washed with water, dried over MgSO$_4$, filtered and concentrated under reduced pressure. The resulting residue was purified by column chromatography on alumina to give (E)-3-(4-methyl-piperazinyl)-propyl)-3-[3-(2-pyridin-4-yl-vinyl)-phenylamino]-benzamide (21) (115 mg, 51%).

$^1$H NMR (300 MHz, CDCl$_3$) δ 8.49 (d, J=3.6 Hz, 2H), 8.23 (s, 1H), 7.56 (s, 1H), 7.39-7.11 (m, 7H), 7.14-6.98 (m, 3H), 6.90 (d, J=15.8 Hz, 1H), 6.53 (s, 1H), 3.49 (s, 2H), 3.23 (s, 2H), 2.2.5-2.30 (m, 8H), 2.20 (s, 3H), 1.75-1.70 (m, 2H).

$^{13}$C NMR (75 MHz, CDCl3) δ 167.47, 150.25, 144.65, 143.65, 143.38, 137.49, 136.43, 133.24, 129.95, 129.35, 126.26, 121.02, 120.13, 119.99, 119.17, 118.56, 117.07, 116.68, 58.36, 55.12, 53.37, 46.13, 40.93, 24.40.

[M+H]+=456.2

Example 6: Compound (127) in Table I

According to route (B), 4-vinylpyridine (5.9 mL, 55 mmoles, 1.1 eq.) was placed in dimethylformamide (50 mL) with 1-bromo-3-nitrobenzene (10.1 g, 50 mmoles, 1 eq.), NaOAc (8.2 g, 100 mmoles, 2 eq.), Pd(OAc)$_2$ (561 mg, 2.5 mmoles, 5 mol %), PPh$_3$ (1.5 g, 6.0 mmoles, 12 mol %). The reaction mixture was heated at 135° C. and stirred for 24 hours under an inert atmosphere of argon. Upon cooling to room temperature, the reaction mixture was concentrated under reduced pressure and the resulting residue was partitioned between ethyl acetate and water. Upon decantation, the aqueous phase was further extracted with dichloromethane. The organic phases were gathered, dried over MgSO$_4$, filtered and concentrated under reduced pressure. The resulting residue was purified by column chromatography on silica gel to give (E)-4-[2-(3-nitrophenyl)vinyl]pyridine (6.0 g, 53%).

$^1$H NMR (300 MHz, CDCl$_3$) δ 8.63 (d, J=6.1 Hz, 2H), 8.41 (s, 1H), 8.17 (dd, J=8.2, 2.1 Hz, 1H), 7.84 (d, J=7.8 Hz, 1H), 7.57 (t, J=8.0 Hz, 1H), 7.40 (d, J=6.1 Hz, 2H), 7.34 (d, J=16.4 Hz, 1H), 7.16 (d, J=16.4 Hz, 1H).

According to route (C), (E)-4-[2-(3-nitrophenyl)vinyl]pyridine (3.0 g, 13.3 mmoles, 1 eq.) and tin (II) chloride dihydrate (15.0 g, 66.5 mmoles, 5 eq.) were placed in EtOH (130 mL). The reaction mixture was heated at 60° C. and stirred for 16 hours under an inert atmosphere of argon. The reaction mixture was then concentrated under reduced pressure and the resulting residue was diluted with ethyl acetate. The organic phase was washed with a 1N NaOH aqueous solution then with water, dried over MgSO$_4$, filtered and concentrated under reduced pressure to afford (E)-3-(2-pyridin-4-ylvinyl)phenylamine (1.9 g, 73%).

$^1$H NMR (300 MHz, CDCl$_3$) δ 8.57 (d, J=6.3 Hz, 2H), 7.35 (d, J=6.3 Hz, 2H), 7.26-7.15 (m, 2H), 7.01-6.93 (m, 2H), 6.87 (s, 1H), 6.67 (dd, J=7.9, 2.3 Hz, 1H), 3.74 (br s, 2H).

According to route (A1), a reaction mixture of 3-bromo-benzenesulfonamide (118 mg, 0.50 mmoles, 1 eq.), (E)-3-(2-pyridin-4-ylvinyl)phenylamine (108 mg, 0.55 mmoles, 1.1 eq.), Pd$_2$(dba)$_3$ (23 mg, 0.025 mmole, 5 mol %), XPhos (24 mg, 0.05 mmole, 10 mol %) and K$_2$CO$_3$ (276 mg, 2.0 mmoles, 4 eq.) in t-BuOH (2 mL) was heated at 80° C. and stirred for 20 hours under an inert atmosphere of argon. The reaction mixture was then concentrated under reduced pressure and the resulting residue was diluted with ethyl acetate. The organic phase was washed with water, dried over MgSO$_4$, filtered and concentrated under reduced pressure. The resulting residue was purified by column chromatography on alumina to give (E)-3-[3-(2-pyridin-4-ylvinyl)phenylamino]-benzenesulfonamide (127) (89 mg, 51%).

$^1$H NMR (300 MHz, MeOD) δ 8.43 (s, 2H), 7.67 (s, 1H), 7.53 (d, J=5.2 Hz, 2H), 7.42 (d, J=16.5 Hz, 1H), 7.38-7.13 (m, 8H), 7.13-7.07 (m, 1H), 7.09 (d, J=16.5 Hz, 1H).

[M+H]+=352.1

Example 7: Compound (26) in Table I

According to route (B), 2-vinylpyridine (1.18 mL, 11 mmoles, 1.1 eq.) was placed in dimethylformamide (10 mL) with 1-bromo-3-nitrobenzene (2.02 g, 10 mmoles, 1 eq.), NaOAc (1.64 g, 20 mmoles, 2 eq.), Pd(OAc)$_2$ (112 mg, 0.5 mmole, 5 mol %), PPh$_3$ (315 mg, 1.2 mmole, 12 mol %). The reaction mixture was heated at 135° C. and stirred for 24 hours under an inert atmosphere of argon. Upon cooling to room temperature, the reaction mixture was concentrated under reduced pressure and the resulting residue was partitioned between ethyl acetate and water. Upon decantation, the organic phase was further washed with water, dried over MgSO$_4$, filtered and concentrated under reduced pressure. The resulting residue was purified by column chromatography on silica gel to give (E)-2-[2-(3-nitrophenyl)vinyl]pyridine (1.0 g, 44%).

$^1$H NMR (300 MHz, CDCl$_3$) δ 8.64 (d, J=4.6 Hz, 1H), 8.44 (s, 1H), 8.14 (ddd, J=8.2, 2.1, 0.9 Hz, 1H), 7.86 (d, J=7.7 Hz, 1H), 7.77-7.65 (m, 2H), 7.55 (t, J=8.0 Hz, 1H), 7.41 (d, J=7.9 Hz, 1H), 7.28 (d, J=16.0 Hz, 1H), 7.22 (ddd, J=7.5, 4.8, 1.0 Hz, 1H).

According to route (C), (E)-2-[2-(3-nitrophenyl)vinyl]pyridine (1.0 g, 4.4 mmoles, 1 eq.) and tin (II) chloride dihydrate (5.0 g, 22.1 mmoles, 5 eq.) were placed in EtOH (44 mL). The reaction mixture was heated at 60° C. and stirred for 16 hours under an inert atmosphere of argon. The reaction mixture was then concentrated under reduced pressure and the resulting residue was diluted with ethyl acetate. The organic phase was washed with a 1N NaOH aqueous solution then with water, dried over MgSO$_4$, filtered and concentrated under reduced pressure to afford (E)-3-(2-pyridin-2-ylvinyl)phenylamine (816 mg, 94%).

$^1$H NMR (300 MHz, CDCl$_3$) δ 8.58 (dd, J=4.8, 0.7 Hz, 1H), 7.60 (td, J=7.7, 1.8 Hz, 1H), 7.53 (d, J=16.1 Hz, 1H), 7.33 (d, J=7.9 Hz, 1H), 7.18-7.05 (m, 3H), 6.97 (d, J=7.7 Hz, 1H), 6.86 (s, 1H), 6.61 (dd, J=7.9, 1.4 Hz, 1H), 3.76 (br s, 1H).

Pent-4-yn-1-ol (5 g, 59 mmoles, 1.0 eq.) was placed in a dimethylsulfoxide (65 mL) and water (5 mL) solution, together with 1-bromo-4-iodobenzene (16.81 g, 59 mmoles, 1 eq.), NaN$_3$ (4.64 g, 71.3 mmoles, 1.2 eq.), L-Proline (1.53 g, 11.8 mmoles, 0.2 eq.), Na$_2$CO$_3$ (1.26 g, 11.8 mmoles, 0.2 eq.), sodium ascorbate (3.57 g, 23.7 mmoles, 0.4 eq.). CuSO$_4$.5H$_2$O (4.7 g, 11.8 mmoles, 0.2 eq.) was added and the reaction mixture was heated at 65° C. and stirred for 16 hours under an inert atmosphere of argon. Upon cooling to room temperature, the reaction mixture was further stirred for 24 hours and then partitioned between a NH$_4$OH aqueous solution and ethyl acetate. Upon decantation, the aqueous phase was further extracted with ethyl acetate. The organic phases were gathered, washed with a NaCl aqueous solution, dried over MgSO$_4$, filtered and concentrated under reduced pressure to afford 3-[1-(4-bromophenyl)-1H-[1,2,3]triazol-4-yl]propan-1-ol (10.36 g, 53%).

$^1$H NMR (300 MHz, DMSO-d6) δ 8.61 (s, 1H), 7.86 (d, J=8.9 Hz, 1H), 7.79 (d, J=8.9 Hz, 1H), 4.52 (t, J=5.2 Hz, 1H), 3.48 (q, J=5.2 Hz, 2H), 2.73 (t, J=7.5 Hz, 2H), 1.88-1.74 (quint, J=7.5 Hz, 2H).

According to route (A1), a reaction mixture of 3-[1-(4-bromophenyl)-1H-[1,2,3]triazol-4-yl]propan-1-ol (846 mg, 3.0 mmoles, 1 eq.), (E)-3-(2-pyridin-2-ylvinyl)phenylamine (816 mg, 4.2 mmoles, 1.4 eq.), Pd$_2$(dba)$_3$ (137 mg, 0.15 mmole, 5 mol %), XPhos (143 mg, 0.30 mmole, 10 mol %) and K$_2$CO$_3$ (1.66 g, 12.0 mmoles, 4 eq.) in t-BuOH (3.7 mL) was heated at 90° C. and stirred for 20 hours under an inert atmosphere of argon. The reaction mixture was then concentrated under reduced pressure and the resulting residue was partitioned between ethyl acetate and water. Upon decantation, the aqueous phase was further extracted with dichloromethane. The organic phases were gathered, dried over MgSO$_4$, filtered and concentrated under reduced pressure. The resulting residue was purified by column chromatography on silica gel to give 3-(1-{4-[3-(2-pyridin-2-ylvinyl)phenylamino]phenyl}-1H-[1,2,3]triazol-4-yl)propan-1-ol (26) (836 mg, 70%).

$^1$H NMR (300 MHz, CDCl$_3$) δ 8.51 (d, J=4.5, 1H), 7.61 (s, 1H), 7.56 (d, J=7.6, 1H), 7.48 (d, J=16.1, 1H), 7.41 (d, J=8.7, 2H), 7.30 (d, J=7.8, 1H), 7.21 (s, 1H), 7.17 (d, J=7.7, 1H), 7.12-7.01 (m, 5H), 6.97 (d, J=7.8, 1H), 6.87 (s, 1H), 4.19 (s, 1H), 3.70 (t, J=6.2, 2H), 2.84 (t, J=7.4, 2H), 2.00 (quint, J=6.7, 2H). 13C NMR (75 MHz, CDCl$_3$) δ 155.6, 149.8, 148.2, 144.0, 142.7, 138.1, 136.9, 132.7, 130.3, 130.0, 128.4, 122.4, 122.1, 121.0, 119.5, 118.9, 117.7, 117.3, 61.9, 32.2, 22.3.

[M+H]$^+$=398

Example 8: Compound (40) in Table I

According to route (B), 1-methoxy-4-vinylbenzene (2.9 mL, 22 mmoles, 1.1 eq.) was placed in dimethylformamide (20 mL) with 1-bromo-3-nitrobenzene (4 g, 20 mmoles, 1 eq.), NaOAc (3.3 g, 40 mmoles, 2 eq.), Pd(OAc)$_2$ (225 mg, 1 mmole, 5 mol %), PPh$_3$ (629 mg, 2.4 mmoles, 12 mol %). The reaction mixture was heated at 135° C. and stirred for 24 hours under an inert atmosphere of argon. Upon cooling to room temperature, the reaction mixture was concentrated under reduced pressure and the resulting residue was partitioned between ethyl acetate and water. Upon decantation, the aqueous phase was further extracted with dichloromethane. The organic phases were gathered, dried over MgSO$_4$, filtered and concentrated under reduced pressure. The resulting residue was purified by column chromatography on silica gel to afford (E)-1-nitro-3-(4-(methoxy)styryl)benzene (2.3 g, 45%).

$^1$H NMR (300 MHz, CDCl$_3$) δ 8.35 (s, 1H), 8.07 (d, J=8.8 Hz, 1H), 7.77 (d, J=7.7 Hz, 1H), 7.56-7.43 (m, 3H), 7.20 (d, J=16.4 Hz, 1H), 7.01 (d, J=16.4 Hz, 1H), 6.94 (d, J=7.9 Hz, 2H), 3.86 (s, 3H).

According to route (C), (E)-1-nitro-3-(4-(methoxy)styryl)benzene (1.5 g, 5.8 mmoles, 1 eq.) and tin (II) chloride dihydrate (6.6 g, 29.4 mmoles, 5 eq.) were placed in EtOH (58 mL). The reaction mixture was heated at 60° C. and stirred for 48 hours under an inert atmosphere of argon. The reaction mixture was then concentrated under reduced pressure and the resulting residue was diluted with ethyl acetate. The organic phase was washed with a 1N NaOH aqueous solution, dried over MgSO$_4$, filtered and concentrated under reduced pressure to afford (E)-1-nitro-3-(4-(methoxy)styryl)aniline (1.3 g, 99%).

$^1$H NMR (300 MHz, CDCl$_3$) δ 7.46 (d, J=8.7 Hz, 2H), 7.17 (t, J=7.8 Hz, 1H), 7.05 (d, J=16.3 Hz, 1H), 6.97-6.88 (m, 4H), 6.84 (s, 1H), 6.60 (dd, J=7.9, 2.1 Hz, 1H), 3.84 (s, 3H), 3.68 (br s, 2H).

N,N-diethylpropylenediamine (7 mL, 44 mmoles, 1.1 eq.) was placed in a 3N NaOH aqueous solution (56 mL) and dichloromethane (24 mL) was added to the solution. The reaction mixture was cooled down to 0° C. with an ice bath and a solution of 3-bromobenzoyl chloride (5.3 mL, 40 mmoles, 1 eq.) in dichloromethane (40 mL) was added dropwise. The reaction mixture was then stirred at room temperature for 18 hours under an inert atmosphere of argon. Upon decantation, the organic phase was washed with water, dried over MgSO$_4$, filtered and concentrated under reduced pressure to afford 3-bromo-N-(3-diethylamino-propyl)benzamide (12.5 g, 99%).

$^1$H NMR (300 MHz, CDCl$_3$) δ 9.11 (br s, 1H), 7.90 (t, J=1.9 Hz, 1H), 7.72 (dt, J=7.9, 1.2 Hz, 1H), 7.56 (ddd, J=7.9, 1.9, 1.0 Hz, 1H), 7.26 (t, J=7.9 Hz, 1H), 3.53 (dt, J=5.7, 4.6 Hz, 2H), 2.64-2.51 (m, 6H), 1.73 (quint, J=5.7 Hz, 2H), 1.02 (t, J=7.2 Hz, 6H).

According to route (A1), a reaction mixture of 3-bromo-N-(3-diethylamino-propyl)benzamide (1.2 g, 4 mmoles, 1 eq.), (E)-1-nitro-3-(4-(methoxy)styryl)aniline (1 g, 4.4 mmoles, 1.1 eq.), Pd$_2$(dba)$_3$ (183 mg, 0.2 mmole, 5 mol %), XPhos (190 mg, 0.4 mmole, 10 mol %) and K$_2$CO$_3$ (2.2 g, 16 mmoles, 4 eq.) in t-BuOH (5 mL) was heated at 90° C. and stirred for 20 hours under an inert atmosphere of argon. The reaction mixture was then concentrated under reduced pressure and the resulting residue was diluted with ethyl acetate. The organic phase was washed with water, dried over MgSO$_4$, filtered and concentrated under reduced pressure. The resulting residue was purified by column chromatography on silica gel to give (E)-N-(3-diethylamino-propyl)-3-((3-(4-(methoxy)styryl)phenylamino)benzamide (40) (1 g, 55%).

$^1$H NMR (300 MHz, CDCl$_3$) δ 8.59 (s, 1H), 7.52 (s, 1H), 7.43 (d, J=8.7 Hz, 2H), 7.27 (d, J=7.0 Hz, 2H), 7.23 (d, J=7.3 Hz, 2H), 7.18 (s, 1H), 7.13-6.92 (m, 4H), 6.89 (d, J=8.7 Hz, 2H), 3.82 (s, 3H), 3.59-3.47 (m, 2H), 2.62-2.46 (m, 6H), 1.72 (quint, J=5.7 Hz, 2H), 0.99 (t, J=7.2 Hz, 6H).

$^{13}$C NMR (75 MHz, CDCl$_3$) δ 167.2, 159.5, 144.0, 143.2, 139.1, 136.4, 130.2, 129.8, 129.4, 128.6, 127.9, 119.8, 118.9, 117.6, 116.6, 114.3, 55.5, 53.3, 46.9, 41.3, 25.1, 11.6.

[M+H]$^+$=458.3

Example 9: Compound (39) in Table I

According to route (D), methyl-triphenylphosphonium bromide (3.6 g, 10 mmoles, 2 eq.) was placed in dry toluene (17 mL) with potassium tert-butoxide (1.1 g, 10 mmoles, 2 eq.). The reaction mixture was heated at 70° C. and stirred for 30 minutes under an inert atmosphere of argon. 3-Nitrobenzaldehyde (756 mg, 5 mmoles, 1 eq.) was then added. The reaction mixture was heated at 110° C. and stirred for 2 hours under an inert atmosphere of argon. Upon cooling to room temperature, the reaction mixture was diluted with water and the resulting solution was extracted with ethyl acetate. The organic phase was dried over MgSO$_4$, filtered and concentrated under reduced pressure. The resulting residue was purified by column chromatography on silica gel to afford 1-nitro-3-vinylbenzene (661 mg, 88%).

$^1$H NMR (300 MHz, CDCl$_3$) δ 8.20 (s, 1H), 8.06 (s, 1H), 7.68 (s, 1H), 7.46 (s, 1H), 6.83-6.66 (m, 1H), 5.87 (d, J=17.5 Hz, 1H), 5.41 (d, J=10.7 Hz, 1H).

According to route (B), 1-nitro-3-vinylbenzene (661 mg, 4.4 mmoles, 1.1 eq.) was placed in dimethylformamide (4 mL) with 1-bromo-3 (trifluoromethoxy)benzene (600 µL, 4 mmoles, 1 eq.), NaOAc (661 mg, 8 mmoles, 2 eq.), Pd(OAc)$_2$ (45 mg, 0.2 mmole, 5 mol %), PPh$_3$ (105 mg, 0.4 mmole, 10 mol %). The reaction mixture was heated at 135° C. and stirred for 10 hours under an inert atmosphere of argon. Upon cooling to room temperature, the reaction mixture was concentrated under reduced pressure and the resulting residue was partitioned between ethyl acetate and water. Upon decantation, the aqueous phase was further extracted with dichloromethane. The organic phases were gathered, dried over MgSO$_4$, filtered and concentrated under reduced pressure. The resulting residue was purified by column chromatography on silica gel to afford (E)-1-nitro-3-(4-(methoxy)styryl)benzene (355 mg, 28%).

$^1$H NMR (300 MHz, CDCl$_3$) δ 8.37 (s, 1H), 8.13 (d, J=8.4 Hz, 1H), 7.81 (d, J=7.7 Hz, 1H), 7.54 (t, J=7.9 Hz, 1H), 7.49-7.34 (m, 3H), 7.20-7.00 (m, 3H).

According to route (C), (E)-1-nitro-3-(3-(trifluoromethoxy)styryl)benzene (355 mg, 1.15 mmole, 1 eq.) and tin (II) chloride dihydrate (1.3 g, 5.75 mmoles, 5 eq.) were placed in EtOH (11.5 mL). The reaction mixture was heated at 60° C. and stirred for 10 hours under an inert atmosphere of argon. The reaction mixture was then concentrated under reduced pressure and the resulting residue was diluted with ethyl acetate. The organic phase was washed with a 1N NaOH aqueous solution, dried over MgSO$_4$, filtered and concentrated under reduced pressure to afford (E)-3-(3-(trifluoromethoxy)styryl)aniline (304 mg, 95%).

$^1$H NMR (300 MHz, CDCl$_3$) δ 7.45-7.34 (m, 3H), 7.20 (t, J=7.8 Hz, 1H), 7.13 (d, J=8.5 Hz, 1H), 7.05 (s, 2H), 6.96 (d, J=7.6 Hz, 1H), 6.85 (s, 1H), 6.65 (d, J=7.5 Hz, 1H), 3.71 (br s, 2H).

3-(4-methylpiperazin-1-yl)propan-1-amine (1.9 mL, 11 mmoles, 1.1 eq.) was placed in a 3N NaOH aqueous solution (14 mL) and dichloromethane (6 mL) was added to the solution. The reaction mixture was cooled down to 0° C. with an ice bath and a solution of 3-bromobenzoyl chloride (1.3 mL, 10 mmoles, 1 eq.) in dichloromethane (10 mL) was added dropwise. The reaction mixture was then stirred at room temperature for 10 hours under an inert atmosphere of argon. Upon decantation, the organic phase was washed with water, dried over MgSO$_4$, filtered and concentrated under reduced pressure to afford 3-bromo-N-(3-(4-methylpiperazin-1-yl)propyl)benzamide (2.8 g, 85%).

$^1$H NMR (300 MHz, CDCl$_3$) δ 8.59 (s, 1H), 7.90 (s, 1H), 7.79 (d, J=7.7 Hz, 1H), 7.59 (d, J=7.9 Hz, 1H), 7.34-7.24 (m, 1H), 3.60-3.45 (m, 2H), 2.60-2.63 (m, 8H), 2.30 (s, 3H), 1.80-1.65 (m, 2H).

According to route (A1), a reaction mixture of 3-bromo-N-(3-(4-methylpiperazin-1-yl)propyl)benzamide (169 mg, 0.50 mmoles, 1 eq.), (E)-3-(3-(trifluoromethoxy)styryl)aniline (153 mg, 0.55 mmoles, 1.1 eq.), Pd$_2$(dba)$_3$ (23 mg, 0.025 mmole, 5 mol %), XPhos (24 mg, 0.05 mmole, 10 mol %) and K$_2$CO$_3$ (276 mg, 2 mmoles, 4 eq.) in t-BuOH (2 mL) was heated at 90° C. and stirred for 10 hours under an inert atmosphere of argon. The reaction mixture was then concentrated under reduced pressure and the resulting residue was diluted with ethyl acetate. The organic phase was washed with water, dried over MgSO$_4$, filtered and concentrated under reduced pressure. The resulting residue was purified by column chromatography on silica gel to give (E)-N-(3-(diethylamino)propyl)-3-((3-(3-(trifluoromethoxy)styryl)phenyl)amino)benzamide (39) (160 mg, 59%).

$^1$H NMR (300 MHz, CDCl$_3$) δ 8.19 (s, 1H), 7.57 (s, 1H), 7.42-7.36 (m, 2H), 7.33-7.21 (m, 5H), 7.16-7.08 (m, 3H), 7.05-7.01 (m, 3H), 5.89 (s, 1H), 3.57 (t, J=5.5 Hz, 2H), 2.66-2.35 (m, 10H), 2.27 (s, 3H), 1.80 (t, J=5.5 Hz, 2H).

$^{13}$C NMR (75 MHz, CDCl$_3$) δ 167.5, 149.9, 143.7, 143.2, 139.6, 138.2, 136.5, 130.4, 130.2, 130.0, 129.5, 127.6, 125.1, 120.1, 119.3, 118.9, 118.2, 117.1, 116.6, 58.4, 55.1, 53.4, 46.1, 41.0, 24.4.

[M+H]$^+$=539

Example 10: Compound (45) in Table I 2-iodobenzoic acid (9.92 g, 40 mmoles, 1 eq.) was placed in toluene (40 mL) under an inert atmosphere of argon. Thionyl chloride (6 mL, 80 mmoles, 2 eq.) was slowly added. The reaction mixture was heated at 80° C. and stirred for 4 hours. Upon cooling to room temperature, the reaction mixture was concentrated under reduced pressure. N,N-Diethylethylenediamine (3.12 mL, 22 mmoles, 1.1 eq.) was placed in a 3N NaOH aqueous solution (15 mL) and dichloromethane (10.7 mL) was added to the solution. The reaction mixture was cooled down to 0° C. with an ice bath and a solution of the 2-iodobenzoyl chloride residue (20 mmoles, 4 eq.) in dichloromethane (21.4 mL) was added dropwise. The reaction mixture was then stirred at room temperature for 18 hours under an inert atmosphere of argon. Upon decantation, the organic phase was washed with water, dried over MgSO$_4$, filtered and concentrated under reduced pressure. The resulting residue was purified by column chromatography on silica gel to afford 2-iodo-N-(2-diethylamino-ethyl)benzamide (3.73 g, 51%).

$^1$H NMR (300 MHz, CDCl$_3$) δ 7.87 (d, J=7.9 Hz, 1H), 7.42-7.34 (m, 2H), 7.13-7.06 (m, 1H), 6.48 (s, 1H), 3.51 (q, J=5.7 Hz, 2H), 2.67 (t, J=5.7 Hz, 2H), 2.57 (q, J=7.2 Hz, 4H), 1.02 (t, J=7.2 Hz, 6H).

According to route (A2), a reaction mixture of 2-iodo-N-(2-diethylamino-ethyl)benzamide (3.3 g, 9.6 mmoles, 1 eq.), 4-(trifluoromethoxy)aniline (1.9 mL, 14.5 mmoles, 1.5 eq.), CuI (183 mg, 0.96 mmol, 10 mol %), L-Proline (221 mg, 1.92 mmol, 20 mol %) and K$_2$CO$_3$ (2.6 g, 19.2 mmoles, 2.0 eq.) in DMSO (10 mL) was heated at 80° C. and stirred for 48 hours under an inert atmosphere of argon. The reaction mixture was then partitioned between ethyl acetate and water. Upon decantation, the aqueous phase was further extracted with dichloromethane. The organic phases were gathered, dried over MgSO$_4$, filtered and concentrated under reduced pressure. The resulting residue was purified by column chromatography on silica gel to give N-(2-diethyl-amino-ethyl)-2-(4-trifluoromethoxy-phenylamino)-benzamide (45) (1.4 g, 37%).

$^1$H NMR (300 MHz, CDCl$_3$) δ 9.55 (s, 1H), 7.48 (d, J=7.7 Hz, 1H), 7.30-7.21 (m, 3H), 7.15 (d, J=9.1 Hz, 2H), 7.10 (d, J=9.1 Hz, 2H), 6.78 (t, J=7.3 Hz, 1H), 3.44 (t, J=5.9 Hz, 2H), 2.62 (t, J=5.9 Hz, 2H), 2.54 (q, J=7.1 Hz, 4H), 1.02 (t, J=7.1 Hz, 6H).

$^{13}$C NMR (75 MHz, CDCl$_3$) δ 169.5, 145.2, 143.9, 140.8, 132.2, 127.8, 122.3, 121.4, 119.1, 118.7, 115.6, 51.3, 46.9, 37.2, 12.1.

[M+H]$^+$=396

In a similar manner, compounds (48), (49), (50) and (52) can be prepared.

Example 11: Compound (65) in Table I 4-bromo-3-methylbenzoic acid (9.92 g, 40 mmoles, 1 eq.) was placed in toluene (40 mL) under an inert atmosphere of argon. Thionyl chloride (6 mL, 80 mmoles, 2 eq.) was slowly added. The reaction mixture was heated at 80° C. and stirred for 4 hours. Upon cooling to room temperature, the reaction mixture was concentrated under reduced pressure. 3-Methyl-1-butanamine (1.393 mL, 12 mmoles, 2 eq.) was placed in a 3N NaOH aqueous solution (8 mL) and dichloromethane (4 mL) was added to the solution. The reaction mixture was cooled down to 0° C. with an ice bath and a solution of the 4-bromo-3-methyl benzoyl chloride residue (6 mmoles, 1 eq.) in dichloromethane (26 mL) was added dropwise. The reaction mixture was then stirred at room temperature for 18 hours under an inert atmosphere of argon. Upon decantation, the organic phase was washed with water, dried over $MgSO_4$, filtered and concentrated under reduced pressure to afford 4-bromo-3-methyl-N-(3-methylbutyl)benzamide (1.44 g, 84%).

$^1$H NMR (300 MHz, $CDCl_3$) δ 7.64 (s, 1H), 7.58 (d, J=8.2 Hz, 1H), 7.40 (d, J=8.2 Hz, 1H), 6.02 (s, 1H), 3.47 (q, J=7.0 Hz, 2H), 2.45 (s, 3H), 1.69 (heptuplet, J=6.6 Hz, 1H), 1.51 (q, J=7.0 Hz, 2H), 0.96 (d, J=6.6 Hz, 6H).

According to route (A1), a reaction mixture of 4-bromo-3-methyl-N-(3-methylbutyl)benzamide (284 mg, 1 mmole, 1 eq.), 3-methoxyaniline (185 mg, 1.5 mmole, 1.5 eq.), $Pd_2(dba)_3$ (46 mg, 0.05 mmole, 5 mol %), XPhos (48 mg, 0.10 mmole, 10 mol %) and $K_2CO_3$ (276 mg, 2 mmoles, 2 eq.) in t-BuOH (1 mL) was heated at 100° C. and stirred for 22 hours under an inert atmosphere of argon. The reaction mixture was then concentrated under reduced pressure and the resulting residue was diluted with ethyl acetate. The organic phase was washed with water, dried over $MgSO_4$, filtered and concentrated under reduced pressure. The resulting residue was purified by column chromatography on silica gel to give 4-(3-methoxyphenylamino)-3-methyl-N-(3-methylbutyl)benzamide (65) (259 mg, 79%).

$^1$H NMR (300 MHz, $CDCl_3$) δ 7.62 (s, 1H), 7.50 (dd, J=1.9, 8.5 Hz, 1H), 7.23-7.14 (m, 2H), 6.69-6.59 (m, 2H), 6.54 (dd, J=2.2, 8.1 Hz, 1H), 6.30 (d, J=5.4 Hz, 1H), 5.73 (s, 1H), 3.75 (s, 3H), 3.40 (q, J=7.0 Hz, 2H), 2.23 (s, 3H), 1.69 (heptuplet, J=6.6 Hz, 1H), 1.50 (q, J=7.0 Hz, 2H), 0.93 (d, J=6.6 Hz, 6H).

$^{13}$C NMR (75 MHz, $CDCl_3$) 167.4, 160.9, 144.7, 143.6, 130.4, 130.1, 126.7, 125.8, 125.7, 115.5, 112.2, 107.7, 105.4, 55.4, 38.8, 38.5, 26.2, 22.7, 18.0.

$[M+H]^+=327$

Example 12: Compound (116) in Table I

N,N-diethyl-N-(2-propynyl)amine (5 g, 45 mmoles, 1.0 eq.) was placed in a dimethylsulfoxide (40.5 mL) and water (4.5 mL) solution, together with 1-bromo-3-iodobenzene (12.73 g, 45 mmoles, 1 eq.), $NaN_3$ (3.51 g, 54 mmoles, 1.2 eq.), L-Proline (1.16 g, 9 mmoles, 0.2 eq.), $Na_2CO_3$ (0.95 g, 9 mmoles, 0.2 eq.), sodium ascorbate (3.57 g, 18 mmoles, 0.4 eq.). $CuSO_4.5H_2O$ (2.25 g, 9 mmoles, 0.2 eq.) was added and the reaction mixture was heated at 65° C. and stirred for 16 hours under an inert atmosphere of argon. Upon cooling to room temperature, the reaction mixture was further stirred for 24 hours and then partitioned between a $NH_4OH$ aqueous solution and ethyl acetate. Upon decantation, the aqueous phase was further extracted with ethyl acetate. The organic phases were gathered, washed with a NaCl aqueous solution, dried over $MgSO_4$, filtered and concentrated under reduced pressure. The resulting residue was purified by column chromatography on silica gel to afford [1-(3-bromophenyl)-1H-[1,2,3]triazol-4-ylmethyl]diethylamine (9.79 g, 70%).

$^1$H NMR (300 MHz, $CDCl_3$) δ 7.99-7.90 (m, 1H), 7.71 (d, J=8.1 Hz, 1H), 7.56 (d, J=8.1 Hz, 1H), 7.39 (t, J=8.1 Hz, 1H), 3.88 (s, 1H), 2.62 (q, J=7.1 Hz, 1H), 1.13 (t, J=7.1 Hz, 1H).

According to route (E), 4-methoxybenzamide (4.53 g, 30 mmoles, 1 eq.), 1-bromo-4-nitrobenzene (6.67 g, 33 mmoles, 1.1 eq.), $Pd(OAc)_2$ (67.3 mg, 0.3 mmoles, 1 mol %), XantPhos (260.4 mg, 0.45 mmoles, 1.5 mol %) and $Cs_2CO_3$ (15.9 g, 45 mmoles, 1.5 eq.) were placed in dioxane (30 mL). The reaction mixture was heated at 90° C. and stirred for 18 hours under an inert atmosphere of argon. The reaction mixture was then filtered on Celite, washed with $CH_2Cl_2$ and acetone and the filtrate was concentrated under reduced pressure. The resulting solid was recristallized from ethanol and filtered to afford 4-methoxy-N-(4-nitrophenyl)benzamide (4.82 g, 60%).

$^1$H NMR (300 MHz, $CDCl_3$) δ 8.27 (d, J=9.3 Hz, 2H), 8.01 (s, 1H), 7.85 (t, J=9.3 Hz, 4H), 7.02 (d, J=9.3 Hz, 2H), 3.90 (s, 3H).

According to route (F), 4-methoxy-N-(4-nitrophenyl)benzamide (4.08 g, 15 mmoles, 1 eq.) and 10% Pd/C (750 mg) were placed in EtOH (75 mL). The reaction mixture was stirred for 6 hours under an atmosphere of $H_2$. The reaction mixture was then filtered and the filtrate was concentrated under reduced pressure to afford N-(4-aminophenyl)-4-methoxybenzamide (2.99 g, 82%).

$^1$H NMR (300 MHz, $CDCl_3$) δ 7.87 (d, J=7.9 Hz, 1H), 7.42-7.34 (m, 2H), 7.13-7.06 (m, 1H), 6.48 (s, 1H), 3.51 (q, J=5.7 Hz, 2H), 2.67 (t, J=5.7 Hz, 2H), 2.57 (q, J=7.2 Hz, 4H), 1.02 (t, J=7.2 Hz, 6H).

According to route (A1), a reaction mixture of [1-(3-bromophenyl)-1H-[1,2,3]triazol-4-ylmethyl]diethylamine (247 mg, 0.8 mmole, 1 eq.), N-(4-aminophenyl)-4-methoxybenzamide (213 mg, 0.88 mmole, 1.1 eq.), $Pd_2(dba)_3$ (37 mg, 0.04 mmole, 5 mol %), XPhos (38 mg, 0.08 mmole, 10 mol %) and $K_2CO_3$ (442 mg, 3.2 mmoles, 4 eq.) in t-BuOH (1 mL) was heated at 100° C. and stirred for 22 hours under an inert atmosphere of argon. The reaction mixture was then concentrated under reduced pressure and the resulting residue was diluted with ethyl acetate. The organic phase was washed with water, dried over $MgSO_4$, filtered and concentrated under reduced pressure. The resulting residue was purified by column chromatography on silica gel to give N-{4-[3-(4-diethylaminomethyl)-[1,2,3]triazol-1-yl)phenylamino]phenyl}-4-methoxybenzamide (116) (196 mg, 52%).

$^1$H NMR (300 MHz, DMSO-d6) δ 10.03 (s, 1H), 8.60 (s, 1H), 8.45 (s, 1H), 7.96 (d, J=8.8 Hz, 2H), 7.70 (d, J=8.8 Hz, 2H), 7.52 (s, 1H), 7.38 (t, J=7.9 Hz, 1H), 7.22 (d, J=7.9 Hz, 1H), 7.16 (d, J=8.8 Hz, 2H), 7.06 (d, J=8.8 Hz, 3H), 3.84 (s, 3H), 3.76 (s, 2H), 2.50-2.41 (m, 4H), 1.03 (t, J=7.1 Hz, 6H).

$^{13}$C NMR (75 MHz, DMSO-d6) δ 164.5, 161.8, 145.8, 137.8, 137.7, 133.3, 130.5, 129.5, 127.1, 121.7, 119.1, 114.9, 113.6, 109.8, 106.0, 99.5, 55.4, 46.5, 46.1, 11.9.

$[M+H]^+=471$

Example 13: Pharmacological Data 13.1. Effects of Compounds on p53 Expression and its Transcriptional Activity The compounds of the invention have been tested according to the following pharmacological test and the three compounds have been more particularly tested: (40), (1) and (45), all diluted in DMSO. Their effects were thus compared to cells treated with DMSO. A positive control was used, TG003, a benzothiazole compound known to alter splicing through the inhibition of Clk/Sty family activity (Sigma, ref: T5575).

Two breast cancer cell lines have been treated with 5 M of drugs for 48 hours: wild-type p53 MCF7 cells and mutant p53 (R280K) MDA-MB-231-Luc-D3H2N provided by Caliper Life Science (parental Line source: American Type Culture collection). The MDA-MB-231-Luc-D3H2N cells were maintained in two different media during treatment: a DMEM supplemented with 10% foetal calf serum (FCS) and a FCS-free medium for 24 hours followed by 24 hours in a complete medium. The MC7 cells were maintained in a DMEM/FCS 10% medium.

Cells were harvested after 48 hours of treatment. Total RNAs (RNeasy Mini-Kit, Qiagen) and proteins (NuPage LDS 1×, Invitrogen) were extracted to analyse mRNA expression by nested RT-PCR or RT-qPCR and protein expression by Western Blot.

1. Protocols:

Analysis of p53 expression was assessed both at mRNA (full-length and truncated, Δ133p53 isoforms) and protein (full-length) levels by RT-qPCR and Western Blot, respectively.

The p53 isoform cDNA being too long to be specifically quantified by RT-qPCR, a semi-quantitative RT-PCR method was therefore used, requiring high quality total RNA 28S/18S ratio (>1.5). After reverse-transcription of 500 ng of total RNA using random primers, actin cDNA was amplified by PCR to confirm reverse-transcription efficiency. 0.5 g of total RNA from each tumour sample was reverse-transcribed (AMV RT, 45C, random primer) and cDNA quality confirmed by amplification of actin by PCR in 30 cycles. p53 isoform cDNA was amplified by 2 nested PCR of 30 cycles using primers specific of each isoforms as described in Bourdon et al. (Genes Dev., 2005, 19: 2122). Tumours were considered to express each p53 isoform after sequencing of the corresponding PCR fragment.

p53 protein expression was determined using a panel of 4 different antibodies, namely DO1, SAPLI, CMI and DO12 as described in Bourdon et al. (Genes Dev., 2005, 19: 2122), to avoid problem of detection due to post-translational modification.

The rabbit anti-p53 antibodies were diluted at 1/1000, and revealed with Horse-Radish Peroxydase (HRP)-conjugated anti-IgG antibodies purchased from GE-Healthcare and diluted at 1/5000 (Ref.: NA9340).

The Western Lightning Chemiluminescence (ECL) reagents were purchased from PerkinElmer (Ref.: NEL103C001EA).

The amount of total proteins in each extract was quantified using BCA kit (promega). 8% SDS-PAGE gels were used. Equal amount (30 μg) of proteins was loaded on each lane. Proteins were then transfered electrophoretically on nitrocellulose membrane. Membranes were blocked in TBS/0.1% Tween 20 containing 3% milk for one hour and then incubated overnight with the primary antibodies diluted in TBS/0.1% Tween 20 containing 3% milk. After several washes in TBS/Tween, membranes were incubated with anti-rabbit Ig antibodies linked to HRP. Membranes were developed with ECL according to the manufacturer's instructions.

Scanned autoradiographs were quantified using AIDA/2D densitometry software.

Analysis of p53 transcriptional activity was assessed through analysis of p53-target gene expression by Western-blot. Four p53-target genes were studied: Hdm2, Bcl-2, p21 and Bax. Hdm2 is known to bind p53 and to negatively regulate p53 activity and stability. p21 is known to mediate p53 dependent cycle arrest. Bcl 2 is known to have an anti-proliferative effect and an apoptotic protective effect, while Bax is known to have a pro-apoptic effect. Bax was not detected in both MCF7 and MDA-MB-231-Luc-D3H2N cells, while p21 was not detected in MDA-MB-231-Luc-D3H2N cells maintained in FCS-free medium. The Western-blot was performed as above described using the antibodies described in Bourdon et al., Genes Dev., 2005, 19: 2122.

2. Results

In the wild-type p53 MCF7 cells, the three compounds (40), (1) and (45) did not change total p53 expression (total isoforms, TA) at mRNA levels (FIG. 1A), while compounds (40) and (45) decreased p53 protein levels (full-length) (FIG. 1B, C). This decrease was associated with a decreased expression of Bcl-2 and Hdm2 but not of p21 (FIG. 1D, E). The same pattern of p53-target gene expression was observed with compound (1). Compounds (40) and (1) increased Δ133p53 mRNA level (FIG. 1A).

In mutant p53 MDA-MB-231-Luc-D3H2N cells maintained in normal medium, the three compounds (40), (1) and (45) decreased p53 expression at mRNA levels (total isoforms, TA) (significant decrease for drug (1), p-value<0.01) (FIG. 2A), while compounds did not change p53 protein levels (full-length) (FIG. 2B, C). Compounds (40) and (1) did not affect p53-target genes expression, while a slight decrease of p53-target gene expression was observed with compound (45) (FIG. 2D, E).

In the mutant p53 MDA-MB-231-Luc-D3H2N cells maintained in FCS-free medium, compounds (1) and (45), but not compound (40), decreased p53 expression at mRNA levels (total isoforms, TA) (FIG. 3A, blue panel), while compounds did not change p53 protein levels (full-length) (FIG. 3B, C). Compound (40) did not affect p53-target genes expression, while a slight decrease of Hdm2 and of Bcl-2 was observed with compound (1) and (45), respectively (FIG. 3D, E).

3. Conclusion:

Compounds (40) and (45) decreased the expression of both p53 protein (full-length) and its target gene in wild-type p53 MCF7 cells.

Compounds (1) and (45) decreased the p53 mRNA level (total isoforms) in mutant p53 MDA-MB-231-Luc-D3H2N cells maintained in normal medium and in FCS-free medium.

These compounds affect expression of both p53 and its target genes, in a p53 mutation dependent manner.

13.2. Effect of Compounds on p53 Isoforms Expression

1. Protocol:

Expression of p53 isoforms produced by alternative splicing (α, β and γ) was analysed at mRNA levels by RT-qPCR using primers/probe specific of each C-terminal variants. The α-forms are the most abundant forms. In the low abundant forms, β-forms are more expressed than γ-forms.

A semi-quantitative RT-PCR method requiring high quality total RNA 28S/18S ratio (>1.5). After reverse-transcription of 500 ng of total RNA using random primers, actin cDNA was amplified by PCR to confirm reverse-transcription efficiency. 0.5 μg of total RNA from each tumour sample was reverse-transcribed (AMV RT, 45C, random primer) and cDNA quality confirmed by amplification of actin by PCR in 30 cycles. p53 isoform cDNA was amplified by 2 nested PCR of 30 cycles using primers specific of each isoforms as described by Bourdon et al. (Genes Dev., 2005, 19: 2122). Tumours were considered to express each p53 isoform after sequencing of the corresponding PCR fragment.

2. Results:

In the wild-type p53 MCF7 cells, the three compounds (40), (1) and (45) did not change α-form expression at mRNA levels (FIG. 4A), while they tend to increase the expression of β- and γ-forms (FIG. 4A).

In the mutant p53 MDA-MB-231-Luc-D3H2N cells maintained in normal medium, the three compounds (40), (1) and (45) did not change α-form expression at mRNA levels (FIG. 4B), while they tend to increase the expression of β- and γ-forms (FIG. 4B). Significant increased of β-forms (by 3-fold) and of γ-forms (by 2-fold) was observed for compound (45). The restoration of γ-forms by compound (1) was confirmed by nested RT-PCR (FIG. 4B, right panel).

In the mutant p53 MDA-MB-231-Luc-D3H2N cells maintained in FCS-free medium, the three compounds (40), (1) and (45) did not change α-form expression at mRNA levels (FIG. 4C), while compound (45) tend to increase the expression of β- and γ-forms (FIG. 4C). While no significant increase of γ-forms was observed by RT-qPCR, restoration of γ-forms by compound (1) was shown by nested RT-PCR (FIG. 4C, right panel).

3. Conclusion:

The tested compounds affect p53 splicing independently of p53 mutation status (i.e. increase expression of β- and γ-forms).

13.3. General Conclusion

The compounds of the invention present an effect on p53 isoforms expression and activity.

As an illustration of said effect, the three here above identified tested compounds have different effect on p53 isoforms expression and activity. They increase the expression of p53β/γ-forms at mRNA levels. A decrease in p53 protein and its target gene was observed for the compound (45) (independently of p53 mutation status), for compound (40) (in wild-type p53 cells) and for compound (1) (in mutant p53 cells).

The tested compounds affect p53 family isoforms expression and activity, and consequently the p53 pathway. Surprisingly, the main effect of drugs (40), (1) and (45) is a reduction of p53 expression and its pathway, while, to the knowledge of the inventors, all existing drugs activate p53 pathway. Up to now, to the knowledge of the inventors no drug, which can repress p53 expression, has been described.

It follows that the compounds according to the present invention demonstrate an effect over the p53 gene isoforms family expression and activity.

The table below summarizes the effect of the compounds of the invention on p53 and the therapeutic indications for which they may be proposed.

| Effects | p53 status | (40) | (1) | (45) | Therapeutic indication |
|---|---|---|---|---|---|
| Decrease of p53 protein and target genes | Wild-type p53 | X | | X | cancer |
| | Mutant p53 | | X | X | Others than cancer |
| Modification of p53 isoforms ratio | Wild-type p53 | X | X | X | cancer |
| | Mutant p53 | X | X | X | Others than cancer |

13.4 Effect of Drug Compounds on Invasion of MDA-MB231-D3H2LN Cells into Collagen Further, some compounds of formula (I) have been tested on invasion in order to study their activity against cancer as shown below.

Standard Operating Procedure:

Background

A key step in the generation of tumor metastasis is the invasion of tumor cells into the extracellular matrix, a major component of which is collagen. Therefore, the invasion of tumor cells into collagen in vitro may be indicative of the generation of metastasis in vivo. E. g., MDA-MB231-luc-D3H2LN mouse breast cancer cells display indeed both higher invasion into collagen in vitro and a higher metastatic potential in vivo as compared to MDA-MB231 cells (from which they were derived). Using these MDA-MB231-luc-D3H2LN cells as a model, the aim of the experiment described here is to identify drug compounds that inhibit the invasion of tumor cells into collagen in vitro, therefore potentially inhibiting also the generation of tumor metastasis in vivo.

Assay Principle:

Step 1:

Preparation of cells at the bottom of a collagen gel: Cells are suspended in a liquid collagen solution (4° C.), distributed into BSA-coated wells, and then collected at the bottom of the wells by centrifugation. The collagen is then solidified by incubation at 37° C. The BSA coating improves the adhesion of the collagen gel.

Step 2:

Pre-treatment with the compounds to be tested: Concentrated drug solutions are then added on top of the collagen, and cells are pre-incubated for 24 h with the drugs at low serum conditions (0.025% FBS).

Step 3:

Stimulation of invasion: Medium with 5% FBS is then added in order to stimulate invasion of the cells into the collagen gel.

Step 4:

Fixation and staining: Following another 24 h incubation, cells are fixed and nuclei are stained.

Step 5:

Analysis: Finally, plates are analyzed using an automated microscope.

Fluorescent beads that have been included into the BSA coating serve to detect the bottom of the wells. Pictures of the stained nuclei are taken at the same level (0 m) as well as 25 μm and 50 μm above.

Note:

In order to detect possible toxic effects, all compounds are tested in parallel in a viability assay. The viability assay is performed in parallel on serum-starved cells (as in the invasion assay) vs. cells under normal culture conditions (10% FBS).

Materials:

General Equipment:

Freezer (−20° C.), refrigerator (4° C.), ice machine, water bath (37° C.), incubator (37° C./5% $CO_2$), cell culture hood, vortex, vacuum pump, microscope, Malassez cell, Pipet aid, micropipettes (for pipetting 1-1000 μl), multichannel pipettes (for pipetting 20-200 μl), standard cell culture centrifuge, refrigerated centrifuge for 96 well plates General Consumables:

Sterile 96 well cell culture plates (for the viability assay), sterile tubes (1.5/15/50 ml), sterile pipettes (5/10/25 ml), sterile micropipette tips (for pipetting 1-1000 μl), sterile Pasteur pipettes, sterile reagent reservoirs General Products:

Sterile PBS, sterile Milli-Q water, DMSO, decomplemented FBS (frozen aliquots), 0.1 N NaOH, 1 M Hepes, MEM without serum (not older than 1 month), 2.5×MEM without serum (not older than 1 month), MEM with 10% FBS (not older than one month), 0.25% trypsin/1 mM EDTA solution, 37% formaldehyde solution Specific Equipment:
plate reader: Tecan Infinite F200
automated microscope: Cellomics ArrayScan VTI HCS Reader Specific Consumables:
sterile black 96 well plates (for the invasion assay): Perkin Elmer ViewPlate-96 F TC, ref. 6005225
sterile 96 deep well polypropylene plates (for drug preparation): Starlab, ref. S1896-5110

Specific Products:
rat tail collagen, type 1: BD Biosciences, ref. 354236 (note: each new lot has to be validated)
red fluorescent beads (1 µm diameter): Invitrogen, ref. F13083
Y-27632 (5 mM aqueous solution): Calbiochem, ref. 688001 (in solution) or 688000 (dry powder)
BSA without fatty acids (sterile-filtered 4% aqueous solution): Sigma, ref. A8806 (dry powder)
Hoechst 33342 nuclear stain (10 mg/ml): Invitrogen, ref. H3570
MTS reagent: Promega CellTiter CellTiter 96® AQueous One Solution Reagent, ref. G3581
drug compounds to be tested: generally 25 or 50 mM in 100% DMSO (aliquots stored at −20° C., then at 4° C. for max. 3 months)

MDA-MB231-luc-D3H2LN Cells:
Limits for the cell cultures to be used in the assays:
total passage number: max. 30
last passage: between 2 and 4 days before, between 1:3 and 1:20
cell density: between 50 and 90% (optimally 70%) (between 1 and 2×106 cells per 100 mm dish)

Experimental Procedures:
General Considerations:
Controls and Plate Maps:
Invasion assay: Negative control: No drug (just DMSO at equivalent concentration). Positive control: 10 µM Y-27632. To avoid edge effects, only the 60 central wells B2-G11 are used; lines A and H as well as columns 1 and 12 remain free. Each drug is tested at least in triplicate. The positive and negative controls should be tested in double triplicates at different positions on each plate. Typical plate map (−=negative control, +=positive control, 1-16=16 different drug compounds):

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B |   | − | 1 | 2 | 3 | 4 | 5 | 6 | 7 | 8  | +  |    |
| C |   | − | 1 | 2 | 3 | 4 | 5 | 6 | 7 | 8  | +  |    |
| D |   | − | 1 | 2 | 3 | 4 | 5 | 6 | 7 | 8  | +  |    |
| E |   | + | 9 | 10| 11| 12| 13| 14| 15| 16 | −  |    |
| F |   | + | 9 | 10| 11| 12| 13| 14| 15| 16 | −  |    |
| G |   | + | 9 | 10| 11| 12| 13| 14| 15| 16 | −  |    |
| H |   |   |   |   |   |   |   |   |   |    |    |    |

Viability Assays:
No additional controls. The MTS viability assay is based on colorimetric detection of a product generated by the mitochondrial activity of the cells. Each drug is tested at least in duplicate. To detect potential direct interactions with the assay substrate, each drug is also tested in absence of cells (background signals). Typical plate map (controls and drug compounds as in the invasion assay, lines A-B and E-F: with cells, lines C-D and G-H: without cells; each 1 plate with 10% vs. 0.025% FBS):

|   | 1 | 2 | 3 | 4 | 5 | 6 | 7 | 8 | 9 | 10 | 11 | 12 |
|---|---|---|---|---|---|---|---|---|---|----|----|----|
| A | − | 1 | 2 | 3 | 4 | 5 | 6 | 7 | 8 | +  |    |    |
| B | − | 1 | 2 | 3 | 4 | 5 | 6 | 7 | 8 | +  |    |    |
| C | − | 1 | 2 | 3 | 4 | 5 | 6 | 7 | 8 | +  |    |    |
| D | − | 1 | 2 | 3 | 4 | 5 | 6 | 7 | 8 | +  |    |    |
| E | + | 9 | 10| 11| 12| 13| 14| 15| 16| −  |    |    |
| F | + | 9 | 10| 11| 12| 13| 14| 15| 16| −  |    |    |
| G | + | 9 | 10| 11| 12| 13| 14| 15| 16| −  |    |    |
| H | + | 9 | 10| 11| 12| 13| 14| 15| 16| −  |    |    |

The volumes or other quantities indicated in the following are required for testing 16 drug compounds per 96 wells-plate at 5 M each (+controls) in an invasion assay and each one viability assay on serum-starved cells vs. cells under normal culture conditions according to the plate maps above. According to the number of tested compounds, the volumes and other quantities should be adapted for testing more or less compounds or different concentrations.

Day 1: Preparation and Treatment of the Cells (all Steps are Performed Under a Cell Culture Hood):
Preparation of 100× concentrated drug solutions in 10% DMSO:
prepare 10% DMSO in sterile PBS: 1.8 ml sterile PBS+0.2 ml DMSO
prepare 100 µl/well 10% DMSO in PBS in 16 wells of a sterile 96 well polypropylene plate
add each 1 or 2 µl of the 50 or 25 mM compound stock solutions, respectively mix by pipetting up and down
Preparation of 4× concentrated drug and control solutions in 0.4% DMSO in MEM+0.1% FBS:
prepare MEM+0.1% FBS: 12 ml MEM without serum+12 µl FBS (freshly thawed aliquot)
prepare 480 µl/well MEM+0.1% FBS in 20 wells of a sterile 96 deep well polypropylene plate
negative controls (no drug): add each 20 µl 10% DMSO in sterile PBS
positive controls (Y-27632): add each 14 µl sterile PBS+2 µl DMSO+4 µl 5 mM Y-27632 (freshly thawed aliquot)
drug compounds: add each 20 µl of the 100× concentrated drug solutions in 10% DMSO
mix by pipetting up and down
store at RT until use Coating of the Plates for the Invasion Assay:
mix 9.5 ml MEM without serum+0.5 ml 4% BSA without fatty acids+1 µl vortexed fluorescent beads (i. e. dilute 1:10000), vortex, distribute 100 µl/well into the plate for the invasion assay
centrifuge 30' with 1800×g at 4° C. (e. g. 3000 rpm in a Jouan GR412 centrifuge)
remove supernatants by aspiration Preparation of a 10×106 Cells/Ml Cell Suspension (During the Centrifugation of the Plates):
remove medium, wash cells with ~10 ml/dish PBS, add 1 ml/dish 0.25% trypsin/1 mM EDTA
incubate 30-60 s at 37° C.
add 5-10 ml/dish pre-warmed MEM+10% FBS
homogenize by pipetting up and down using a 10 ml pipette, pool all
count cells using a Malassez cell
centrifuge 2×106 (or more) cells for 5' with 150×g at RT (850 rpm in a std. cell culture centrifuge)
remove supernatant, resuspend cell pellet in 0.2 ml (or more, respectively) MEM without serum, yielding 10×106 cells/ml Preparation of the Invasion Assay (on Ice; Start During the Centrifugation of the Cells):

mix on ice in a pre-chilled tube: example for a 3.4 mg/ml collagen stock solution; volumes of collagen and water to be adapted according to the stock concentration of each collagen lot:

2.8 ml 2.5×MEM
441 µl water
140 µl 1 M Hepes
49 µl 1 N NaOH
3.5 ml 3.4 mg/ml collagen stock solution (yielding 1.7 mg/ml collagen in 7 ml)

homogenize by pipetting gently up and down (keep on ice)

add 70 µl of the 10×106 cells/ml cell suspension, homogenize by pipetting gently up and down (yields 0.1×106 cells/ml in 1.7 mg/ml collagen in 7 ml 1×MEM+20 µM Hepes) (keep on ice)

distribute 100 µl/well (i. e. 10000 cells/well) into the coated wells of the plate for the invasion assay (all on ice)

centrifuge 5' with 200×g at 4° C. (e. g. 1000 rpm in a Jouan GR412 centrifuge)

add 200 µl/well PBS to all free wells incubate 30' at 37° C./5% $CO_2$ (solidification of the collagen)

Preparation of the Viability Assay on Serum-Starved Cells:

add 50 µl of the 10×106 cells/ml cell suspension to 5 ml MEM without serum (yields 0.1×106 cells/ml)

distribute 100 µl/well of this suspension (i. e. 10000 cells/well) or MEM without serum without cells, respectively, into a standard 96 well tissue culture plate, according to the plate map above add 200 µl/well PBS to all free wells incubate 30' at 37° C./5% $CO_2$ Preparation of the Viability Assay on Cells Under Normal Culture Conditions:

add 30 µl of the 10×106 cells/ml cell suspension to 5 ml MEM+10% FBS (yields 0.06×106 cells/ml)

distribute 100 µl/well of this suspension (i. e. 6000 cells/well) or MEM+10% FBS without cells, respectively, into a standard 96 well tissue culture plate, according to the plate map above add 200 µl/well PBS to all free wells incubate 30' at 37° C./5% $CO_2$ Treatment with the Drugs:

add each 33 µl/well of the 4× concentrated drug solutions in MEM+0.1% FBS to the corresponding wells in all three plates, according to the plate maps above incubate 24 h at 37° C./5% $CO_2$ Day 2: Addition of FBS to Stimulate the Invasion:

Microscopic Observation after 24 h of Treatment:

examine the cells of the viability assays

Addition of FBS (Under a Cell Culture Hood):

prepare MEM+5% FBS: 7.2 ml MEM without serum+0.8 ml FBS (freshly thawed aliquot or rest of the aliquot thawed the day before if kept at 4° C.)

add 33 µl/well to all wells of invasion and viability assays incubate 24 h at 37° C./5% $CO_2$ Day 3: Stop:

Microscopic Observation after 48 h of Treatment:

examine the cells of the viability assays

Viability Assays: MTS Assay:

add each 33 µl/well of the MTS reagent, incubate 2.5 h at 37° C./5% $CO_2$ shake and read absorbance at 490 nm (proportional to the viability)

calculate the background-corrected signals by substracting the means of the background signals in absence of cells from the corresponding signals in presence of cells normalize the background-corrected signals with respect to the mean signal of the negative controls (no drug) (viabilities are thus expressed in "% of control")

Invasion Assays: Fixation and Staining (Formaldehyde Must be Manipulated Under a Fume Cupboard):

freshly prepare 1 µg/ml Hoechst 33342 in 18.5% formaldehyde: 5 ml PBS (not necessarily sterile)+5 ml 37% formaldehyde+1 µl 10 mg/ml Hoechst 33342 (note: for one plate, a smaller volume would be sufficient, but the minimal pipetted volume should not be below 1 µl)

add 50 µl/well to all wells of the invasion assay (yields 4.3% formaldehyde final)

seal with black film (provided with the plates)

incubate at least 7 h at RT

Day 3: 17 (Min. 7 h/Max. 2 Weeks after Fixation and Staining): Analysis of the Invasion Assay:

Lecture using the Cellomics ArrayScan VTI HCS Reader:

BioApplication: SpotDetector.V3

Plate type: Perkin Elmer 96 well

Parameters of the Assay Protocol:

objective: 10×(NA 0.45)

apotome: yes (resulting optical slice: 11.7 µM)

fields per well: 8 autofocus in each field autofocus channel: 1 channel 1 (autofocus on, and photo of the fluorescent beads at the bottom of the wells): filter: XF93-TRITC; exposure time: usually between 0.002 and 0.01 s channel 2 (photo of the stained cells at the same level as the fluorescent beads): filter: XF100-Hoechst; exposure time: usually between 0.02 and 0.1 s; z offset: 0 µM channel 3 (photo of the stained cells 25 µM above the fluorescent beads): filter: XF100-Hoechst; exposure time: usually between 0.02 and 0.1 s; z offset: −25 µM channel 4 (photo of the fluorescent cells 50 µM above the fluorescent beads): filter: XF100-Hoechst; exposure time: usually between 0.02 and 0.1 s; z offset: −50 µM object identification: method: fixed threshold: 100-32767

| object selection parameters: | min. | max. |
|---|---|---|
| SpotArea: | 20 | 1000000000000 |
| SpotShapeBFR: | 0.2 | 1000 |
| SpotShapeBAR: | 0 | 1000 |
| SpotAvgInten: | 200 | 32767 |
| SpotTotalInten: | ≤4000 (thus not limiting) | 1000000000000 |
| TargetAvgInten: | 0 | 32767 |
| TargetTotalInten: | 0 | 1000000000000 |

Analysis of the Results of the Scan Using vHCS Viewer:

export the results: for each well:

number of valid fields number of objects in each valid field in each of the channels 2, 3 and 4 ("field details")

mean numbers of objects per valid field for each well, in each of the channels 2, 3 and 4 exclude wells with less than 6 valid fields per well from further analysis visually check all photos for any apparent problems, such as bad focusing or obviously inhomogeneous collagen structure ("bubbles", . . . ), . . . ; in case of apparent problems: document, then exclude the corresponding wells from further analysis Further Analysis of the Results of the Invasion Assay (Using e. R. Excel):

for each well, calculate the mean invasion distance of the counted cells: (25 μm× number of cells at 25 μm+50 μm×number cells at 50 μm)/sum of cells at 0, 25 and 50 μm for all four parameters (number of cells at 0 μm, number of cells at 25 μm, number of cells at 50 μm, mean invasion distance of the counted cells), calculate means, SD and CV of the replicates (n=6 for the controls; n=3 for the samples)

invalidate any replicate with a CV≥50% (compound to be re-tested, or assay to be repeated if CV≥50% for the untreated negative control or the compound Y-27632-treated positive control). Y27632 is a selective inhibitor of the Rho-associated protein kinase p160ROCK of the following formula

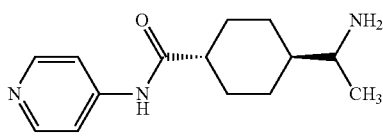

validate the assay only if the mean invasion distance of the cells treated with 10 μM Y-27632 (positive control) is decreased by >40% as compared to the untreated negative control plot graphs of all four parameters (number of cells at 0 μm, number of cells at 25 μm, number of cells at 50 μm, mean invasion distance of the counted cells)

Results

Anti-invasive effect in MDA-MB231 breast cancer cells: 0.5 fold effect compared to 10 μM Y-27632 ref. compound.

| Compound | 0.5 fold effect compared to 10 μM Y-27632 (μM) |
|---|---|
| 6 | 0.7 ± 0.1 |
| 9 | 1.1 ± 0.4 |
| 16 | 0.75 ± 0.19 |
| 17 | 0.83 ± 0.09 |
| 18 | 0.55 ± 0.05 |
| 19 | 0.25 ± 0.05 |
| 21 | 0.17 ± 0.04 |
| 22 | 0.3 ± 0.05 |
| 24 | 0.64 ± 0.2 |
| 25 | 0.5 ± 0.21 |
| 49 | 0.13 ± 0.3 |
| 50 | 1 |
| 129 | 0.2 |

The compounds according to the present invention demonstrate an anti-invasive effect predictive for their activity against cancer.

Therefore, the result of the tests carried out on the compounds disclosed in the present invention show that said compounds and their pharmaceutically acceptable salts, and more particularly compounds (6), (9), (16), (17), (18), (19), (21), (22), (24), (25), (49), (50) and (129) as well as their pharmaceutically acceptable salts, may be used in a method to inhibit, prevent and/or treat cancer.

For this purpose an effective amount of a said compound may be administered to a patient suffering from cancer.

Others indications than cancer may include inflammation, fibrosis, neurodegenerative diseases, ischemia, atherosclerosis, hepatic disorders, such as cholestasis, autoimmune diseases, and ethanol-induced injuries such as alcoholic liver diseases (ALD) including fatty liver, alcoholic hepatitis and cirrhosis, ribosome biogenesis disorders such as Treacher Collins syndrome (TCS), male infertility, alopecia, neurological defects, endocrinopathy syndrome (ANE syndrome), Shwachman-Diamond syndrome (SDS) and neurofibromatosis type 1 (NF1), and HIV-associated pathologies such as dementia, diabetes and myocardial infarction.

Therefore, the result of the tests carried out on the compounds disclosed in the present invention show that said compounds may be useful to inhibit, prevent and/or treat cancer and/or atherosclerosis for patients exhibiting mutated p53, inflammation, fibrosis, neurodegenerative diseases, ischemia, atherosclerosis, pathogenesis of a number of hepatic disorders, such as cholestasis, autoimmune diseases, and ethanol-induced injuries such as alcoholic liver diseases (ALD) including fatty liver, alcoholic hepatitis and cirrhosis, ribosome biogenesis disorders such as Treacher Collins syndrome (TCS), male infertility, alopecia, neurological defects, endocrinopathy syndrome (ANE syndrome), Shwachman-Diamond syndrome (SDS) and neurofibromatosis type 1 (NF1), and HIV-associated pathologies such as dementia, diabetes and myocardial infarction.

The following type of cancer may more particularly be treated by the compounds according to the present invention: namely colorectal cancer, pancreatic cancer, lung cancer including non-small cell lung cancer, breast cancer, bladder cancer, gall bladder cancer, thyroid cancer, melanoma, liver cancer, uterine/cervical cancer, oesophageal cancer, kidney cancer, ovarian cancer, prostate cancer, head and neck cancer, or stomach cancer, etc.

For this purpose an effective amount of a said compound may be administered to a patient suffering from cancer and/or atherosclerosis for patients exhibiting mutated p53, inflammation, fibrosis, neurodegenerative diseases, ischemia, atherosclerosis, hepatic disorders, such as cholestasis, autoimmune diseases, ethanol-induced injuries such as alcoholic liver diseases (ALD) including fatty liver, alcoholic hepatitis and cirrhosis, ribosome biogenesis disorders such as Treacher Collins syndrome (TCS), male infertility, alopecia, neurological defects, endocrinopathy syndrome (ANE syndrome), Shwachman-Diamond syndrome (SDS) and neurofibromatosis type 1 (NF1), and HIV-associated pathologies such as dementia, diabetes and myocardial infarction.

The present invention is also related to the use of at least a compound chosen among a compound of anyone of formula (I), (Iab), (Ia), (Ib), (Ic), (Id), (Ie), (If) as defined above, and compounds (1) to (140) as defined above, or one of its pharmaceutically acceptable salts according to the present invention for the manufacture of a pharmaceutical composition intended for the treatment of cancer and/or atherosclerosis for patients exhibiting mutated p53, inflammation, fibrosis, neurodegenerative diseases, ischemia, atherosclerosis, hepatic disorders, such as cholestasis, autoimmune diseases, ethanol-induced injuries such as alcoholic liver diseases (ALD) including fatty liver, alcoholic hepatitis and cirrhosis, ribosome biogenesis disorders such as Treacher Collins syndrome (TCS), male infertility, alopecia, neurological defects, endocrinopathy syndrome (ANE syndrome), Shwachman-Diamond syndrome (SDS) and neurofibromatosis type 1 (NF1), and HIV-associated pathologies such as dementia, diabetes and myocardial infarction.

The present invention also encompasses pharmaceutical compositions comprising at least a compound chosen among new compounds (9), (16), (17), (18), (19), (20), (21), (22), (23), (24), (25), (37), (38), (39), (48), (49), (50), (52), (83), (84), (85), (86), (87), (88), (89), (90), (91), (92), (123), (124), (125), (126), (127), (128), (129), (130), (131), (132), (133), (134), (135), (136), (137), (138), (139) and (140) as defined above or any pharmaceutically acceptable salt thereof.

Thus, these pharmaceutical compositions contain an effective amount of said compound, and one or more pharmaceutical excipients.

The aforementioned excipients are selected according to the dosage form and the desired mode of administration.

In this context they can be present in any pharmaceutical form which is suitable for enteral or parenteral administration, in association with appropriate excipients, for example in the form of plain or coated tablets, hard gelatine, soft shell capsules and other capsules, suppositories, or drinkable, such as suspensions, syrups, or injectable solutions or suspensions, in doses which enable the daily administration of from 0.1 to 1000 mg of active substance.

The present invention further relates to a method of treatment of patients suffering from cancer and/or atherosclerosis said patients exhibiting mutated p53, inflammation, fibrosis, neurodegenerative diseases, ischemia, atherosclerosis, pathogenesis disorders such as cholestasis, autoimmune diseases and ethanol-induced injuries such as alcoholic liver diseases (ALD) including fatty liver, alcoholic hepatitis and cirrhosis, ribosome biogenesis disorders such as Treacher Collins syndrome (TCS), male infertility, alopecia, neurological defects, endocrinopathy syndrome (ANE syndrome), Shwachman-Diamond syndrome (SDS) and neurofibromatosis type 1 (NF1), and HIV-associated pathologies such as dementia, diabetes and myocardial infarction for patients exhibiting a deregulated p53, which comprises at least a step of administration to a patient suffering thereof of an effective amount of a compound of anyone of formula (I), (Iab), (Ia), (Ib), (Ic), (Id), (Ie) or (If) as defined above and (1) to (140) or one of its pharmaceutically acceptable salts.

The invention claimed is:
1. A method for
reducing breast tumor metastasis in a person expressing a mutated p53, or
reducing p53 expression in a person,
the method comprising administering, to a person in need thereof, an effective amount of a compound of formula (I) or a pharmaceutically acceptable salt thereof:

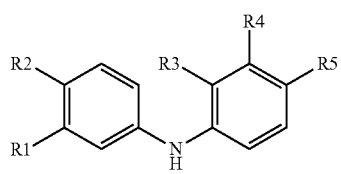

(I)

wherein:
R1 and R2 independently represent:
a hydrogen atom, a $(C_1-C_4)$alkoxy group, a fluoro$(C_1-C_4)$alkoxy group, a benzyloxy group,
a pyridyl-vinyl or pyrimidinyl-vinyl group, said two groups being optionally substituted by a halogen atom, a $(C_1-C_4)$alkyl group or a fluoro$(C_1-C_4)$alkyl group, or
a styryl group optionally substituted by a $(C_1-C_4)$alkoxy group or a fluoro$(C_1-C_4)$alkoxy group,
wherein one of R1 or R2 is a hydrogen atom and the other is different from a hydrogen atom;

R3, R4, and R5 independently represent:
a hydrogen atom, a $(C_1-C_4)$alkyl group,
a —CONHR6 group,
a —CONR7R8 group, or
a —SO$_2$NHR6 group;
R6 represents a hydrogen atom, a —(CHR9)$_m$(CH$_2$)$_n$NR7R8 group, or a $(C_1-C_6)$alkyl group optionally substituted by a hydroxyl group;
R7 and R8 independently represent a $(C_1-C_4)$alkyl group or form together with the nitrogen atom to which they are attached a saturated or unsaturated 5- or 6-membered ring optionally containing a further heteroatom chosen from nitrogen or oxygen, said ring being optionally substituted by a $(C_1-C_4)$alkyl group;
R9 represents a $(C_1-C_2)$alkyl group;
m is 0 or 1,
n is 1, 2, 3, 4, or 5, and
two of R3, R4 and R5 are a hydrogen atom or a $(C_1-C_4)$alkyl group and the last is different from a hydrogen atom or a $(C_1-C_4)$alkyl group.

2. The method according to claim 1, wherein the compound is of formula (Iab) or a pharmaceutically acceptable salt thereof:

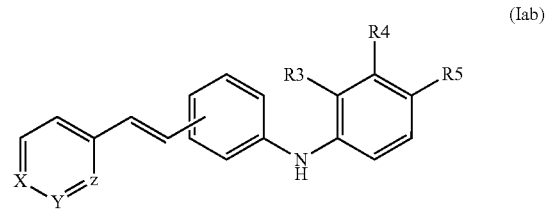

(Iab)

wherein:
X, Y, and Z are independently C or N,
the lateral group

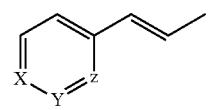

is in the meta or para position with respect to the —NH— group,
at most two of X, Y, and Z are N, and when Y is N, X and Z are C, and
two of R3, R4, and R5 are a hydrogen atom or a $(C_1-C_4)$alkyl group and the last is different from a hydrogen atom or a $(C_1-C_4)$alkyl group.

3. The method according to claim 1, wherein the compound is of formula (Ia) or a pharmaceutically acceptable salt thereof:

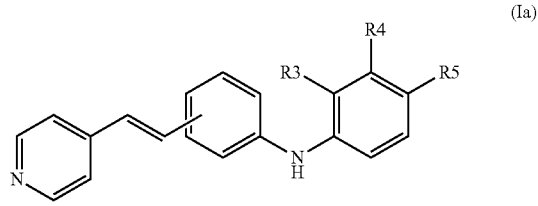

(Ia)

wherein:
the lateral group

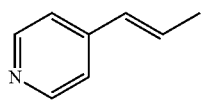

is in the meta or para position with respect to the —NH— group, and
two of R3, R4, and R5 are a hydrogen atom or a (C$_1$-C$_4$)alkyl group and the last is different from a hydrogen atom or a (C$_1$-C$_4$)alkyl group.

4. The method according to claim 1, wherein the compound is of formula (Ib) or a pharmaceutically acceptable salt thereof:

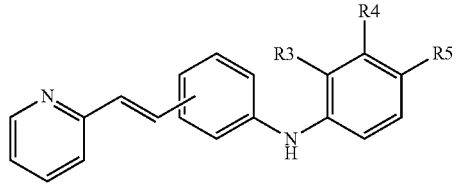

(Ib)

wherein:
the lateral group

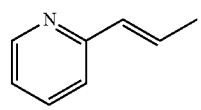

is in the meta or para position with respect to the —NH— group, and
two of R3, R4, and R5 are a hydrogen atom or a (C$_1$-C$_4$)alkyl group and the last is different from a hydrogen atom or a (C$_1$-C$_4$)alkyl group.

5. The method according to claim 1, wherein the compound is of formula (Ic) or a pharmaceutically acceptable salt thereof:

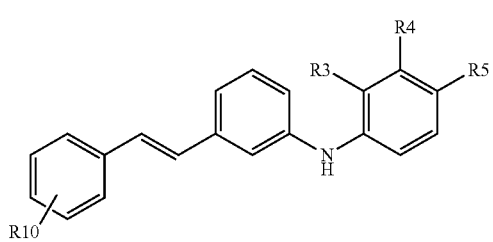

(Ic)

wherein:
R10 is a hydrogen atom, a (C$_1$-C$_4$) alkoxy group, or a fluoro(C$_1$-C$_4$) alkoxy group, and
two of R3, R4, and R5 are a hydrogen atom or a (C$_1$-C$_4$)alkyl group and the last is different from a hydrogen atom or a (C$_1$-C$_4$)alkyl group.

6. The method according to claim 1, wherein the compound is of formula (Id) or a pharmaceutically acceptable salt thereof:

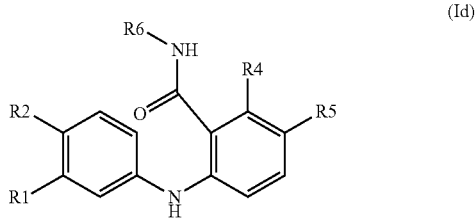

(Id)

wherein:
R4 and R5 are independently a hydrogen atom or a (C$_1$-C$_4$)alkyl group.

7. The method according to claim 1, wherein the compound is of formula (Ie) or a pharmaceutically acceptable salt thereof:

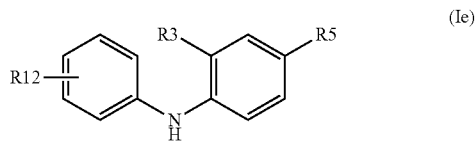

(Ie)

wherein:
R3 is a hydrogen atom or a (C$_1$-C$_4$)alkyl group,
R5 is different from a hydrogen atom or a (C$_1$-C$_4$)alkyl group, and
R12 is a (C$_1$-C$_4$)alkoxy group or a trifluoro(C$_1$-C$_4$)alkoxy group.

8. A method for reducing breast tumor metastasis in a person expressing a mutated p53, or reducing p53 expression in a person, the method comprising administering, to a person in need thereof, an effective amount of a compound selected from the group consisting of:

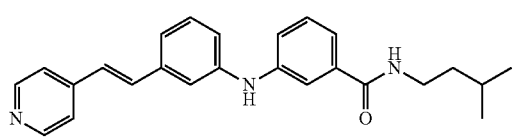

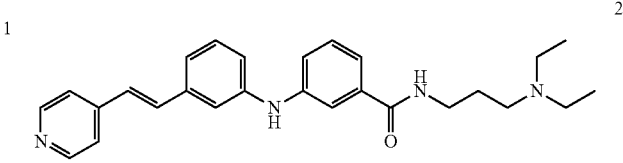

5
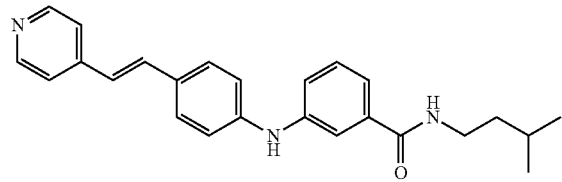
6
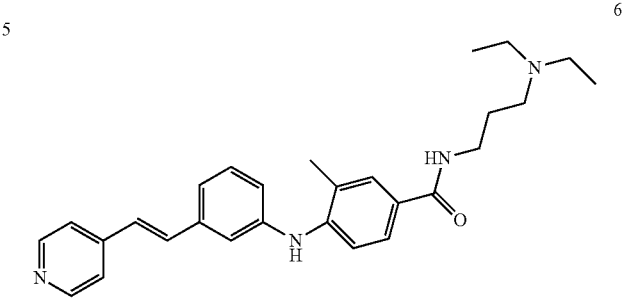
7
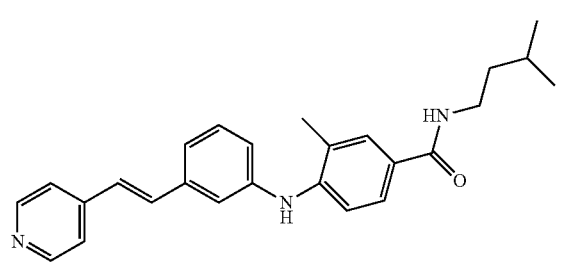
8
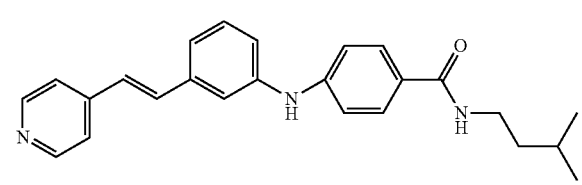
9
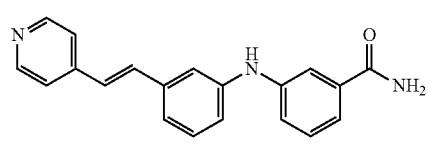
13
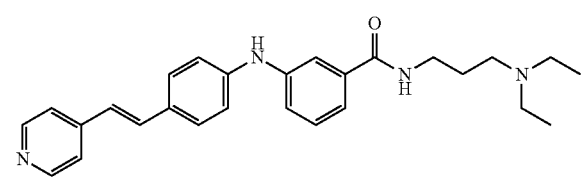
14
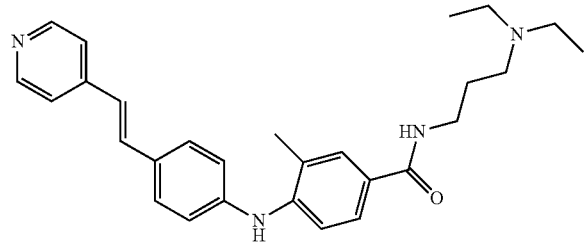
15
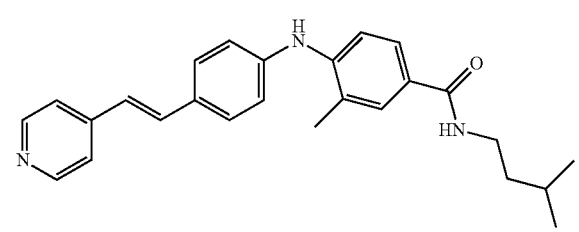
16
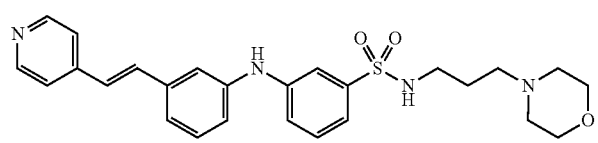
17
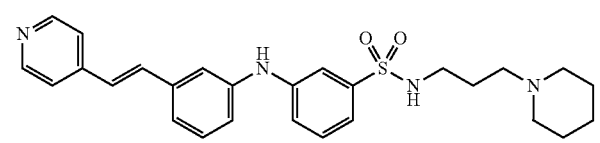
18
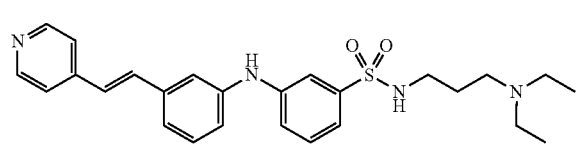
19
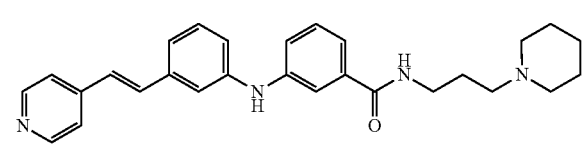 [SMILES: O=C(NCCCN1CCCCC1)c1cccc(Nc2cccc(/C=C/c3ccncc3)c2)c1]
20
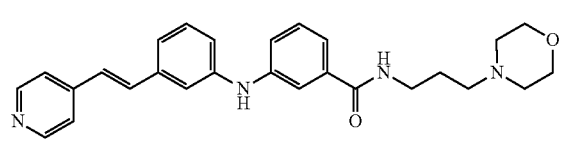 [SMILES: O=C(NCCCN1CCOCC1)c1cccc(Nc2cccc(/C=C/c3ccncc3)c2)c1]
21
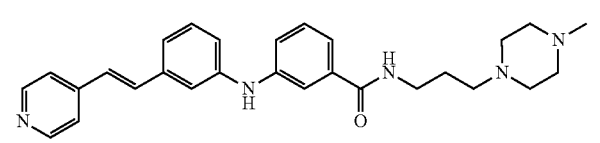 [SMILES: CN1CCN(CCCNC(=O)c2cccc(Nc3cccc(/C=C/c4ccncc4)c3)c2)CC1]

-continued
22
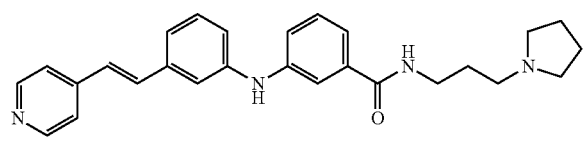 [SMILES: O=C(NCCCN1CCCC1)c1cccc(Nc2cccc(/C=C/c3ccncc3)c2)c1]
23
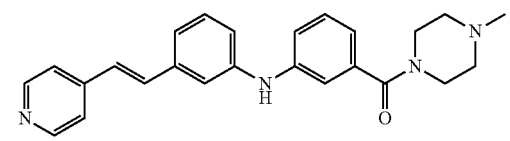 [SMILES: CN1CCN(C(=O)c2cccc(Nc3cccc(/C=C/c4ccncc4)c3)c2)CC1]
24
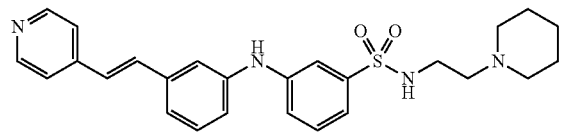 [SMILES: O=S(=O)(NCCN1CCCCC1)c1cccc(Nc2cccc(/C=C/c3ccncc3)c2)c1]
25
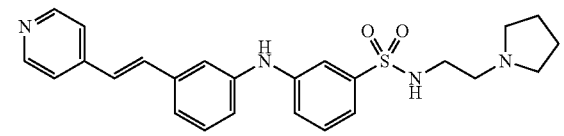 [SMILES: O=S(=O)(NCCN1CCCC1)c1cccc(Nc2cccc(/C=C/c3ccncc3)c2)c1]
127
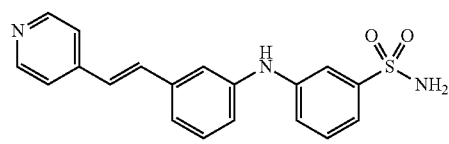
129
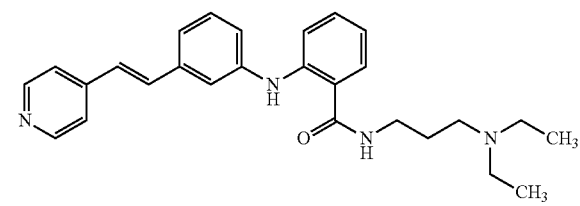
27
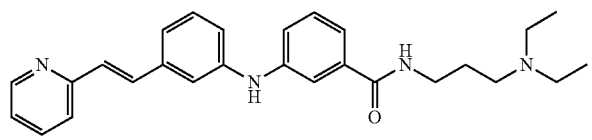 [SMILES: CCN(CC)CCCNC(=O)c1cccc(Nc2cccc(/C=C/c3ccccn3)c2)c1]
28
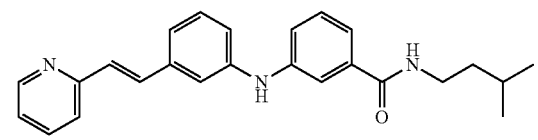 [SMILES: CC(C)CCNC(=O)c1cccc(Nc2cccc(/C=C/c3ccccn3)c2)c1]
30
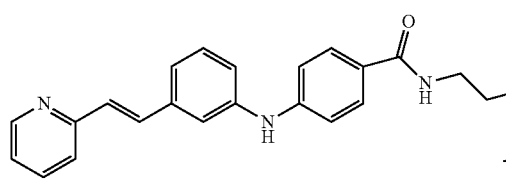
31
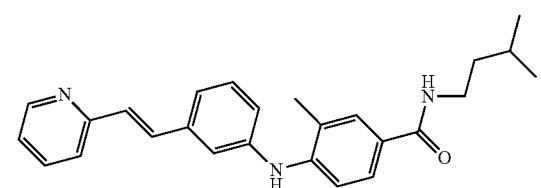
33
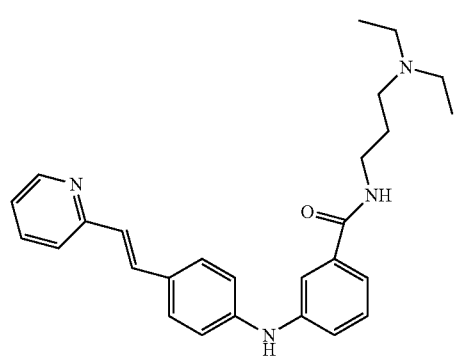
34
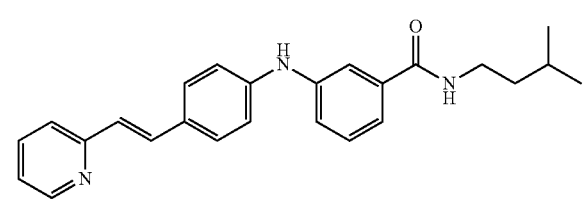 [SMILES: CC(C)CCNC(=O)c1cccc(Nc2ccc(/C=C/c3ccccn3)cc2)c1]
35
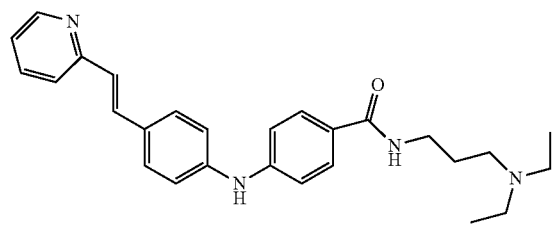
36
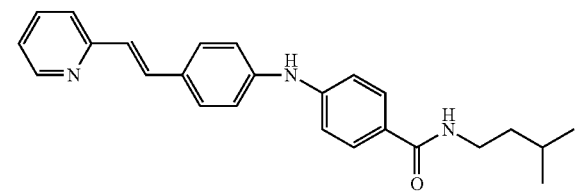 [SMILES: CC(C)CCNC(=O)c1ccc(Nc2ccc(/C=C/c3ccccn3)cc2)cc1]

-continued
130
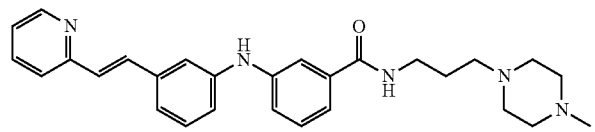 [SMILES: CN1CCN(CCCNC(=O)c2cccc(Nc3cccc(/C=C/c4ccccn4)c3)c2)CC1]
131
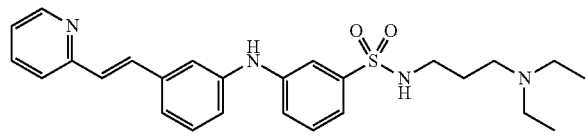
132
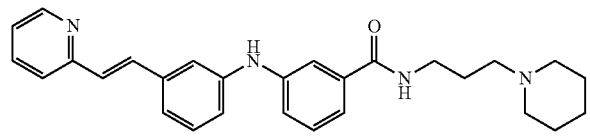 [SMILES: O=C(NCCCN1CCCCC1)c1cccc(Nc2cccc(/C=C/c3ccccn3)c2)c1]
133
134
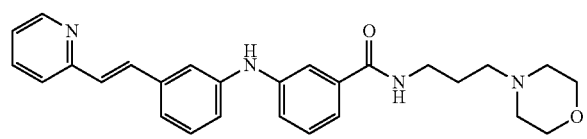 [SMILES: O=C(NCCCN1CCOCC1)c1cccc(Nc2cccc(/C=C/c3ccccn3)c2)c1]
135
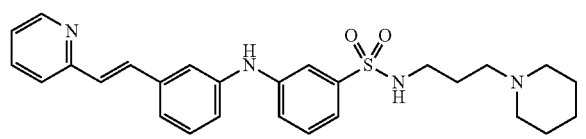 [SMILES: O=S(=O)(NCCCN1CCCCC1)c1cccc(Nc2cccc(/C=C/c3ccccn3)c2)c1]
37
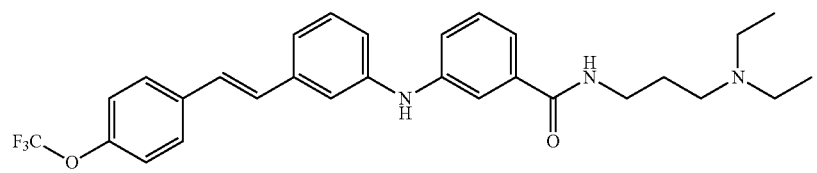 [SMILES: CCN(CC)CCCNC(=O)c1cccc(Nc2cccc(/C=C/c3ccc(OC(F)(F)F)cc3)c2)c1]
38
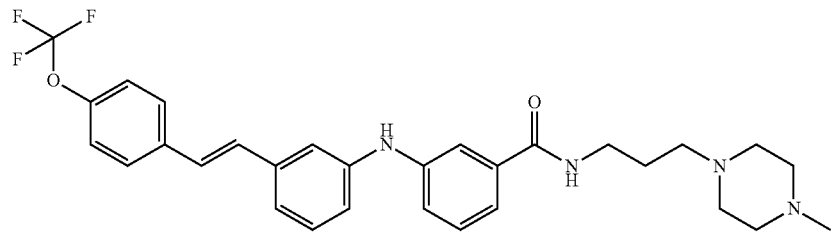 [SMILES: CN1CCN(CCCNC(=O)c2cccc(Nc3cccc(/C=C/c4ccc(OC(F)(F)F)cc4)c3)c2)CC1]
39
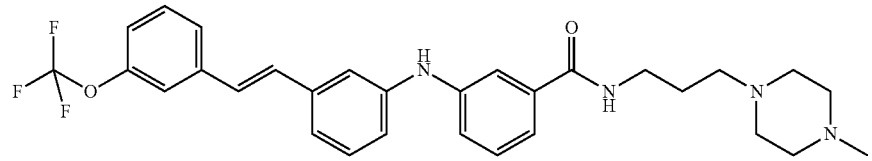 [SMILES: CN1CCN(CCCNC(=O)c2cccc(Nc3cccc(/C=C/c4cccc(OC(F)(F)F)c4)c3)c2)CC1]
40
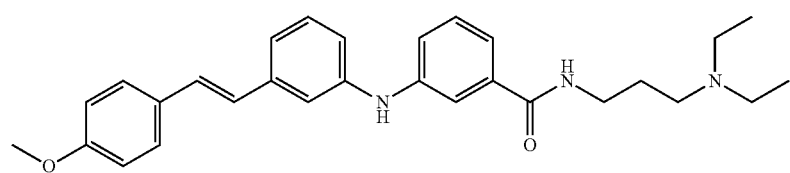 [SMILES: CCN(CC)CCCNC(=O)c1cccc(Nc2cccc(/C=C/c3ccc(OC)cc3)c2)c1]
41
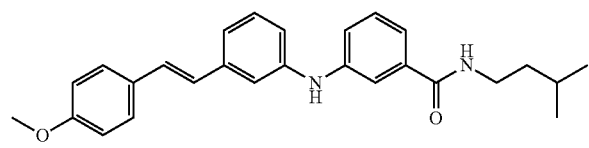 [SMILES: COc1ccc(/C=C/c2cccc(Nc3cccc(C(=O)NCCC(C)C)c3)c2)cc1]
42
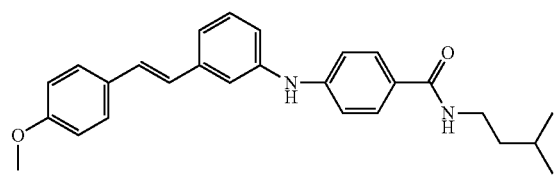 [SMILES: COc1ccc(/C=C/c2cccc(Nc3ccc(C(=O)NCCC(C)C)cc3)c2)cc1]

-continued
43
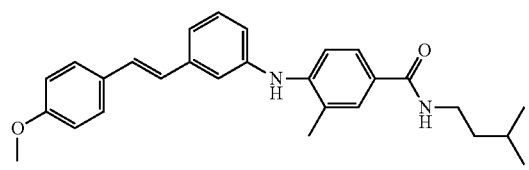 [SMILES: COc1ccc(/C=C/c2cccc(Nc3ccc(C(=O)NCCC(C)C)cc3C)c2)cc1]
44
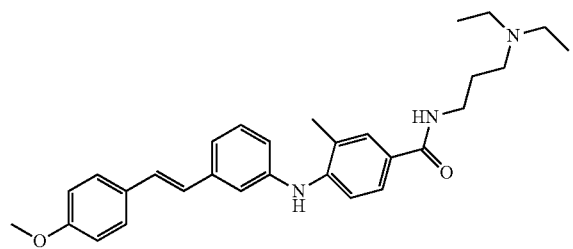
136
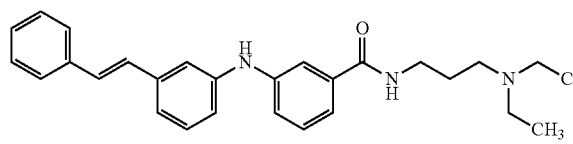
45
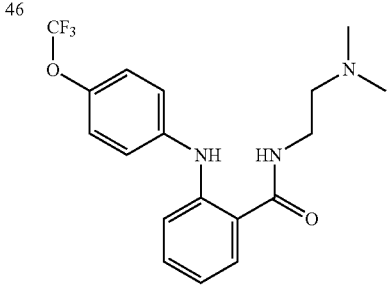
46
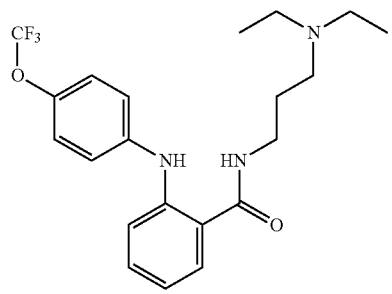 [SMILES: CCN(CC)CCCNC(=O)c1ccccc1Nc1ccc(OC(F)(F)F)cc1]
47
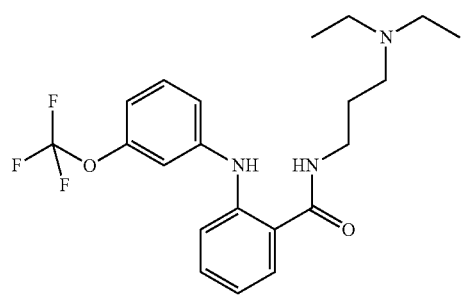 [SMILES: CCN(CC)CCCNC(=O)c1ccccc1Nc1cccc(OC(F)(F)F)c1]
48
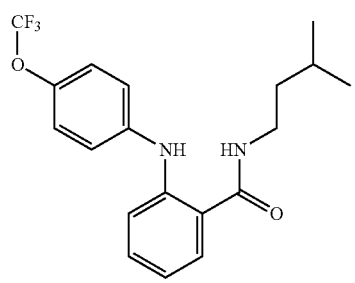 [SMILES: CC(C)CCNC(=O)c1ccccc1Nc1ccc(OC(F)(F)F)cc1]
49
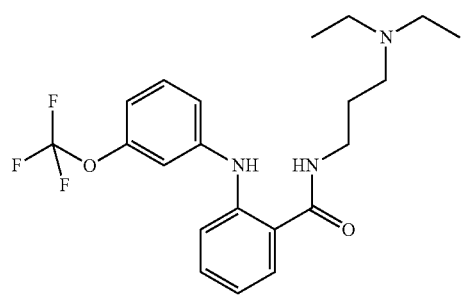 [SMILES: CCN(CC)CCCNC(=O)c1ccccc1Nc1cccc(OC(F)(F)F)c1]
50
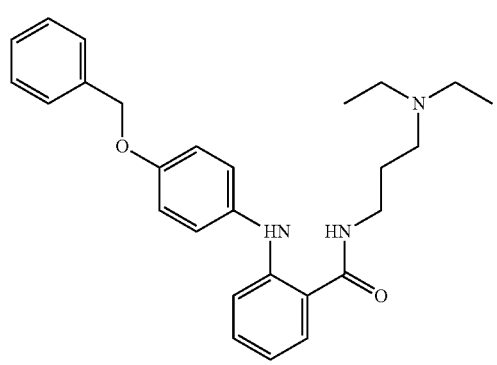 [SMILES: CCN(CC)CCCNC(=O)c1ccccc1Nc1ccc(OCc2ccccc2)cc1]
53
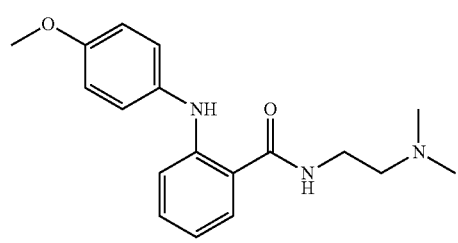

-continued
54
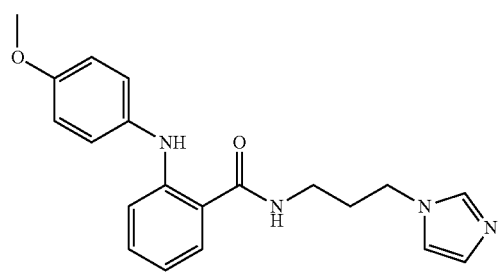 [SMILES: COc1ccc(Nc2ccccc2C(=O)NCCCn2ccnc2)cc1]
55
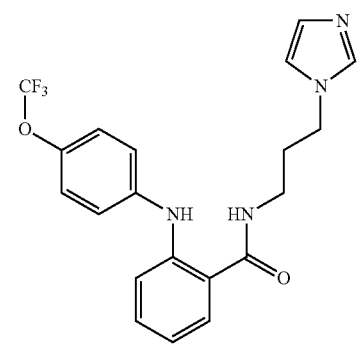 [SMILES: O=C(NCCCn1ccnc1)c1ccccc1Nc1ccc(OC(F)(F)F)cc1]
58
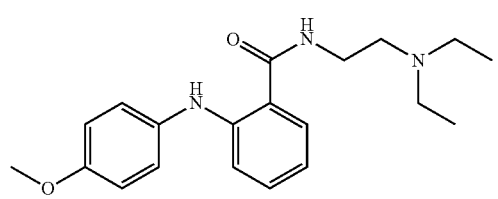 [SMILES: CCN(CC)CCNC(=O)c1ccccc1Nc1ccc(OC)cc1]
59
60
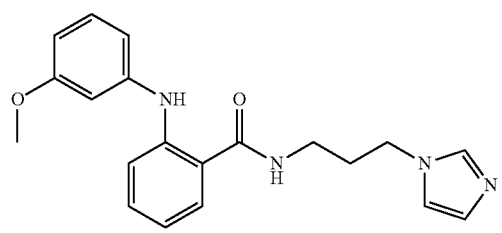 [SMILES: COc1cccc(Nc2ccccc2C(=O)NCCCn2ccnc2)c1]
61
62
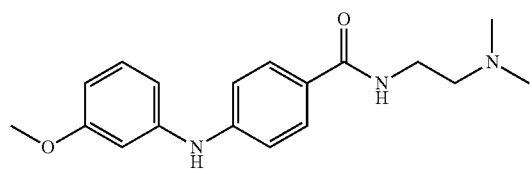
63
64
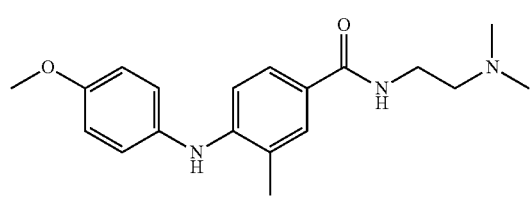
65
66
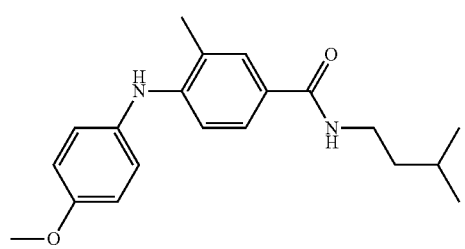 [SMILES: COc1ccc(Nc2ccc(C(=O)NCCC(C)C)cc2C)cc1]
67
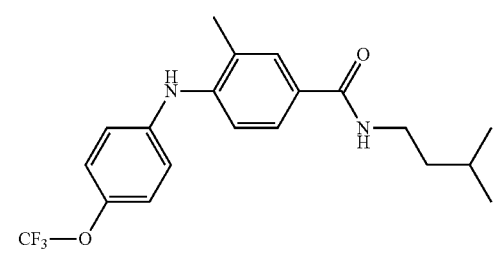 [SMILES: Cc1cc(C(=O)NCCC(C)C)ccc1Nc1ccc(OC(F)(F)F)cc1]

-continued
68
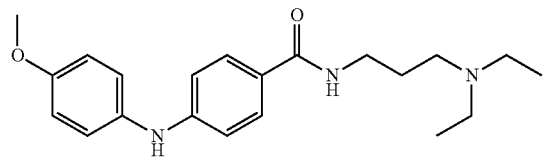 [SMILES: CCN(CC)CCCNC(=O)c1ccc(Nc2ccc(OC)cc2)cc1]
69
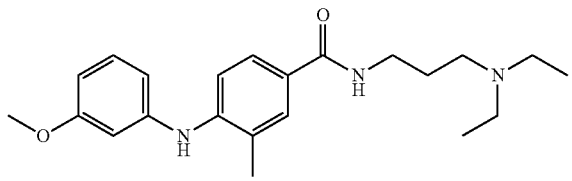 [SMILES: CCN(CC)CCCNC(=O)c1ccc(Nc2cccc(OC)c2)c(C)c1]
70
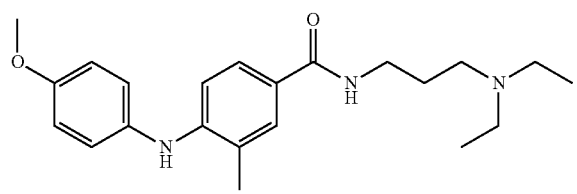 [SMILES: CCN(CC)CCCNC(=O)c1ccc(Nc2ccc(OC)cc2)c(C)c1]
71
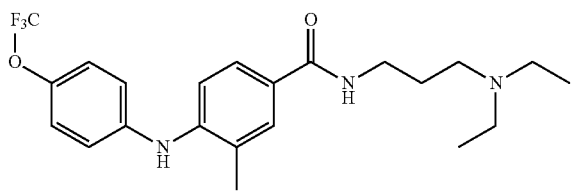 [SMILES: CCN(CC)CCCNC(=O)c1ccc(Nc2ccc(OC(F)(F)F)cc2)c(C)c1]
72
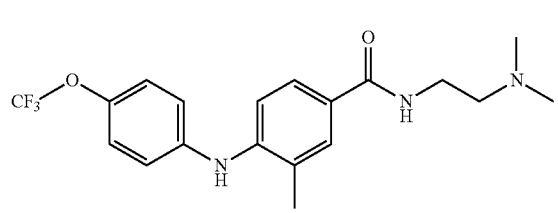 [SMILES: Cc1cc(C(=O)NCCN(C)C)ccc1Nc1ccc(OC(F)(F)F)cc1]
75
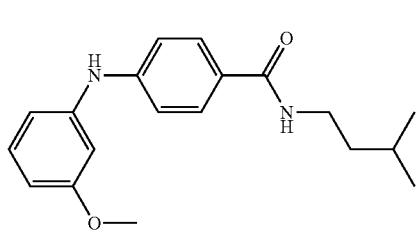
77
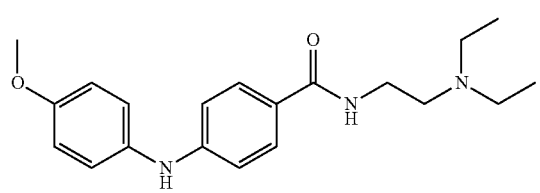 [SMILES: CCN(CC)CCNC(=O)c1ccc(Nc2ccc(OC)cc2)cc1]
81
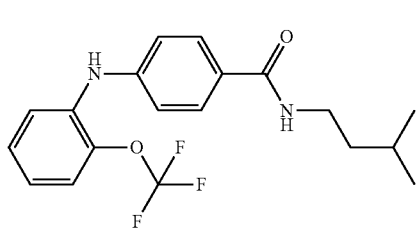
82
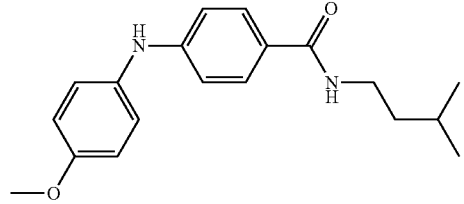 [SMILES: COc1ccc(Nc2ccc(C(=O)NCCC(C)C)cc2)cc1]
83
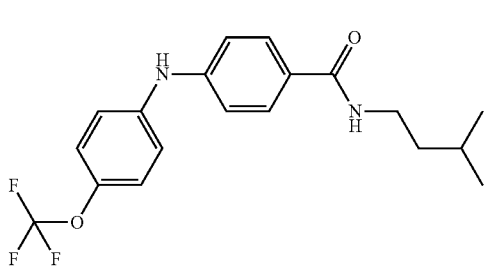
84
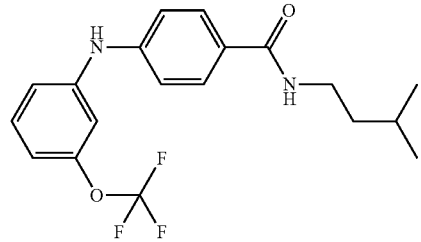 [SMILES: CC(C)CCNC(=O)c1ccc(Nc2cccc(OC(F)(F)F)c2)cc1]
85
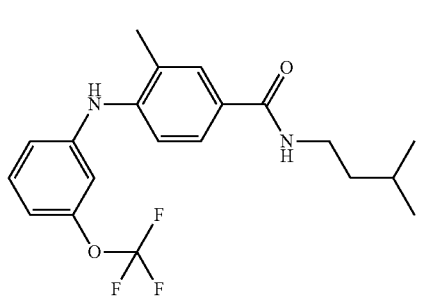
86
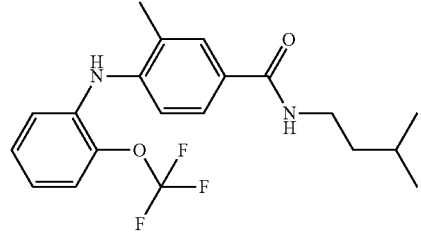 [SMILES: Cc1cc(C(=O)NCCC(C)C)ccc1Nc1ccccc1OC(F)(F)F]
87

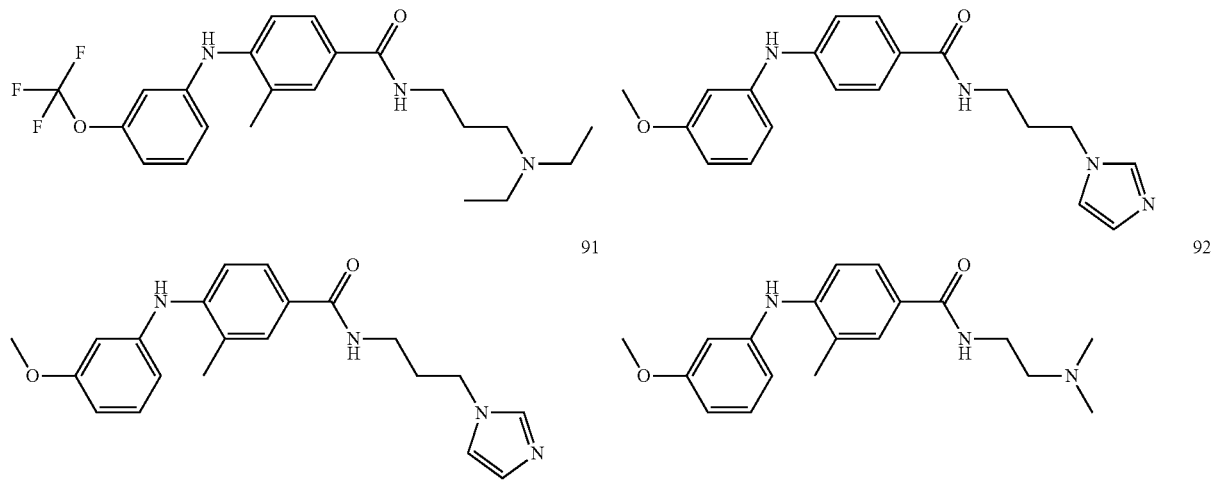
and pharmaceutically acceptable salts thereof.
9. The method according to claim 1, wherein the compound is selected from the group consisting of the compounds:
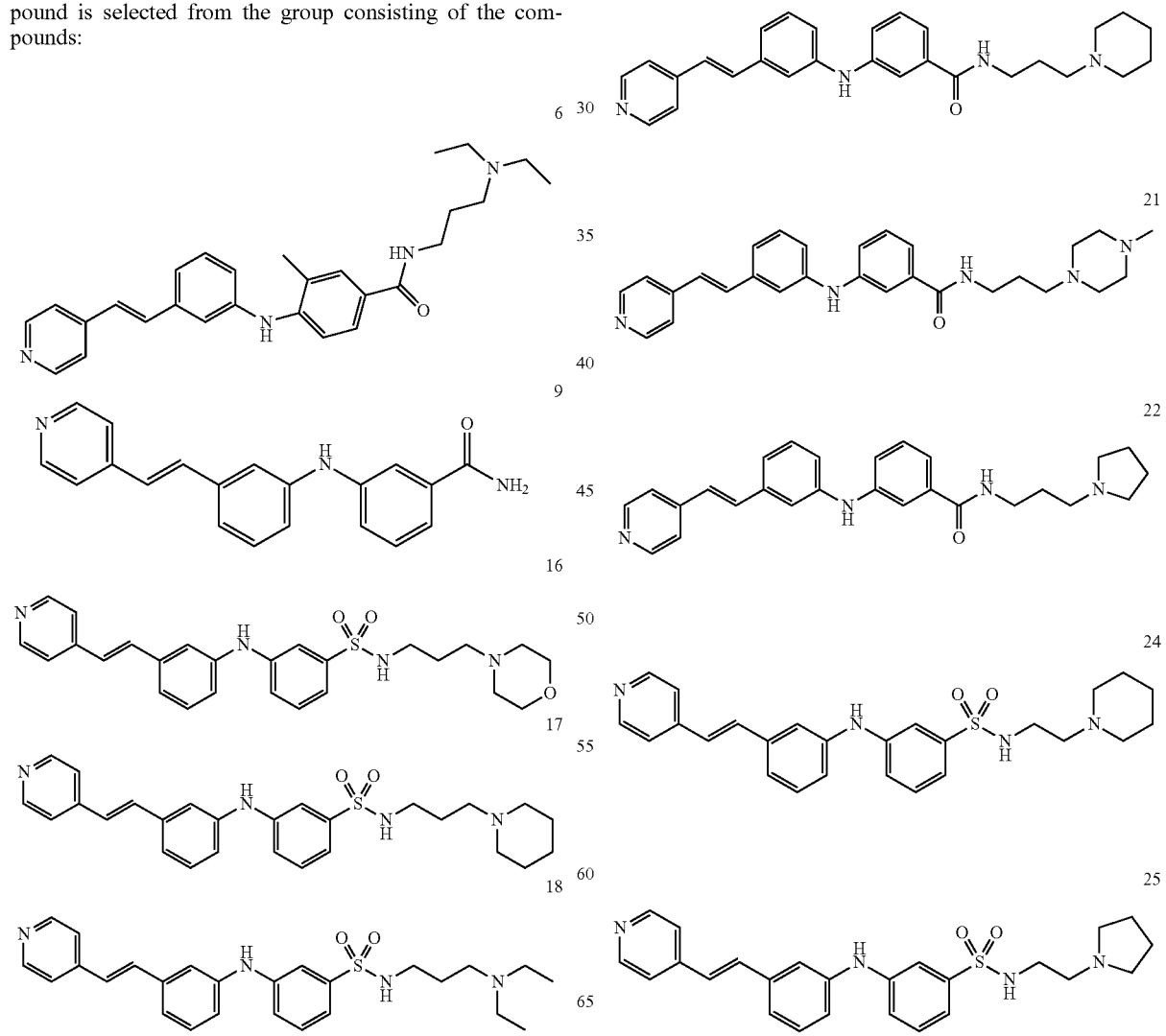

49
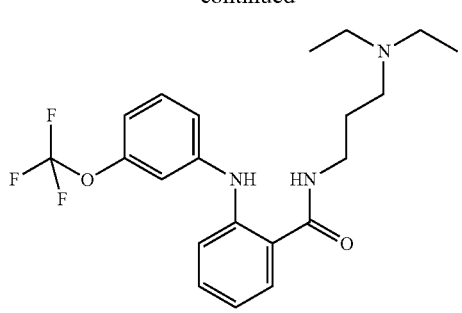
50
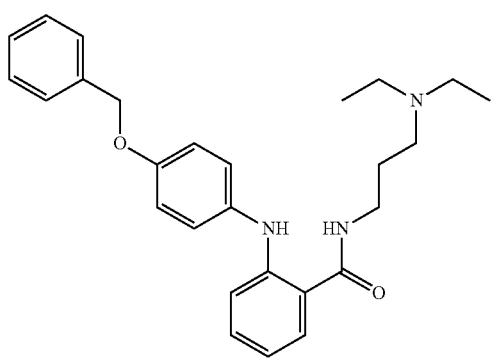
129
and pharmaceutically acceptable salts thereof.
10. The method according to claim 8, wherein the compound is selected from the group consisting of the compounds (9), (16), (17), (18), (19), (20), (21), (22), (23), (24), (25), (37), (38), (39), (48), (49), (50), (83), (84), (85), (86), (87), (88), (90), (91), (92), (127), (129), (130), (131), (132), (133), (134), (135), (136), and pharmaceutically acceptable salts thereof.
11. The method according to claim 1, wherein the method is for reducing p53 expression in a person.
\* \* \* \* \*